US012458624B2

(12) United States Patent
Dhanoa

(10) Patent No.: US 12,458,624 B2
(45) **Date of Patent: *Nov. 4, 2025**

(54) DEUTERIUM-ENRICHED SUBSTITUTED PHENOXYPHENYL ACETIC ACIDS AND ACYLSULFONAMIDES

(71) Applicant: Daljit Singh Dhanoa, Del Mar, CA (US)

(72) Inventor: Daljit Singh Dhanoa, Del Mar, CA (US)

( * ) Notice: Subject to any disclaimer, the term of this patent is extended or adjusted under 35 U.S.C. 154(b) by 713 days.

This patent is subject to a terminal disclaimer.

(21) Appl. No.: 17/780,971

(22) PCT Filed: Dec. 1, 2020

(86) PCT No.: PCT/US2020/062662

§ 371 (c)(1),
(2) Date: May 28, 2022

(87) PCT Pub. No.: WO2021/118826

PCT Pub. Date: Jun. 17, 2021

(65) Prior Publication Data

US 2023/0039319 A1 Feb. 9, 2023

Related U.S. Application Data

(60) Provisional application No. 62/947,460, filed on Dec. 12, 2019.

(51) Int. Cl.

| | |
|---|---|
| ***A61K 45/06*** | (2006.01) |
| ***A61K 31/36*** | (2006.01) |
| ***A61K 31/4184*** | (2006.01) |
| ***A61K 31/519*** | (2006.01) |
| ***A61P 13/08*** | (2006.01) |
| ***A61P 35/00*** | (2006.01) |
| ***C07D 317/60*** | (2006.01) |

(52) U.S. Cl.

CPC .......... *A61K 31/36* (2013.01); *A61K 31/4184* (2013.01); *A61K 31/519* (2013.01); *A61P 13/08* (2018.01); *C07D 317/60* (2013.01); *C07B 2200/05* (2013.01)

(58) Field of Classification Search

None

See application file for complete search history.

(56) References Cited

U.S. PATENT DOCUMENTS 5,565,485 A * 10/1996 Bagley .................... C07C 59/70 548/254
5,767,310 A * 6/1998 Bagley ................. C07D 405/12 562/466
11,634,428 B2 * 4/2023 Dhanoa .............. A61K 31/4706 514/260.1

FOREIGN PATENT DOCUMENTS

WO WO-2008124803 A1 * 10/2008 ................ A61P 1/04
WO WO-2010127197 A2 * 11/2010 ......... A61K 31/4025

OTHER PUBLICATIONS

Winn et al., 2,4-Diarylpyrrolidine-3-carboxylic Acids Potent ETA Selective Endothelin Receptor Antagonists. 1. Discovery of A-127722J. Med. Chem. 1996, 39, 5, 1039-1048) (Year: 1996).*

Graham S Timmins (2014) Deuterated drugs: where are we now?, Expert Opinion on Therapeutic Patents, 24:10, 1067-1075 (Year: 2014).*

CAS Scifinder CAS Registry No. 866206-54-4 (Year: 2025).*

Porvasnik et al., PRX-08066, a Novel 5-Hydroxytryptamine Receptor 2B Antagonist, Reduces Monocrotaline-Induced Pulmonary Arterial Hypertension and Right Ventricular Hypertrophy in Rats, The Journal of Pharmacology and Experimental Therapeutics vol. 334, Issue 2, Aug. 2010, pp. 364-372 (Year: 2010).*

Scifinder CAS Registry No. 173450-67-4 (Year: 2025).*

William et al. Pharmacology of L-754, 142, a highly potent, orally active, nonpeptidyl endothelin antagonist, J Pharmacol Exp Ther. Dec. 1995;275(3):1518-26, abstract (Year: 1995).*

* cited by examiner

*Primary Examiner* — Kortney L. Klinkel
*Assistant Examiner* — Alison Azar Salamatian

(57) ABSTRACT

The present invention is concerned with deuterium-enriched substituted phenoxy-(3, 4-methylenedioxy)phenylacetic acid and acylsulfonamide derivatives of general structural formula I, their optically active or pure enantiomers and diastereomers, and pharmaceutical salts thereof,

I

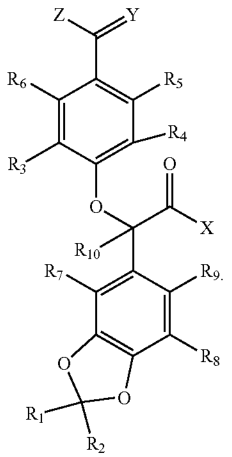

These compounds have selective antagonist activity for endothelin receptors or both endothelin and angiotensin II receptors, and are useful in the treatment of diseases mediated by endothelin and angiotensin-II and their receptors.

1 Claim, No Drawings

DEUTERIUM-ENRICHED SUBSTITUTED PHENOXYPHENYL ACETIC ACIDS AND ACYLSULFONAMIDES

PRIORITY CLAIM

This application claims priority from International Application No. PCT/US 2020/062662, herein incorporated by reference in its entirety and for all purposes and International Application No. PCT/US2020/062662 claims priority from Provisional Application No. 62/947,460; Filed on: Dec. 12, 2019 herein incorporated by reference in its entirety and for all purposes.

SUMMARY OF THE INVENTION

The present invention is concerned with novel deuterium-enriched substituted phenoxy-(3, 4-methylenedioxy)phenylacetic acid and acylsulfonamide derivatives of general structural formula I, their optically active enantiomers and diastereoisomers, and pharmaceutical salts and compositions thereof, as well as combination therapies which include compounds of the present invention,

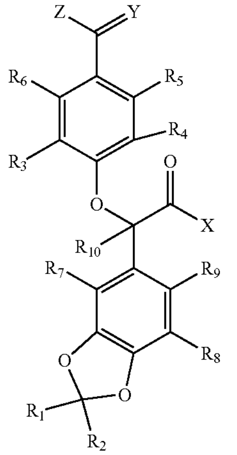

I

Wherein, $R_1$ and $R_2$ are D (Deuterium), H or F;

$R_3$ and $R_4$, are independently selected from H, D, $CH_2$—$CH_2$—$CD_3$, $CH_2$—$CD_2$-$CD_3$, $CD_2$-$CD_2$-$CD_3$, $CD_2$-CHD-$CHD_2$, $CH_2CH_2CH_3$, $CD_2$-$CD_2$-O—$CD_2CD_3$, $CH_2CH_2OCD_3$, $CH_2CH_2OCH_2CH_3$; $CH_2CH_2OCD_2CD_3$; $CD_2CD_2OCH_2CH_3$;

$R_5$, $R_6$, $R_7$, $R_8$, $R_9$, and $R_{10}$, are independently D, H, F;

X is OD, OH, $O^-K^+$, $NHSO_2$—$(C_6H_4)$-4-i-Pr, $NDSO_2$—$(C_6H_4)$-4-i-Pr, $N^-K^+SO_2$—$(C_6H_4)$-4-i-Pr, $NDSO_2$—$(C_6D_4)$-4-i-Pr-$d_7$, $NDSO_2$—$(C_6H_4$-$d_2)$-4-i-Pr-$d_7$, $NDSO_2$—$(C_6H_4)$-4-i-Pr-$d_7$, $NDSO_2$—$(C_6H_4)$-4-i-Pr-$d_1$, $NDSO_2$-4-$(C_6H_4)$-i-Pr-$(d_6)$, $NDSO_2$—$(C_6H_4)$-4-i-Pr-$(d_3)$, $NHSO_2$—$(C_6H_4)$-4-iPr-$d_1$, $NHSO_2$—$(C_6H_4)$-4-iPr-$d_3$, $NHSO_2$—$(C_6H_4)$-4-iPr-$d_4$, $NHSO_2$—$(C_6H_4)$-4-iPr-$d_6$, $NHSO_2$—$(C_6H_4)$-4-iPr-$d_7$, OH, $O^-K^+$, $O^-Na^+$, $O^-Li^+$, $OCD_3$, $OCD_2CD_3$, $OCD_2CD_2CD_3$;

Y is O, $D_2$, DH, HH;

Z is OD, OH, $O^-K^+$, $O^-Na^+$, $O^-Li^+$, $OCD_3$, $OCD_2CD_3$; $OCD_2CD_2CD_3$.

The compounds of formula I, their enantiomers, diastereomers, atropisomers and pharmaceutical salts and combinations thereof, have selective antagonist activity for endothelin receptors and dual (combined) antagonist activity for angiotensin II receptors, and are particularly useful for the treatment of diseases mediated by endothelin and angiotensin-II (Angiotensin-II receptor subtype 1, $AT_1$) and their receptors including pulmonary arterial hypertension, pulmonary hypertension associated with chronic obstructive pulmonary disease (COPD), right ventricular hypertrophy, pulmonary vascular remodeling, lung fibrosis, hypertension, left ventricular hypertrophy, congestive heart failure, arrhythmia, arterial fibrillation, digital ulcers, idiopathic pulmonary fibrosis, idiopathic pulmonary hypertension, acute kidney disease, chronic kidney disease, renal failure, cyclosporin-induced renal failure, IgA nephropathy (IgAN), focal segmental glomerulosclerosis (FSGS), diabetic nephropathy, scleroderma, digital ulcers, prostate cancer, breast cancer, lung cancer, ovarian cancer, colon cancer, kidney cancer, arteriosclerosis, myocardial infarction, angina pictoris, cerebral and cardiac ischemia, post-ischemic renal failure, stroke, vasospasm, Raynaud's disease, asthma, diabetes, obesity, erectile dysfunction, benign prostatic hyperplasia, endotoxic shock, endotoxin-induced, multiple organ failure, sepsis, and inflammatory bowel diseases including Crohn's disease and ulcerative colitis.

This invention further constitute a method for antagonizing endothelin receptors and dual (both) endothelin and angiotensin-II receptors in mammal, including humans, which comprises administering to a mammal in need of such treatment an effective amount of a compound of structural Formula I.

BACKGROUND OF THE INVENTION

Endothelin (ET) is a highly potent vasoconstrictor synthesized and released by endothelial and kidney cells. ET is an endogenous peptide hormone comprised of 21 amino acids. There are three distinct isoforms of endothelins, ET-1, ET-2, and ET-3 that bind to two endothelin receptors. The vasoconstricting effect is caused by the binding of endothelin to its receptors on the vascular smooth muscle cells [Yanagisawa M, et al. A novel potent vasoconstrictor peptide produced by vascular endothelial cells. Nature, 1988, 322, 411-415; FEBS Letters, 1988, 231, 440-444; Biochem. Biophys. Res. Commun. 1988, 154, 868-875].

Endothelin receptors are present in high concentrations both in the mammalian peripheral tissues and in the central nervous system [Drug of Today, 1992, 28(5), 303]. Endothelin can induce numerous biological responses in vascular and non-vascular tissues by binding to its receptors subtypes endothelin receptor A and B, $ET_A$ receptor and $ET_B$ receptor respectively. In addition to cardiovascular smooth muscle, neural and atrial sites, endothelin receptors may also be found in brain, kidney, lung, gastrointestinal, urogenital, uteral, and placental tissues.

Elevated levels of endothelin are found in the blood of patients with essential hypertension, acute myocardial infarction, pulmonary hypertension, atherosclerosis of patients with asthma compared to normal levels [Japan J. Hypertension, 1989, 12, 79; J. Vascular Medicine Biology 1990, 2, 207; J. Am. Med. Association 1990, 264, 2868; The Lancet, 1990, ii, 207; The Lancet, 1989, ii, 747-748]. Endothelin induces sustained contraction of vascular or non-vascular smooth muscles. Excess production and secretion of endothelin is believed to be one of the factors responsible for pulmonary hypertension, hypertension, arteriosclerosis, myocardial infarction, angina pectoris, cerebral vasospasm, Raynaud' disease, and bronchial asthma. Stimulation of endothelin receptor A ($ET_A$) promotes vasoconstriction while stimulation of endothelin receptor B ($ET_B$) receptors causes either vasoconstriction or vasodilation. The main effects of endothelin are observed in the cardiovascular system, particularly in the coronary, renal, cerebral and mesenteric circulation, and the effects of endothelin are often long lasting. Stimulation of endothelin receptors also mediates further biological responses in cardiovascular and non-cardiovascular tissues such as cell proliferation and matrix formation. Studies in patients with congestive heart failure have demonstrated an excellent correlation between the elevated levels of endothelin in the plasma and the severity of the disease [Mayo Clinic Proc., 1992, 67, 719-724].

Endothelin was found to control the release of many physiological substances such as renin, arterial natriuretic peptide, endothelium-derived relaxing factor (EDRF), thromboxane $A_2$ [J. Cardiovas. Pharmacol. 1989, 13, 589-592], prostacyclin, norepinephrine, angiotensin-II and substance P [Biochem. Biophys. Res. Comm. 1988, 157, 1164-1168; Biochem. Biophys. Res. Comm. 1989, 155, 167-172; Proc. Natl. Acad. Sci. USA. 1989, 85, 9797-9800; J. Cardiovasc. Pharmacol. 1989, 13, 589-592; Japan. J. Hypertension 1989, 12, 76; Neuroscience Letters, 1989, 102, 179-184].

Endothelin also causes contraction of the smooth muscle of the gastrointestinal tract and the uterine smooth muscle [Febs Letters, 1989, 247, 337-340; Eur. J. Pharmacol. 1988, 154, 227-228; Biochem. Biophys. Res. Commun. 1989, 159, 317-323]. Endothelin also catalyzes the growth of rat vascular smooth muscle cells which would suggest a possible relevance to arterial hypertrophy [Atherosclerosis, 1989, 78, 225-228] Endothelin has been shown in experimental models of cerebral vasospasm and acute renal failure to be one of the mediators causing cerebral vasospasm following a subarachnoid hemorrhage and renal failure [Japan. Soc. Cereb. Blood Flow & Metabol. 1989, 1, 73; J. Clin. Invest. 1989, 83, 1762-1767].

A study has demonstrated that addition of cyclosporine to renal cell culture increased endothelin secretion [Eur. J. Pharmacol. 1990, 180, 191-192].

It is also shown in another study that administration of cyclosporine to rats led to a decrease in the glomerular filtration rate and an increase in the blood pressure, in association with a remarkable increase in the circulating endothelin level. This cyclosporine-induced renal failure can be suppressed by the administration of anti-endothelin antibody [Kidney Int., 1990, 37, 1487-1491]. These studies provide a strong evidence in support of a significant involvement of endothelin in the pathogenesis of cyclosporin-induced renal disease. (Cyclosporin is also spelled as cyclosporine and ciclosporin).

Endothelins (ET-1, ET-2, and ET-3) are 21-amino acid peptides produced and distributed in nearly all tissues. Endothelins are potent vasoconstrictors and important mediators of cardiac, renal, endocrine and immune functions [J. Am. Coll. Surg., 1995, 180:621]. They participate in bronchoconstriction and regulate neurotransmitter release, activation of inflammatory cells, fibrosis, cell proliferation, and cell differentiation [Pharmacol Rev. 1994, 46: 328]. Endothelin-1 is produced in the human prostate gland and endothelin receptors have been identified in this tissue [Eur. J. Pharmacol. 1988, 349, 123-128]. Since endothelin is a contractile and proliferative agent, endothelin antagonists could be useful in the treatment of benign prostate hypertrophy. Elevated levels of endothelin have been found in patients with recurrent airway obstruction [Pulm. Pharm. Ther. 1998, 11: 231-235], asthma [Am. J. Resp. Crit. Care Med., 1995, 151:1034-1039], acute renal failure [Med. Philos. 1994, 13 (1), 64-66], chronic renal failure [Clin. Sci. (London) 1992, 82, 255], ischemic heart disease [Am. Heart J., 1990, 119, 801], stable or unstable angina [Br. Heart, J., 1991, 66, 7], pulmonary hypertension [Ann. Internal. Medicine, 1991, 114, 464], congestive heart failure [Am. J. Hypertension, 1991, 4, 9A], preeclampsia [Am. J. Obstet. Gynecol., 1992, 166, 962], diabetes [Diabetes Care, 1992, 15(8), 1038], Crohn's disease [Lancet, 1992, 339, 381], atherosclerosis [New Eng. J. Med. 1991, 325, 997], and others.

Diseases associated directly or indirectly with physiologically elevated levels of endothelin are potentially treatable with compounds that are potent, selective and efficacious endothelin receptor antagonists. Compounds that antagonize the endothelin receptors are preferred as therapeutic agents that are useful in the prevention and treatment of diseases and disorders regulated directly and indirectly with endothelin receptors. These diseases include pulmonary arterial hypertension, pulmonary hypertension associated with chronic obstructive pulmonary disease (COPD), right ventricular hypertrophy, pulmonary vascular remodeling, lung fibrosis, hypertension, left ventricular hypertrophy, congestive heart failure, arrhythmia, arterial fibrillation, digital ulcers, idiopathic pulmonary fibrosis, idiopathic pulmonary hypertension, acute kidney disease, chronic kidney disease, renal failure, IgA nephropathy (IgAN), focal segmental glomerulosclerosis (FSGS), diabetic nephropathy, scleroderma, digital ulcers, prostate cancer, breast cancer, lung cancer, ovarian cancer, colon cancer, kidney cancer, arteriosclerosis, myocardial infarction, angina pictoris, cerebral and cardiac ischemia, post-ischemic renal failure, stroke, vasospasm, Raynaud's disease, asthma, diabetes, obesity, erectile dysfunction, benign prostatic hyperplasia, endotoxic shock, endotoxin-induced, multiple organ failure, sepsis and inflammatory bowel diseases.

A number of endothelin receptor antagonists such as Bosentan, have been identified and developed for the treatment of pulmonary arterial hypertension. The current invention is concerned with the individual antagonism of endothelin receptors ($ET_A$ and $ET_B$) by compounds of the structural formula I or pharmaceutically acceptable salts thereof for the treatment of include pulmonary arterial hypertension, pulmonary hypertension associated with chronic obstructive pulmonary disease (COPD), right ventricular hypertrophy, pulmonary vascular remodeling, hypertension, left ventricular hypertrophy, congestive heart failure, arrhythmia, arterial fibrillation, lung fibrosis, idiopathic pulmonary fibrosis, idiopathic pulmonary hypertension, acute kidney disease, chronic kidney disease, renal failure, IgA nephropathy (IgAN), focal segmental glomerulosclerosis (FSGS), diabetic nephropathy, scleroderma, digital ulcers, prostate cancer, breast cancer, lung cancer, ovarian cancer, colon cancer, kidney cancer, arteriosclerosis, myocardial infarction, angina pictoris, cerebral and cardiac ischemia, post-ischemic renal failure, stroke, vasospasm, Raynaud's disease, asthma, diabetes, obesity, erectile dysfunction, benign prostatic hyperplasia, endotoxic shock, endotoxin-induced, multiple organ failure, sepsis and inflammatory bowel diseases.

This invention is also concerned with dual antagonism of both endothelin receptors and angiotensin-II ($AT_1$ receptor subtype of angiotensin-II receptor) receptors by the compound of structural formula I or pharmaceutically acceptable salts thereof.

Angiotensin-II (Ang II), produced by the renin angiotensin system (RAS), is a potent vasoconstrictor and thus plays a major role in the pathophysiology of hypertension [New. Engl. J. Med. 1996, 334, 1649]. The octapeptide hormone, Ang-II has two receptor subtypes, $AT_1$ and $AT_2$. $AT_1$ receptor antagonists have been developed for the treatment of hypertension and are found to be more effective and better tolerated than other class of drugs [J. Med. Chem. 1996, 39, 626-629; J. Hypertens., 2003, 21, 1011-1053; Curr. Opin. Invest. Drug, 2005, 6, 269-274; Am. J. Hypertens. 2003, 16, 1066-1073; J. Cardiovas. Pharmacol. 1990, vol 5 (Suppl. 3), pp S1-S5]. Despite the availability of blood pressure lowering drugs for the treatment of hypertension, adequate control of blood pressure is still not accomplished in over one-third of the hypertensive population [Arch. Intern. Med. 2001, 161, 1140-1144; J. Cardiovasc. Pharmacol. 1998, 31 (suppl. 2) S1-S4; J. Hypertens. 1998, 16, 545-51; Blood. Press. 2001, 2 (Suppl.) 6-12; Am. J. Hypertens, 2001, 14, (Pt. 2), 231S-236S]. Since hypertension is one of the few major risk factors for future cardiovascular diseases including heart failure, kidney failure, stroke and others, there exists a significant unmet medical need for an antihypertensive drug that is effective across a wide variety of patients as a single therapy and in combination with diuretics or calcium channel antagonists, angiotensin converting enzymes or renin inhibitors.

The endogenous peptides endothelin 1 (ET-1) and angiotensin II (Ang-II) are powerful vasoconstrictors and mitogens, and both peptides have been implicated in the pathogenesis of hypertension, pulmonary arterial hypertension and cardiovascular disease [Yanagisawa M, et al. A novel potent vasoconstrictor peptide produced by vascular endothelial cells. Nature, 1988, 322, 411-415; J. Med. Chem. 1996, 39, 626-629; J. Cardiovas. Pharmacol. 1990, vol 5 (Suppl. 3), pp S1-S5]. Elevated levels of ET-1 increase the production and vasoconstrictive action of Ang-II and elevated levels of Ang-II enhance the production and vasocontrictive effect of ET-1, thus creating a positive dual-feedback mechanism and an excellent target for treating hypertension [Hypertension 1992, 19, 753-757; Biochim. Biophys. Acta 1993, 1178, 201-206].

There exists significant evidence that a novel approach of simultaneous antagonism of both the receptors $ET_A$ (ET-1 receptor type A) and $AT_1$ (Ang-II receptor type 1) can produce a larger reduction in blood pressure and added cardiovascular benefit than antagonizing either system individually. Recent animal studies in a canine model of renovascular hypertension, the combination of an $AT_1$ receptor antagonist (Losartan) with a $ET_A/ET_B$ mixed antagonist (Bosentan) produced a 40 mmHg reduction in mean arterial blood pressure, compared to a 20 mmHg decrease with Losartan alone [J. Hypertens. 1998, 16, 835-841]. In another animal study, using rat model of hypertension and heart failure, the combination of Losartan with an $ET_A$ receptor antagonist (LU-135252) showed synergistic effect in lowering blood pressure, heart weight, and mortality levels to those of the non-hypertensive controls [Hypertension 2000, 35, (4) 992-997]. Synergistic beneficial effects of dual $AT_1$ and $ET_A$ receptor antagonism have been demonstrated in several other animal models of hypertension such as in DOCA-salt rats, spontaneously hypertensive rats (SHRs), and diabetic rats [Br. J. Pharmacol. 1995, 116, 2237-2244; J. Cardiovasc. Pharmacol. 2000, 36, S337-S341. Thus, it is envisioned that combined dual ET and $AT_1$ receptor antagonism in humans could be more effective than current therapies for treating hypertension, pulmonary hypertension and other diseases regulated directly and indirectly with the endogenous vasoconstrictor peptides endothelin and angiotensin II. Endothelin and endothelin receptors are known to play a critical role in the pathophysiology of cancer including prostate, lung, breast, colon, ovarian, and kidney cancer. Endothelin receptors $ET_A$ and $ET_B$ appear to regulate tumor progression by several mechanisms, including cell proliferation, inhibition of apoptosis, angiogenesis, matrix remodeling, and bone deposition in skeletal metastases through activation of osteoblasts [Nelson J, Bagnato A, Battistini B, Nisen P. The endothelin axis: emerging role in cancer. Nat Rev Cancer. 2003, 3, 110-116; Bagnato A, Spinelli F. Emerging role of endothelin-1 in tumor angiogenesis. Trends Endocrinol Metab. 2002, 14, 44-50; Rosano L, Varmi M, Salani D, et al. Endothelin-1 induces tumor proteinase activation and invasiveness of ovarian carcinoma cells. Cancer Res. 2001, 61, 8340-8346].

Activation of $ET_A$ by endothelin-1 (ET-1) promotes tumor growth and progression by inhibiting apoptosis, synergizing with other growth factors to cause cell proliferation, and by stimulating the production of the key angiogenic factor VEGF in response to hypoxia [Bagnato A, Spinelli F. Emerging role of endothelin-1 in tumor angiogenesis. Trends Endocrinol Metab. 2002, 14, 44-50]. $ET_A$ activation also induces matrix-degrading enzymes, such as matrix metalloproteinases and urokinase plasminogen activator, which have important roles in tissue remodeling and tumor metastasis [Rosano L, Varmi M, Salani D, et al. Endothelin-1 induces tumor proteinase activation and invasiveness of ovarian carcinoma cells. Cancer Res. 2001, 61, 8340-8346] In neuronal cells, ET-1/$ET_A$ binding is involved in nociceptive effects associated with cancer bone metastasis and remodeling, and thus may be associated with bone pain in patients with bone metastasis [Peters C M, Lindsay T H, Pomonis J D, et al. Endothelin and the tumorigenic component of bone cancer pain. Neuroscience. 2004, 126, 1043-1052].

In contrast, activation of $ET_B$ by ET-1 promotes vasodilation and induces apoptosis in human cancer cells [Okazawa M, Shiraki T, Ninomiya H, Kobayashi S, Masaki T. Endothelin-induced apoptosis of A375 human melanoma cells. J. Biol. Chem. 1998, 273, 12584-12592]. In addition, following activation of $ET_B$, the endothelin-$ET_B$ complex is internalized, which in turn decreases the concentration of endothelin in the blood.

Endothelins (ET) family comprises three 21-amino acid peptides (ET-1, ET-2, and ET-3) of which ET-1 is the most biologically relevant to kidney function in health and disease. While ET-1 was originally reported as an endothelium-derived vasoconstrictor [Yanagisawa M, et al. A novel potent vasoconstrictor peptide produced by vascular endothelial cells. Nature, 1988, 322, 411-415], It is now clear that the endogenous ET peptide hormone is produced by and acts upon virtually every cell type in the body [Barton M, et al. Endothelin: 20 years from discovery to therapy. Can J. Physiol. Pharmacol. 2008, 86, 485-98]. Endothelin is an important regulators of kidney function in health and disease [Barton M, et al. Endothelin: 20 years from discovery to therapy. Can J. Physiol. Pharmacol. 2008, 86, 485-98; Kohan D E, et al. Regulation of blood pressure and salt homeostasis by endothelin. Physiol. Rev. 2011, 91, 1-77]. Abnormal activation of the renal endothelin cascade promotes chronic kidney disease (CKD) progression. Endothelin-1 elevates angiotensin-II (A-II) levels [Kawaguchi H, et al. Endothelin stimulates angiotensin I to angiotensin II conversion in cultured pulmonary artery endothelial cells. J. Moll. Cell Cardiol. 1990, 22, 839-42] and in turn, A-II activates renal ET-1 production [Barton M, et al. Angiotensin II increases vascular and renal endothelin-1 and functional endothelin converting enzyme activity in vivo: role of $ET_A$ receptors for endothelin regulation. Biochem. Biophys. Res. Commun. 1997, 238, 861-865] thereby creating a positive feedback loop. ET-1 is involved in the priming effect of acute ischemic renal injury on development of CKD. This effect of ET-1 leading to chronic kidney disease can be prevented by blocking the endothelin receptor-A, $ET_A$ [Zager R A, et al. Progressive endothelin-1 gene activation initiates chronic/end-stage renal disease following experimental ischemic/reperfusion injury. Kidney Int. 2013, 84, 703-12]. Evidence for a direct role of endothelin (ET-1) in chronic kidney disease (CKD) was reported by Hocher et al. in transgenic mice studies, wherein it was found that mice systemically overexpressing the human preproendothelin gene developed glomerulosclerosis in the absence of systemic hypertension [Hocher B, et al. Endothelin-1 transgenic mice develop glomerulosclerosis, interstitial fibrosis, and renal cysts but not hypertension. J. Clin. Invest. 1997, 99, 1380-1389]. In another independent study, it was reported that treatment by an endothelin receptor antagonist in a rat renal mass reduction model resulted in substantial reduction in proteinuria and glomerulosclerosis [Benigni A, et al. A specific endothelin subtype A receptor antagonist protects against injury in renal disease progression. Kidney Int. 1993, 44, 440-444].

Additional studies have supported the findings that endothelin contributes to renal disease progression both under hypertensive and normotensive conditions [Speed J S, et al. Endothelin, kidney disease, and hypertension. Hypertension. 2013, 61, 1142-1145].

Focal segmental glomerulosclerosis (FSGS) is a renal disease characterized by injury to the glomerular filtration barrier [Meyrier A, et al. Mechanism of disease: focal segmental glomerulosclerosis. Nature Clin. Prac. Nephrol. 2005, 1, 44-54] Urinary excretion of endothelin-1 (ET-1) is increased in primary FSGS patients and glomerular endothelin-1 expression is enhanced in experimental FSGS [Fligny C, et al. Endothelin and podocyte injury in chronic kidney disease. Contrib. Nephrol. 2011, 171, 120-138] Podocyte-specific mechanisms have been invoked for the development of FSGS [Floege J, et al. Age-related glomerulosclerosis and interstitial fibrosis in Milan normotensive rats: a podocyte disease. Kidney Int. 1997, 51, 230-243; Zhu L, et al. Activation of RhoA in podocytes induces focal segmental glomerulosclerosis. J. Am. Soc. Nephrol. 2011, 22, 1621-1630].

Aging is associated with spontaneous development of FSGS in humans and rodents [Floege J, et al. Age-related glomerulosclerosis and interstitial fibrosis in Milan normotensive rats: a podocyte disease. Kidney Int. 1997, 51, 230-243], which is attributed to increased renal endothelin-1 expression [Hartleben B, et al. Autophagy influences glomerular disease susceptibility and maintains podocyte homeostasis in aging mice. J. Clin. Invest. 2010, 120, 1084-1096; Lattmann T, et al. Anatomically distinct activation of endothelin-3 and the L-arginine/nitric oxide pathway in the kidney with advanced aging. Biochem. Biophys. Res. Commun. 2005, 327, 234-241.

Studies in rodents with aging-FSGS demonstrated that treatment for one month with endothelin receptor-A ($ET_A$) antagonists showed blood pressure-independent regression of FSGS, proteinuria and glomerular basement membrane hypertrophy, podocyte morphology modification and reduced podocyte autophagy [Ortmann J, et al. Role of podocytes for reversal of glomerulosclerosis and proteinuria in the aging kidney after endothelin inhibition. Hypertension. 2004, 44, 974-981] Treatment with endothelin receptor antagonist significantly down-regulated $p21^{waf1/cip1}$, a cell cycle inhibitor and inhibitor of cell growth that contributes to chronic kidney disease (CKD) in FSGS animals [Ortmann J, et al. Role of podocytes for reversal of glomerulosclerosis and proteinuria in the aging kidney after endothelin inhibition. Hypertension. 2004, 44, 974-981; Di Cunto F, et al. Inhibitory function of p21 Cip1/WAF1 in differentiation of primary mouse keratinocytes independent of cell cycle control. Science. 1998, 280, 1069-1072; Megyesi J, et al. The lack of a functional p21 (WAF1/CIP1) gene ameliorates progression to chronic renal failure. Proc. Natl. Acad. Sci. USA. 1999, 96, 10830-5].

Blockade of endothelin receptors (e.g. by endothelin $ET_A$ and $ET_A/ET_B$ receptor antagonists) has been shown to ameliorate renal injury and fibrosis at multiple levels. Both preclinical and early clinical trial evidence suggest that endothelin receptor antagonists have shown incredible potential for therapeutic benefit for the treatment of various forms of renal diseases as antiproteinuric and nephroprotective drugs for diabetic nephropathy, hypertensive nephropathy, IgA nephropathy (IgAN), focal segmental glomerulosclerosis (FSGS), and other forms of acute and chronic kidney disease (CKD) [Kohan D E, et al. Endothelin and Endothelin Antagonists in Chronic Kidney Disease. Kidney Int. 2014, 86(5), 896-904].

Compounds that specifically inhibit the binding of endothelin to its receptors are believed to block the physiological effects of endothelin and are useful in the treatment of patients with endothelin related diseases. The novel deuterated compounds of the present invention are useful as small molecule endothelin receptor antagonists.

DETAILED DESCRIPTION OF THE INVENTION

The present invention relates to novel deuterium-enriched substituted phenoxy-(3, 4-methylenedioxy)phenylacetic acid and acylsulfonamide derivatives of general structural formula I,

I

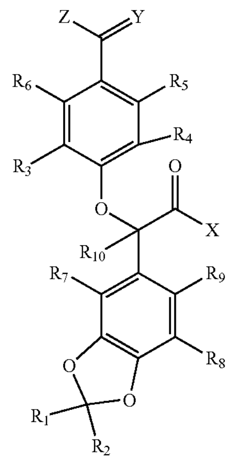

their optically active or optically pure enantiomers and diastereomers, and pharmaceutically acceptable salts thereof, wherein:

$R_1$ and $R_2$ are H (Hydrogen), D (Deuterium), F (Fluorine);

$R_3$ and $R_4$, are independently selected from H, D, $CH_2$—$CH_2$—$CH_3$, $CH_2$—$CH_2$—$CD_3$, $CH_2$-$CD_2$-$CD_3$, $CD_2$-$CD_2$-$CD_3$, $CD_2$-CHD-$CHD_2$, $CH_2$—CHD-$CH_2D$, $CD_2$-$CD_2$-O—$CD_2CD_3$, $CH_2CH_2OCD_3$, $CH_2CH_2OCH_2CH_3$; $CH_2CH_2OCD_2CD_3$; $CD_2CD_2OCH_2CH_3$;

$R_5$, $R_6$, $R_7$, $R_8$, $R_9$, and $R_{10}$, are independently D, H;

X is OD, OH, $O^-K^+$, $NHSO_2$—$(C_6H_4)$-4-i-Pr, $NDSO_2$—$(C_6H_4)$-4-i-Pr, $N^-K^+SO_2$—$(C_6H_4)$-4-i-Pr, $NDSO_2$—$(C_6D_4)$-4-i-Pr-$d_7$, $NDSO_2$—$(C_6H_4$-$d_2)$-4-i-Pr-$d_7$, $NDSO_2$—$(C_6H_4)$-4-i-Pr-$d_7$, $NDSO_2$—$(C_6H_4)$-4-i-Pr-$d_1$, $NDSO_2$-4-$(C_6H_4)$-i-Pr-$d_6$, $NDSO_2$—$(C_6H_4)$-4-i-Pr-$d_3$, $NHSO_2$—$(C_6H_4)$-4-iPr-$d_1$, $NHSO_2$—$(C_6H_4)$-4-iPr-$d_3$, $NHSO_2$—$(C_6H_4)$-4-iPr-$d_4$, $NHSO_2$—$(C_6H_4)$-4-iPr-$d_6$ $NHSO_2$—$(C_6H_4)$-4-iPr-$d_7$, OH, $O^-K^+$, $O^-Na^+$, $O^-Li^+$, $OCD_3$, $OCD_2CD_3$, $OCD_2CD_2CD_3$;

Y is O, $D_2$, DH, HH;

Z is OD, OH, $O^-K^+$, $O^-Na^+$, $O^-Li^+$, $OCD_3$, $OCD_2CD_3$; $OCD_2CD_2CD_3$,

The compounds of structural Formula I and pharmaceutically acceptable salts and combinations thereof, have selective antagonist activity for endothelin receptors and/or dual or combined antagonist activity for endothelin and angiotensin II receptors, and are therefore useful in the treatment of diseases mediated by endothelin and/or angiotensin-II and their receptors including pulmonary arterial hypertension, pulmonary hypertension associated with chronic obstructive pulmonary disease (COPD), right ventricular hypertrophy, pulmonary vascular remodeling, lung fibrosis, hypertension, left ventricular hypertrophy, congestive heart failure, arrhythmia, arterial fibrillation, digital ulcers, idiopathic pulmonary fibrosis, idiopathic pulmonary hypertension, acute kidney disease, chronic kidney disease, renal failure, cyclosporin-induced renal failure, IgA nephropathy (IgAN), focal segmental glomerulosclerosis (FSGS), diabetic nephropathy, scleroderma, digital ulcers, prostate cancer, breast cancer, lung cancer, ovarian cancer, colon cancer, kidney cancer, arteriosclerosis, myocardial infarction, angina pictoris, cerebral and cardiac ischemia, post-ischemic renal failure, stroke, vasospasm, Raynaud's disease, asthma, diabetes, obesity, erectile dysfunction, benign prostatic hyperplasia, endotoxic shock, endotoxin-induced, multiple organ failure, sepsis, and inflammatory bowel diseases. Crohn's disease and ulcerative colitis.

Deuterium (D or $^2H$) is a stable isotope non-radioactive isotope of hydrogen (H) and has an atomic weight of 2.0144. Hydrogen occurs naturally as a mixture of the isotopes $^1H$, D ($^2H$), and T ($^3H$ or tritium) and the natural abundance of deuterium is 0-015%. One of ordinary skill in the art recognizes that in all compounds containing H atom, H actually represents a mixture of H and D, with about 0-015% of D. So, compounds with a level of D that has been enriched to be greater than its natural abundance of 0.015%, should be considered unnatural and as a result novel as compared to their corresponding non-enriched counterparts.

The carbon-hydrogen bonds contain a naturally occurring distribution of hydrogen isotopes, namely $^1H$ or protium (about 99.9844%), $^2H$ or deuterium (D) (about 0.0156%), and $^3H$ or tritium (in the range between about 0.5 and 67 tritium atoms per $10^{18}$ protium atoms). Higher levels of deuterium incorporation produce a detectable Kinetic Isotope Effect [Werstiuk, N. H.; Dhanoa, D. S.; Timmins, G. Can J. Chem. 1979, 57, 2885; Werstiuk, N. H.; Dhanoa, D. S.; Timmins, G. Can J. Chem. 1983, 61, 2403], that could improve the pharmacokinetic, pharmacologic and/or toxicologic parameters of compounds of formula I in comparison to compounds having naturally occurring levels of deuterium and their corresponding hydrogen (protium) analogs.

Suitable modifications of certain carbon-hydrogen bonds into carbon-deuterium bonds may generate novel substituted compounds of structural formula I with unexpected and non-obvious improvements of pharmacological, pharmacokinetic and toxicological properties in comparison to the non-isotopically enriched compounds. This invention relies on the judicious and successful application of chemical kinetics to drug design. Deuterium incorporation levels in the compounds of the invention are significantly higher than the naturally-occurring levels and are sufficient to induce at least one substantial improvement as described herein. All percentages given for the amount of deuterium present are mole percentages.

"Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%.

It can be a significant synthetic challenge to produce 100% deuterium at a specific site of a compound. When 100% deuteration is recited or a deuterium atom is specifically shown in a chemical structure of a compound, a small amount of deuterium may still be present. Higher levels of deuterium content in a compound can be produced either by Hydrogen-Deuterium (H-D) exchange or by synthesizing the compound for specific deuteration. The H-D exchange is readily achieved in case of H atoms attached to heteroatoms for example in cases of carboxylic acids (COOH), sulfonamides ($SO_2NH_2$, $CONHSO_2$-aryl, $CONHSO_2$-alkyl), alcohols (OH), basic amines ($NH_2$), etc. However, these incorporated D attached to heteroatoms (O, N, S) etc, readily revert back to H upon exposure to water or any acidic compounds containing H atoms. The preferred deuterium containing compounds are the ones which contain deuterium directly attached to carbon atoms of the structure of the compounds of this invention.

In some embodiments, the deuterium enrichment in the compounds of the present invention is greater than 4%, 5%, 6%, 7%, 8%, 9% or 10%. In other embodiments, the deuterium enrichment in the compounds of the present invention is greater than 20%. In further embodiments, the deuterium enrichment in the compounds of the present invention is greater than 50%. In some embodiments, the deuterium enrichment in the compounds of the present invention is greater than 70%. In some embodiments, the deuterium enrichment in the compounds of the present invention is greater than 90%.

This invention is concerned with deuterium-enriched compounds of structural formula I, derivatives thereof and pharmaceutically acceptable salts and compositions thereof, This invention is concerned with compounds of the general structural formula I, deuterium-enriched compounds of formula I, their enantiomers, atropisomers, diastereomers, pharmaceutical acceptable salts and metabolites thereof,

I

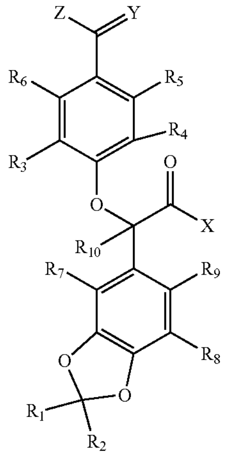

wherein, $R_1$ and $R_2$ are D (Deuterium), H or F;

$R_3$ and $R_4$, are independently selected from D, $CD_2$-$CD_2$-$CD_3$, $CD_2$-CHD-$CHD_2$, $CD_2$-$CD_2$-O—$CD_2CD_3$, H; $CH_2CH_2CH_3$, $CH_2CH_2OCD_3$, $CH_2CH_2OCH_2CH_3$; $CH_2CH_2OCD_2CD_3$; $CD_2CD_2OCH_2CH_3$;

$R_5$, $R_6$, $R_7$, $R_8$, $R_9$, and $R_{10}$, are independently D, H;

X is OD, OH, $O^-K^+$, $NHSO_2$—$(C_6H_4)$-4-i-Pr, $NDSO_2$—$(C_6H_4)$-4-i-Pr, $N^-K^+SO_2$—$(C_6H_4)$-4-i-Pr, $NDSO_2$—$(C_6D_4)$-4-i-Pr-$d_7$, $NDSO_2$—$(C_6H_4(d_2))$-4-i-Pr-$d_7$, $NDSO_2$—$(C_6H_4)$-4-i-Pr-$d_7$, $NDSO_2$—$(C_6H_4)$-4-i-Pr-$d_1$, $NDSO_2$-4-$(C_6H_4)$-i-Pr-$d_6$, $NDSO_2$—$(C_6H_4)$-4-i-Pr-$d_3$, $NHSO_2$—$(C_6H_4)$-4-iPr-$d_1$, $NHSO_2$—$(C_6H_4)$-4-iPr-$d_3$, $NHSO_2$—$(C_6H_4)$-4-iPr-$d_4$, $NHSO_2$—$(C_6H_4)$-4-iPr-$d_6$, $NHSO_2$—$(C_6H_4)$-4-iPr-$d_7$, OH, $O^-K^+$, $O^-Na^+$, $O^-Li^+$, $OCD_3$, $OCD_2CD_3$, $OCD_2CD_2CD_3$;

Y is O, $D_2$, DH;

Z is OD, OH, $O^-K^+$, $O^-Na^+$, $O^-Li^+$, $OCD_3$, $OCD_2CD_3$; $OCD_2CD_2CD_3$,

The reaction scheme conceptualized and used for the synthesis of compounds and intermediates of this invention are general. It will be understood by those skilled in the art of organic synthesis that one or more functional groups present in a given compound of the invention may render the molecule incompatible with a particular synthetic sequence. In such a case an alternative synthetic route, an altered order of steps or a strategy of protection and deprotection may be employed. The reactions are performed in a solvent appropriate to the reagents and materials employed and suitable for the transformation being effected. It is understood by those skilled in the art of organic synthesis that the functionality present on the reactants and reagents being employed should be consistent with the chemical transformations being conducted. Depending upon the reactions and techniques to be used optimal yields may require changing the order of synthetic steps or use of protecting groups followed by deprotection. In all cases the particular reaction conditions, including reagents, solvent, temperature and time, should be chosen so that they are consistent with the nature of the functionality present in the molecule.

The compounds useful in the novel method treatment of this invention form salts with various inorganic and organic acids and bases which are also within the scope of the invention. Such salts include alkali metal salts like sodium and potassium salts, ammonium salts, alkaline earth metal salts such as calcium and magnesium salts, salts with organic bases for example dicyclohexylamine salts, N-methyl-D-glucamine salts, salts with amino acids e.g., arginine, lysine, etc. In addition, salts with organic and inorganic acids may be prepared; e.g., HCl, HBr, $H_2SO_4$, $H_3PO_4$, methanesulfonic, toluenesulfonic, maleic, fumaric, camphorsulfonic acid.

The salts can be formed by conventional means, such as by reacting the free acid or free base forms of the product with one or more equivalents of the appropriate base or acid in a solvent or medium in which the salt is insoluble, or in a solvent such as water, which is then removed in vacuo or by freeze-drying or by exchanging the cations of an existing salt for another cation on a suitable ion exchange resin.

It will be appreciated that the compounds of general Formula I in this invention may be derivatized at functional groups to provide prodrug derivatives, which are capable of conversion back to the parent compounds in vivo. The concept of prodrug administration has been extensively reviewed [e.g. A. A. Sinkula in Annual Reports in Medicinal Chemistry, Vol 10, R. V. Heinzelmann, E D., Academic Press, New York, London, 1975, Ch 13, pp 306-326; H. Ferres, Drugs of Today, Vol 19, 499-538, 1983, and J. Med. Chem., 18, 172, 1975]. Examples of such prodrugs include the physiologically acceptable and metabolically labile ester derivative, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminomethyl esters (e.g. 2-dimethylaminoethyl esters). Additionally, any ohysiologically acceptable equivalents of the compounds of general structural formula I, similar to the metabolically labile esters, which are capable of producing the parent compounds of general Formula I in vivo, are within the scope of this invention.

It will be further appreciated that the majority of compounds of general Formula I claimed herein are asymmetric and are produced as racemic mixtures of enantiomers and that both the racemic compounds and the resolved individual non-racemic enantiomers are considered to be within the scope of this invention. The compounds of the present invention may have various isomers including all stereoisomers of asymmetric atoms (enantiomers and diastereomers) and geometric, tautomeric or rotamers, and all isomers are considered to be part of the present invention. All processes used to prepare compounds of the present invention and intermediates made therein are considered to be part of the present invention. The racemic compounds of this invention may be resolved to provide individual enantiomers utilizing methods known to those skilled in the art of organic synthesis. For example, diastereoisomeric salts, esters or imides may be prepared from a racemic compound of the Formula I and a suitable optically active amine, amino acid, alcohol or the like. The diastereoisomeric salts, esters or imides are separated, isolated and purified. The optically active enantiomers are regenerated and the preferred enantiomer is the more potent isomer. The resolved enantiomers of the compounds of general Formula I, their pharmaceutically acceptable salts and their prodrug forms are also included within the scope of this invention.

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination.

"Pharmaceutically acceptable salts" refer to derivatives of the disclosed compounds wherein the parent compound is modified by making acid or base salts thereof. Examples of the pharmaceutically acceptable salts include, but not limited to, mineral or organic acid salts of the basic residues. The pharmaceutically acceptable salts include but not limited to HCl, HBr, HI, potassium (K), sodium (Na), calcium (Ca), magnesium (Mg), acetic, trifluoroacetic, citric, ascorbic, benzoin, methanesulfonic (mesylate), benzenesulfonic, bicarbonic, carbonic, ethane disulfonic, edetic, fumaric, maleic, lactic, malic, mandelic, gluconic, glutamic, glycolic, glycollyarsanilic, lauryl, hexylresorcinic, hydrabamic, hydroxymaleic, hydroxynaphthoic, isethionic, lactobionic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluenesulfonic, and p-bromobenzenesulfonic.

Synthesis

Preparation of compounds of structural formula I described below are general. It should be understood by those skilled in the art of chemical synthesis that some functional groups may not be compatible for certain synthetic routes and those cases may require appropriate changes including alternative starting materials, building blocks, intermediates, synthesis, synthetic methods process, appropriate sequence of synthetic steps, and compatible protection and deprotection strategy should be employed. The particular reaction conditions, such as reagents, solvents, temperature, and reaction time, should be used for conducting a synthetic reaction consistent with the nature of the functionality of the reactant and products involved.

One of the key precursors ethyl 4-hydroxybenzoate 5, is prepared starting from 4-aminophenol (or 4-hydroxyaniline) 2 as shown in Scheme 1. Microwave heating at 180° C. of a mixture of 2, $D_2O$ and concentrated HCl (1 equivalent) for 30 min after basic workup yields 2,5-dideuteated-4-hydroxyaniline 3. The deuterated aniline derivative 3 is converted into its nitrile derivative 4 via its diazonium salt which is prepared by treatment of 3 with sodium nitrite ($NaNO_2$) in aqueous HCl at 0°-5° C. The low temperature 0°-5° C. is maintained by using ice-salt mixture bath for the reaction flask. The diazonium ion obtained as such in situ is treated with cuprous cyanide (CuCN) at 0° C. for an hour and then allowed to warm up to room temperature to produce 4-hydroxybenzonitrile 4. Hydrolysis of 4 with HCl or $H_2SO_4$ in EtOH or MeOH produces the corresponding deuterated 4-hydroxybenzoate 5 as its ethyl or methyl ester.

Alternatively 5 is also prepared from 2a, the t-butyldimethylsilyl (TBDMS) derivative of 2, by its deuteration followed by diazonium salt formation and CuCN substitution to its nitrile followed by its acidic hydrolysis and deprotection of the TBDMs group as shown in Scheme 1. A mixture of 2a, $D_2O$ and 1 equiv of conc HCl is heated in a microwave for half hour to produce its dideuteated analog 3a which is then converted to its diazonium salt by its treatment with $NaNO_2$ and HCl at 0° C. Treatment of the diazonium salt at 0-5° C. with CuCN gives the corresponding nitrile derivative 4a. Acidic hydrolysis of 4a with HCl or $H_2SO_4$ in alcoholic solvent (EtOH or MeOH) yields its ester, which is treated with tetra(n-butylammonium)fluoride ($nBu_4NF$) in tetrahydrofuran (THF) to produce deuterated 5.

Scheme 1

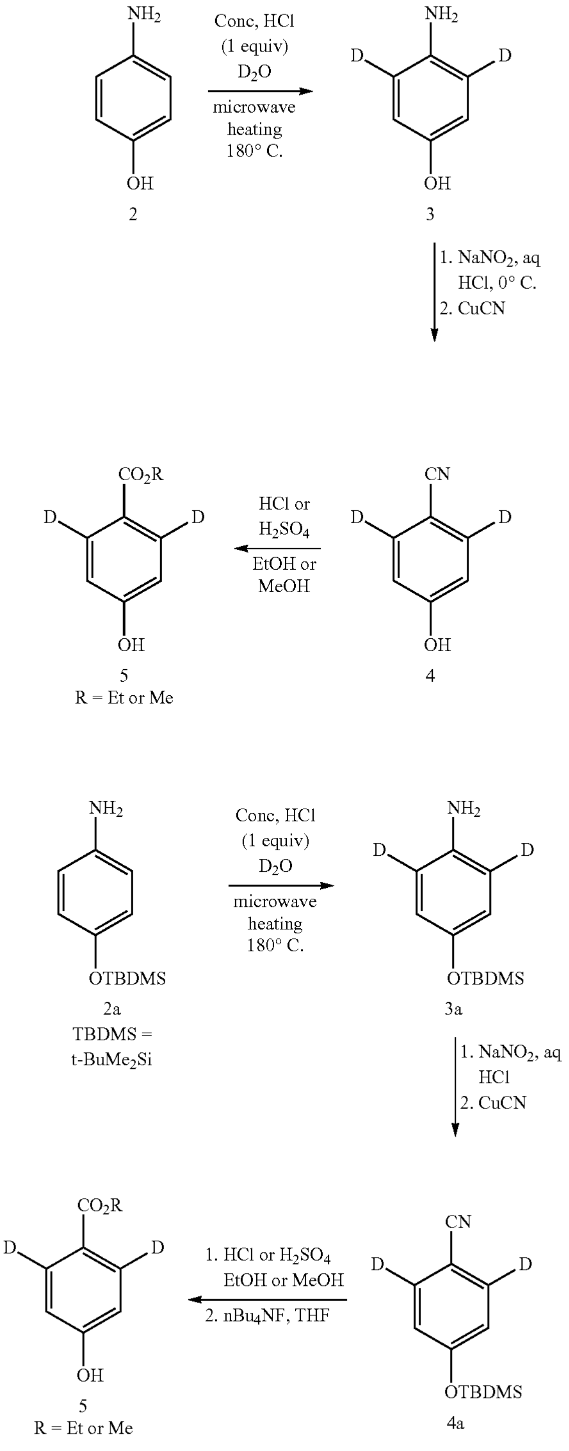

2 3 4 5 R = Et or Me 2a TBDMS = t-BuMe2Si 3a 4a 5 R = Et or Me

Deuterated isomer 8 (Methyl 3,5-dideuterated-4-hydroxybenzoate) of 5 is prepared from methyl 4-aminobenzoate 6 which upon heating its mixture with $D_2O$ and 1 equiv of conc HCl in a microwave at 180° C. for half hour gives 3,5-dideuterated-aminobenzoate 7. Treatment of 7 with $NaNO_2$ in HCl at 0°-5° C. results in the formation of its diazonium salt in situ which upon its reaction with cuprous oxide in water or potassium hydroxide (KOH) yields 8.

Scheme 2

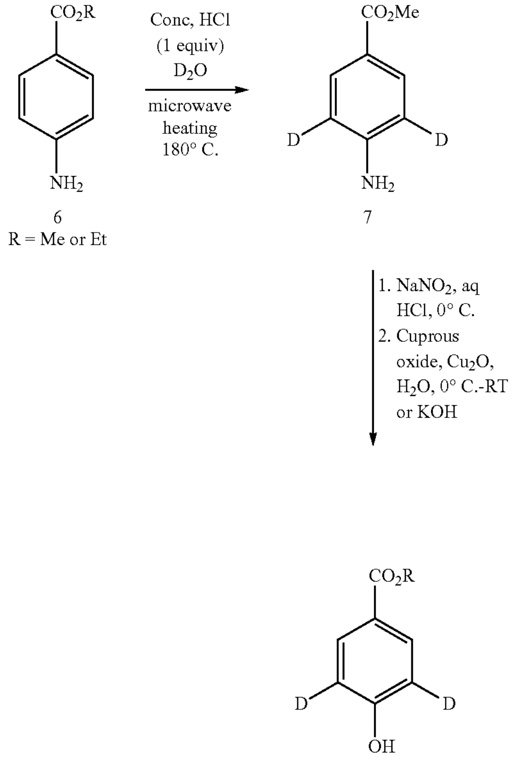

6
R = Me or Et

7

8
R = Me or Et

Deuterated, partially deuterated or undeuterated methyl or ethyl 4-hydroxybenzoate 9 (which is prepared as described above and illustrated for the preparation of 5 and 8 in scheme 1 and 2) is alkylated with partial or fully deuterated or undeuterated allyl bromide 10 (or allyl chloride, or allyl iodide, or allyl tosylate or allyl mesylate) by refluxing the mixture with potassium carbonate in acetone for 8 to 18 h as shown in scheme 3 (Dhanoa, D. S. et. al., *J. Med. Chem.* 1993, 36, 3788-3742). After completion of the reaction, it is quenched with cold water. Then, the reaction is diluted with methylene chloride and washed with brine. The organic phase is dried over anhydrous magnesium sulfate, filtered and concentrated under vacuum. The residue obtained as such is purified by flash chromatography (silica gel, ethyl acetate hexanes) to isolate purified alkylated 11 as illustrated in scheme 3. Heating of 11 in dichlorobenzene at 185° C. for 8 hours affords 12 via the claisen rearrangement, which is purified by flash column chromatography over silica gel using gradient mixture of ethyl acetate and hexanes as the eluent. Catalytic hydrogenation of 12 using palladium on carbon (Pd/C) or using $H_2$ or deuterium $D_2$ in methanol yields 13. Alkyl side chain (n-propyl) in the advanced intermediate 13 (R=H) is readily deuterated using catalytic hydrogenation in the presence of deuterated water and heat ($H_2$, 10% Pd/C, $D_2O$, 160° C.) to yield perdeuterated propyl ($d_7$) intermediate compound 13 (R=D) in scheme 3. The catalyst is removed by filtering the diluted reaction mixture through celite plug. Alkylation of 13 with the appropriately deuterated alkyl α-bromophenylacetate ester 14 (and/or hydrogen derivative in which both $R_1$ and $R_2$ are hydrogen atoms in scheme 3) using cesium carbonate in anhydrous N,N-dimethylformamide ($Cs_2CO_3$/DMF) solution and stirring the resulting reaction mixture for 4 hours produces the alkylated product 15, the diester as shown in scheme 3. Alternatively, refluxing a reaction mixture of phenol 13 with ethyl α-bromophenylacetate ester 14 and potassium carbonate in acetone ($K_2CO_3$/acetone) overnight also gives the alkylated product 15 after purification by flash column chromatography using silica gel and mixture of solvents, ethyl acetate and hexanes. The preparation of 14 is illustrated in scheme 6. Deuterated derivatives of 3,4-methylenedioxyphenyl acetic esters, 15, is saponified using aqueous sodium hydroxide (NaOH) solution in methanol for a short period of time 0.5 h-1 h to produce the carboxylic acid ester 16 as illustrated in scheme 3. Substituted phenoxyphenyl acetic acid 16 is converted into its corresponding acylsulfonamide 18 via acylimidazole as intermediate using carbonyldiimidazole (CDI) in THF.

Scheme 3

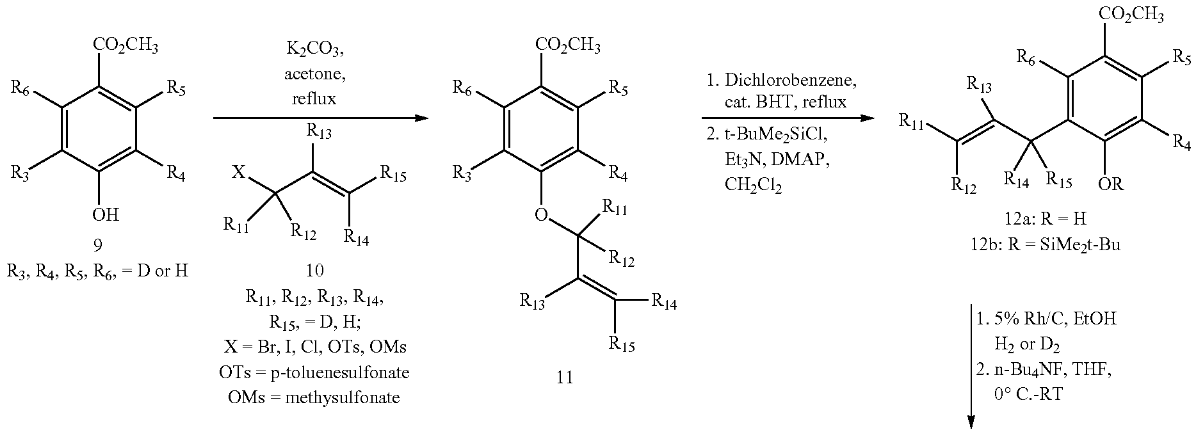

9
$R_3$, $R_4$, $R_5$, $R_6$, = D or H

10
$R_{11}$, $R_{12}$, $R_{13}$, $R_{14}$,
$R_{15}$, = D, H;
X = Br, I, Cl, OTs, OMs
OTs = p-toluenesulfonate
OMs = methysulfonate

11

12a: R = H
12b: R = $SiMe_2$t-Bu

-continued

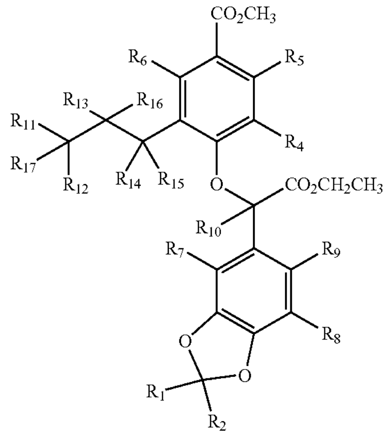

15
$R_1$ = D or F
$R_2$ = D or F;
$R_{10}$ = D or H

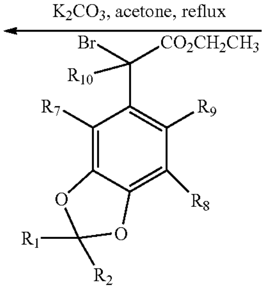

14
$R_1$ = D or F; $R_2$ = D or F
$R_7$, $R_8$, $R_9$ = D or H
$R_{10}$ = D or H

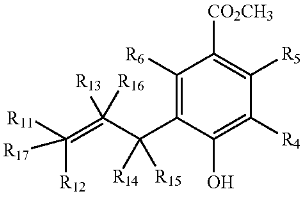

13
$R_{16}$ = D or H
$R_{17}$ = D or H

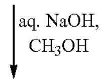

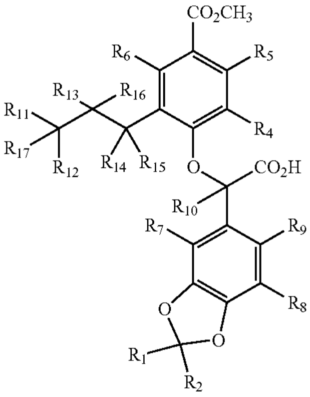

16
$R_1$ = D or F
$R_2$ = D or F

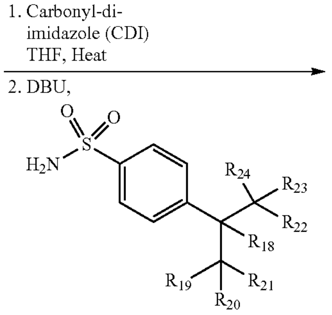

17
$R_{18}$ = D or H
$R_{19}$, $R_{20}$, $R_{21}$,
$R_{22}$, $R_{23}$, $R_{24}$ =
D or H

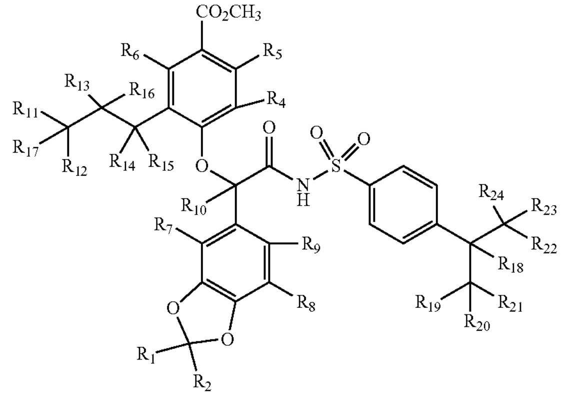

18
$R_1$ = D or F
$R_2$ = D or F

The mixture of 16 and CDI in THF is heated at 50-55° C. for 1 hour and then treated with a mixture of appropriately deuterated or undeuterated 4-isopropylbenzene sulfonamide 17 and the base diazabicycloundecene (DBU) in THF and heated at 55° C. for 3 hours to afford the desired acylsulfonamide 18. The sulfonamide 17 is prepared from 4-isopropylbenzenesulfonyl chloride by treating it with ammonium hydroxide ($NH_4OH$) as illustrated in scheme 6 and scheme 9.

Saponification of 16 with aq NaOH in methanol for a longer period of time yields the dicarboxylic acid 19 as shown in scheme 4. The reaction is followed by thin layer chromatography (TLC) to ensure complete conversion of 16 to the diacid 19.

Potassium salt 20 of the mono acidic carboxylic ester 16 is prepared by treatment of 16 with aqueous solution of sodium bicarbonate ($KHCO_3$) or KOH in methanol ($CH_3OH$). The dipotassium salt 21 of 16 is also prepared by its treatment with aqueous solution of KOH in methanol. The dipotassium salt 21 is also prepared by saponification of diester 15 with aqueous KOH solution in methanol. The saponification of the mono ester acid 16 with aqueous solution of KOH in methanol also yields the dipotassium salt 21 a shown in scheme 4.

Mono-potassium salt 22 of the acylsulfonamide is prepared selectively from the methyl ester sulfonamide 18 by treatment with potassium bicarbonate ($KHCO_3$) or KOH in methanol ($CH_3OH$) as shown in scheme 5. Saponification of 18 using aqueous solution of sodium hydroxide in methanol ($NaOH/CH_3OH$) produces the sulfonamide carboxylic acid derivative 23. Treatment of acylsulfonamide-carboxylic acid 23 with potassium hydroxide solution in methanol ($KOH/CH_3OH$) yields the dipotassium salt 24, which is also prepared from 22 by its saponification with aqueous solution of sodium hydroxide in methanol ($NaOH/CH_3OH$) followed by the treatment of the isolated acylsulfonamide-acid with potassium hydroxide solution in methanol ($KOH/CH_3OH$) as shown in Scheme 5.

Scheme 4
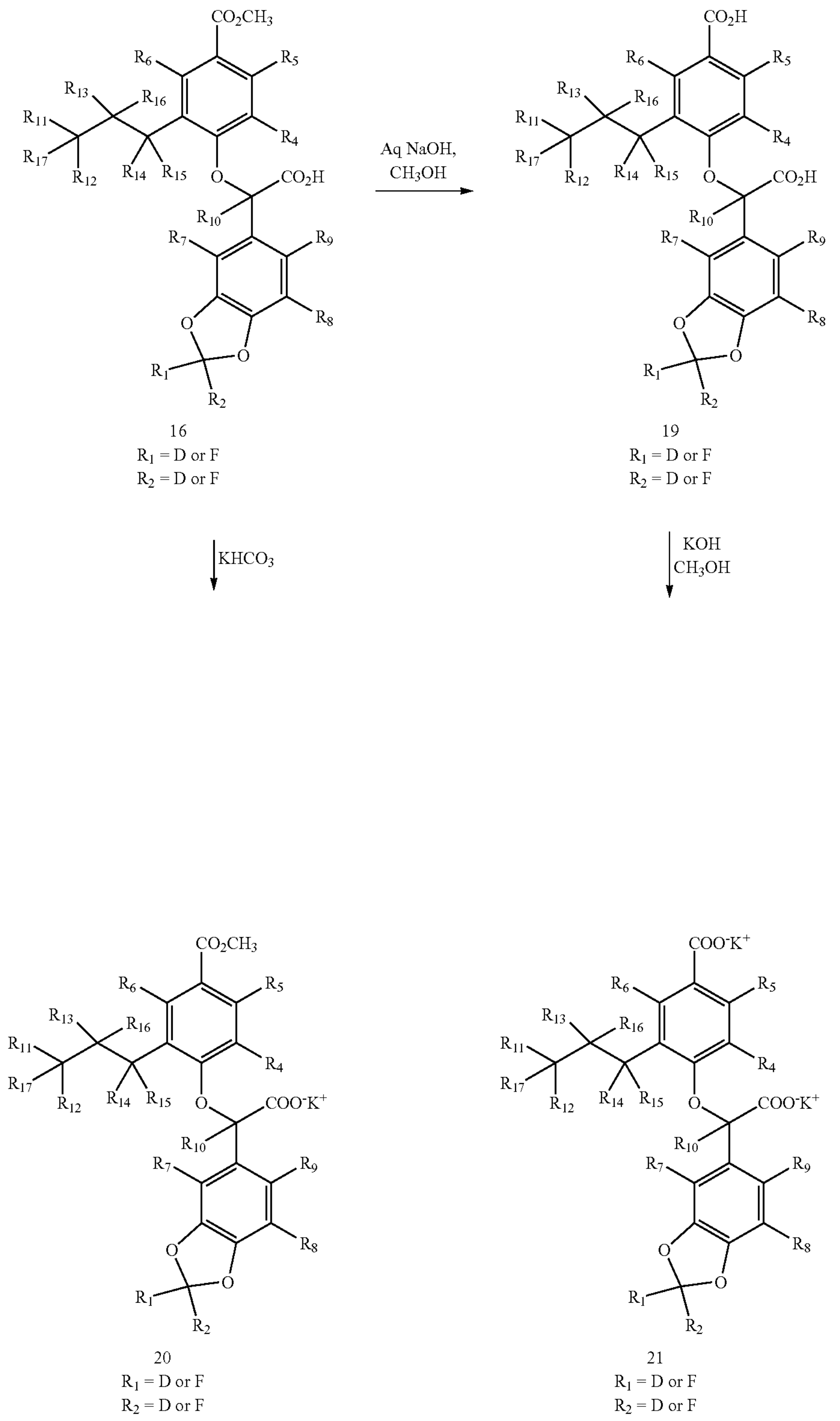
16
$R_1$ = D or F
$R_2$ = D or F
19
$R_1$ = D or F
$R_2$ = D or F
20
$R_1$ = D or F
$R_2$ = D or F
21
$R_1$ = D or F
$R_2$ = D or F Scheme 5

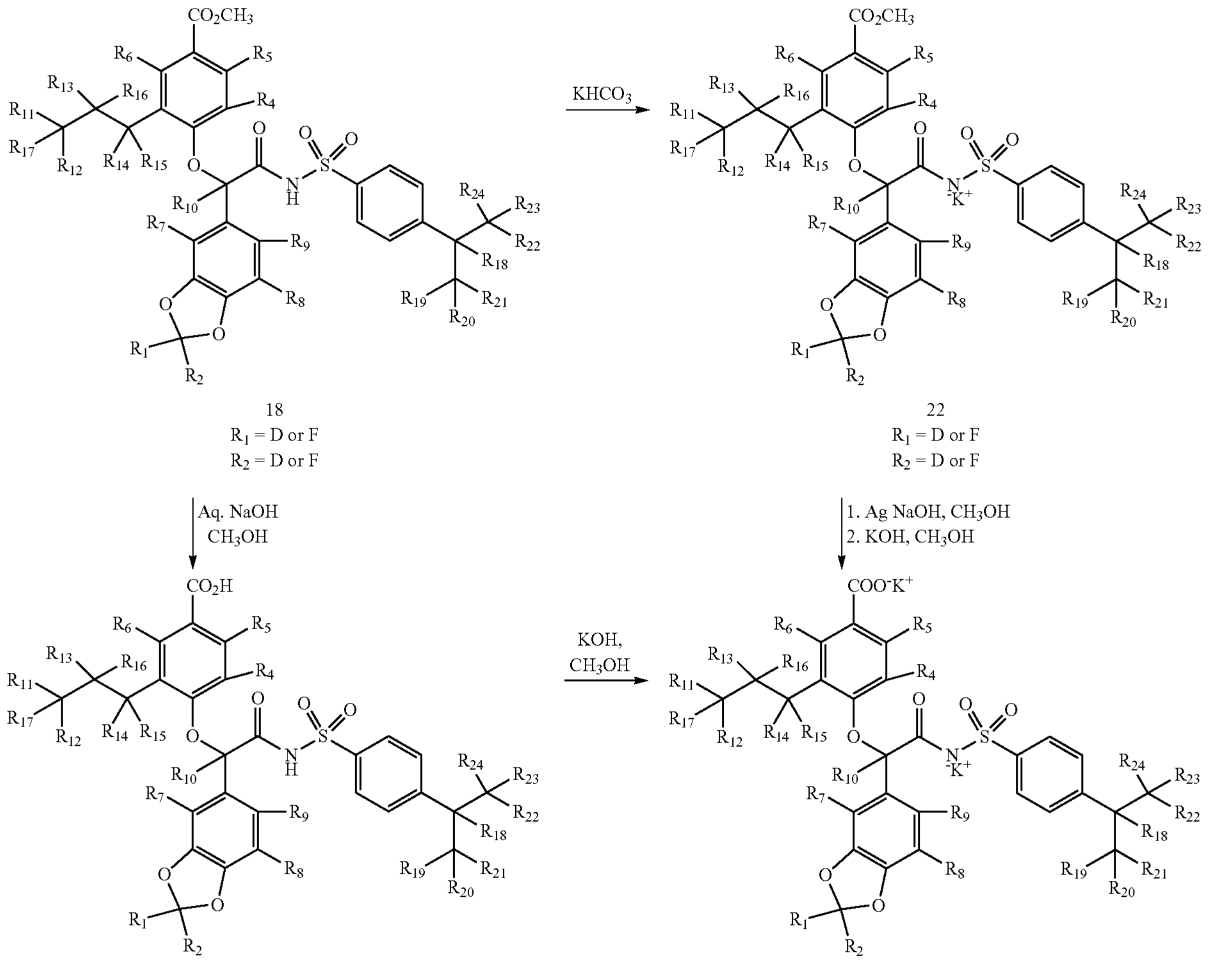

18
$R_1$ = D or F
$R_2$ = D or F

22
$R_1$ = D or F
$R_2$ = D or F

23
$R_1$ = D or F
$R_2$ = D or F

24
$R_1$ = D or F
$R_2$ = D or F

Preparation of the alkyl α-bromoester 14 from appropriate aldehydes and phenylacetic acids is illustrated in scheme 6. Alkylation of 3,4-dihydroxybenzaldehyde, 25 ($R_3$=H or D) with dideutero-dibromomethane ($CD_2Br_2$) in the presence of cesium carbonate ($Cs_2CO_3$) in DMF yields dideutero-3,4-methyledioxy-$d_2$-benzaldehyde 26a. The undeuterated 3,4-methylenedioxybenzaldehyde (in which case both $R_1$ and $R_2$ are H, hydrogen atoms) is readily and commercially available. Similarly the gemdifluoro-3,4-methylenedioxybenzaldehyde 26b is prepared by alkylation of 25 ($R_3$=H) with dibromo-difluoromethane ($CF_2B_2$) using $Cs_2CO_3$/DMF. The corresponding deuterated benzaldehydes 26 in which $R_3$ is deuterium are prepared in the same manner from 25-$d_1$ ($R_3$=D). Various methylenedioxybenzaldehydes 26 are converted to the corresponding trimethylsilyloxy nitriles 27 by treatment of 26 with trimethylsilyl cyanide (TMSCN) in the presence of catalytic amount of KCN and 18-crown-6 in dichloromethane for overnight. The reaction mixture is concentrated in vacuo and purified by flash column chromatography over silica gel and a mixture of ethyl acetate in hexane to yield 27. Treatment of 27 with gaseous HCl in the presence of anhydrous ethanol at 0° C. for an hour and then at room temperature for 24 hours affords the α-hydroxyesters 28. Hydroxyesters 28 are converted into the corresponding α-bromoesters 14 using phosphorus tribromide ($PBr_3$) in ether or alternatively, by treatment of 28 with carbon tetrabromide ($CBr_4$) and triphenylphosphine ($Ph_3P$) at 0° C. in methylene chloride gives the desired α-bromoesters 14 after quenching the reaction with methanol followed by concentration of the mixture in vacuo, and flash column chromatography over silica gel using a solvent mixture of ethyl acetate and hexanes as eluent. The esters 14 are also prepared alternatively by α-bromination of the corresponding 3,4-methylenedioxyphenylacetic esters 30 using N-bromosuccinimide (NBS) and a catalytic amount of AIBN (5-10 mole %) is refluxed in carbon tetrachloride for several hours until completion of the reaction. The product is isolated and purified by flash column chromatography using silica gel and ethyl acetate in hexane to give the ethyl α-bromophenylacetates 14. Esters 30 are also prepared from the corresponding 3,4-methylenedioxyphenylacetic ester 29 by their treatment with appropriate dibromo-methanes ($CD_2Br_2$ for 30a) and $CF_2Br_2$ for 30b) using $Cs_2CO_3$/DMF.

Undeuterated 4-isopropylbenzenesulfonamide is commercially available while its partially deuterated form is not available from commercial sources. The preparation of 2,6-dideuterated-4-isopropylbenzenesulfonamide 17 is illustrated in scheme 6. A mixture of 4-isopropylaniline 31 (2.7 g, 2 mmol), $D_2O$ (10 equiv) and 1 equivalent of conc. HCl is heated in a microwave at 180° C. for half hour. The mixture is quenched at room temperature cautiously with aqueous NaOH with stirring until the reaction mixture is basic. The product is extracted from aqueous phase with a mixture of solvents containing methylene chloride/ethyl acetate/ether. The organic extracts are combined, dried over anhydrous $Na_2SO_4$, filtered and then concentrated to yield 2,5-dideuterated-4-isopropylaniline 32 (2.1 g). Aniline 32 (2 g) is converted into its diazonium salt by treating with $NaNO_2$ (1.2 equiv) and HCl at 0° C., which is then treated with excess of $SO_2$ by bubbling through the reaction mixture in the presence of CuCl (1.2 equiv), AcOH and HCl at 0° C. for 4 hours and then at room temperature overnight. The reaction mixture is diluted with water, methylene chloride and ethyl acetate and stirred for few minutes. The organic phase is separated and dried over anhydrous $MgSO_4$, filtered and concentrated using rotary evaporator. The residue is purified by flash column chromatography over silica gel using ethyl acetate and hexane as eluent to yield 33 (1.8 g).

4-Isopropylbenzenesulfonamide 17

To a solution of deuterated 4-isopropylbenzenesulfonyl chloride 33 (1.7 g) in THF is added ammonium hydroxide ($NH_4OH$) and stirred overnight. The mixture is partitioned between water and mixture of ethyl acetate (EtOAc) and ether. The organic phase is separated and washed with brine, dried over $Na_2SO_4$, filtered and concentrated in vacuo. The residue is purified by flash column chromatography over silica gel using mixture of ethyl acetate and hexane as eluent to give the sulfonamide 17 (1.5 g).

The following examples illustrate the preparation of the compounds of formula I and as such are not be considered as limiting the invention set forth in the claims appended hereto.

Preparation of 4-Hydroxyaniline-$d_2$ 3

To 4-aminophenol 2 (1.1 g) is added 1 equivalent of concentrated (conc) HCl and $D_2O$ (1.2 g). The reaction mixture is heated (irradiated) in a microwave at 180° C. for 30 minutes. The reaction mixture is allowed to attain room temperature and quenched cautiously with saturated aqueous solution of NaOH by slow addition. When the mixture is basic, the deuterated hydroxyaniline is extracted with a mixture of methylene chloride, ether and EtOAc. The organic solvent extracts are dried over anhydrous $Na_2SO_4$, filtered and concentrated to give 3 (0.85 g).

Preparation of 4-Hydroxybenzonitrile-$d_2$ 4

To a stirred solution of 3 (5 g) in HCl at 0° C. is added $NaNO_2$ and the mixture stirred for an hour to produce a corresponding diazonium salt in situ. Cuprous cyanide (CuCN, 1.5 equiv) is added to the reaction mixture and stirred for 2 hours at 0° C. and for 3 hours at room temperature. The mixture is diluted with methylene chloride and ether and then filtered through celite. The organic phase is separated and dried over anhydrous $Na_2SO_4$, filtered and concentrated to yield deuterated 4 (4.2 g). Use of KCN instead of CuCN is also used to convert the diazonium salt to the nitrile 4.

Scheme 6

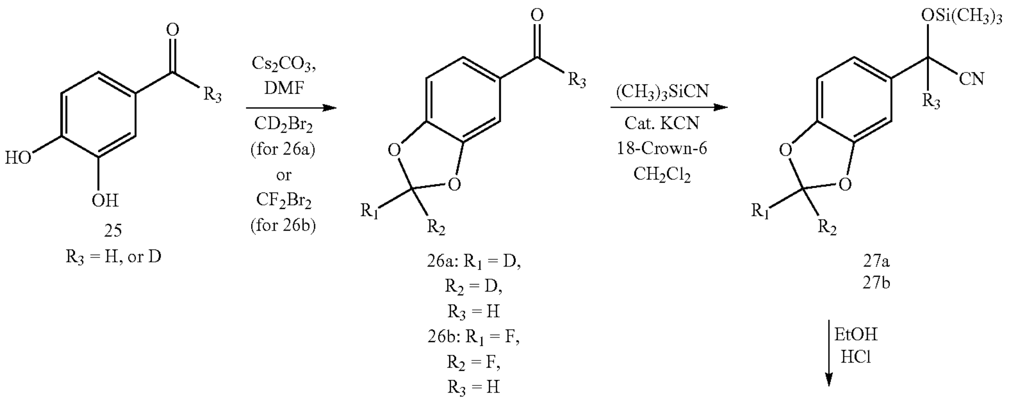

25
$R_3$ = H, or D

26a: $R_1$ = D, $R_2$ = D, $R_3$ = H
26b: $R_1$ = F, $R_2$ = F, $R_3$ = H 27a
27b

-continued

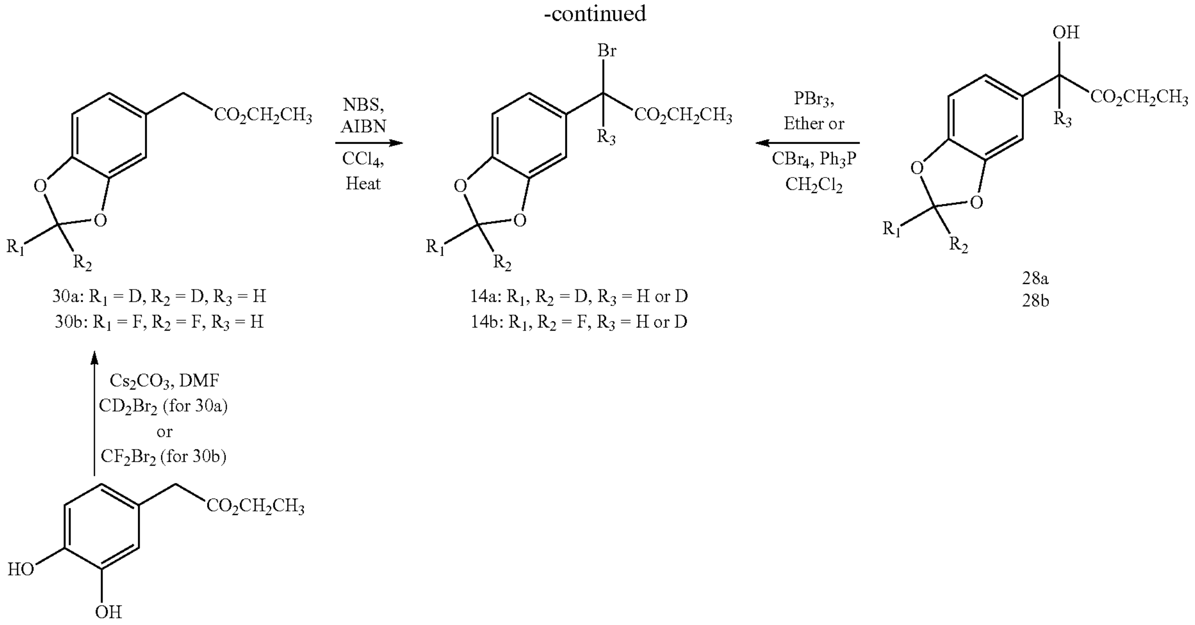

30a: $R_1$ = D, $R_2$ = D, $R_3$ = H
30b: $R_1$ = F, $R_2$ = F, $R_3$ = H

14a: $R_1$, $R_2$ = D, $R_3$ = H or D
14b: $R_1$, $R_2$ = F, $R_3$ = H or D 28a
28b

29

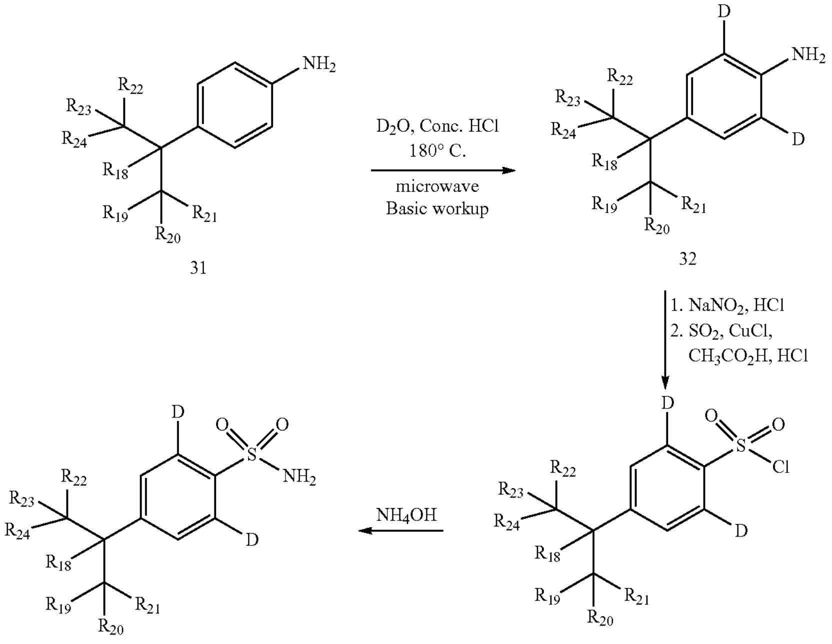

31

32

33
$R_{18}$, $R_{19}$, $R_{20}$, $R_{21}$, $R_{22}$, $R_{23}$, $R_{24}$ = D or H

17
$R_{18}$, $R_{19}$, $R_{20}$, $R_{21}$, $R_{22}$, $R_{23}$, $R_{24}$ = D or H

Preparation of Methyl 4-Hydroxybenzonitrile-$d_2$ 5

Conc. $H_2SO_4$ is added to a stirred solution of 4 (4.2 g) in anhydrous methanol and the reaction mixture refluxed overnight. Methanol is removed in vacuo and the residue dissolved in a mixture of methylene chloride, ether and ethyl acetate. The organic phase is concentrated and the desired ester is purified by flash column chromatography over a short column packed with silica gel and using mixture of EtOAc/Hexane as eluent to yield 5 (3.7 g).

Use of EtOH instead of MeOH provides the ethyl ester 5. Also, the use of HCl instead of $H_2SO_4$ produces the methyl or the ethyl ester when the mixture is refluxed in methanol or ethanol respectively.

Methyl 4-Aminobenzoate-$d_2$ 7

A mixture of 4-aminobenzoate 6 (1.5 g), $D_2O$ and conc. HCl (1 equiv) is heated by irradiating in a microwave at 180° C. for 30 minutes. The reaction mixture is basified by slow addition of aqueous NaOH solution and extracted with a solvent mixture of methylene chloride, EtOAc and ether.

The combined organic extracts are dried over anhydrous $Na_2SO_4$, filtered and concentrated in vacuo to yield 7 (1.1 g).

Methyl 4-Hydroxybenzoate-$d_2$ 8

To a solution of 7 (1.1 g) in hydrochloric acid (HCl) at 0° C. is added $NaNO_2$ (1.2 equiv) and stirred for an hour to afford the corresponding diazonium salt in situ. Cuprous oxide or aqueous KOH is added to the reaction mixture and stirred for 2 hours at 0° C. and then at room temperature for 6 hours. The reaction mixture is acidified by adding dilute HCl and extracted with a mixture of methylene chloride, EtOAc and ether. The combined organic extracts are dried over anhydrous $MgSO_4$, filtered and concentrated in vacuo to give crude 8 which is purified by flash column chromatography over silica gel and using a gradient of EtOAc in hexane as eluent to give pure 8 (0.85 g).

Preparation of N-(4-isopropylbenzenesulfonyl)-α-(4-carboxy-2-n-propyl-phenoxy)-3,4-methylenedioxy-$d_2$-phenylacetamide

Preparation of 3,4-methylene-$d_2$-dioxybenzaldehyde 26a ($R_1$ and $R_2$=D, $R_3$=H)

To a stirring solution of 3,4-dihydroxybenzaldehyde, 25 (1.38 g, 0.01 mole), in DMF in a round bottom flask placed in an ice-bath is added cesium carbonate, $Cs_2CO_3$ (10 g) followed by addition of dibromomethane-$d_2$, $CD_2Br_2$ (4.2 g). The resulting mixture is stirred for overnight at room temperature and then quenched with saturated aqueous solution of ammonium chloride and the mixture stirred for 10 minutes. The organic product is extracted with a mixture of solvents, methylene chloride, ethyl acetate and ether three times. The combined extracts are washed successively with aqueous $NaHCO_3$ solution and brine, and then dried over anhydrous magnesium sulfate, filtered and the filtrate concentrated in vacuo to yield crude 26a-$d_2$. Flash column chromatography over silica gel using a mixture of EtOAc in hexane gives 26a-$d_2$ (1.1 g).

Preparation of 3,4-(difluoromethylenedioxy)benzaldehyde 26b ($R_1$ and $R_2$=F, $R_3$=H)

To a stirring solution of 3,4-dihydroxybenzaldehyde, 25 (1.38 g, 0.01 mole) in DMF at 0° C. is added cesium carbonate, $Cs_2CO_3$ (10 g) followed by addition of dibromomethane-$d_2$, $CF_2Br_2$ (2.5 mL, 0.027 mole). The resulting mixture is stirred overnight at room temperature and then quenched with saturated aqueous solution of ammonium chloride and the mixture stirred for 10 minutes. The organic product is extracted with a mixture of solvents, methylene chloride, ethyl acetate and ether three times. The combined extracts are washed successively with aqueous $NaHCO_3$ solution and brine, and then dried over anhydrous magnesium sulfate, filtered and the filtrate concentrated in vacuo to yield 26b (1.1 g) after flash column chromatography.

Preparation of Trimethylsilyloxy Nitrile 27a-$d_2$

To a stirred solution of 26a (1 g) in methylene chloride is added trimethylsilyl cyanide (TMSCN), (1.2 equiv) a catalytic amount of KCN (5-10%) and 18-crown-6 (5-10%) and the mixture stirred overnight. The reaction mixture is quenched with water, extracted with methylene chloride, ethyl acetate and ether. The organic extracts are washed with brine, dried over anhydrous $MgSO_4$, filtered and the filtrate concentrated in vacuo to produce 1.1 g of 27a after purification by flash column chromatography over silica gel and ethyl acetate/hexane as eluent.

Preparation of Trimethylsilyloxy Nitrile 27b 27b (Scheme 6) is prepared from 26b as described above for the preparation of 27a.

Preparation of α-Hydroxy Ester 28a

Through a stirred solution of 27a (1 g) in anhydrous ethanol (25 mL) is bubbled gaseous HCl for 0.5-1 hour and the reaction mixture stirred for 6-8 hours. The excess of HCl is allowed to evaporate and the solution is concentrated to yield the hydroxyester 27 (1 g).

Preparation of α-Hydroxy Ester 28b 28b (Scheme 6) is prepared from 27b as described above for the preparation of 28a ($d_2$).

Ethyl 3,4-methylenedioxy-$d_2$-phenyl Acetate 14a

A solution of the hydroxyester 28a (0.55 g) is treated with $Ph_3P$ (1.1 equiv) and carbon tetrabromide (1.1 equiv) at 0° C. for 1-2 hours. The reaction mixture is quenched with methanol and the product is purified by flash column chromatography over silica gel and ethyl acetate/hexane to yield corresponding ethyl α-bromoester 14a (0.45 g).

Alternatively, 28a (0.4 g) is converted into 14a (0.3 g) by treating ethereal solution of 28a with phosphorus tribromide $PBr_3$ for 5-6 hours. The reaction mixture is quenched with methanol and the product purified by flash column chromatography. Similarly, 14b is prepared from α-hydroxyester 28b as described above for the preparation of 28a.

Alternatively, 14a is also prepared by α-bromination of the corresponding ethyl phenylacetate 30a with NBS/AIBN in refluxing carbon tetrachloride. The ethyl ester 30a is prepared from ethyl 3,4-dihydroxyphenyl acetate 29 by its treatment with $Cs_2CO_3$ and $CD_2Br_2$ or $CD_2Cl_2$ in DMF.

The α-bromoester 14b is prepared from ethyl 3,4-dihydroxyphenyl acetate 29 as described above for preparation of 14a from 29. Treatment of 29 with $CF_2Br_2$ and $Cs_2CO_3$ in DMF overnight affords 30b after workup of the reaction followed by flash column chromatography. Bromination of 30b with NBS, and catalytic amount of AIBN in refluxing $CCl_4$ gives 14b.

Methyl 4-Allyloxybenzoate 11

To a stirring solution of methyl 4-hydroxybenzoate 9 (15.2 g) is added potassium carbonate (15 g) and acetone (100 mL) followed by slow addition of allyl bromide 10 (15 g) and the resulting reaction mixture refluxed overnight. The volatile solvent and reagents are removed in vacuo and the residue is diluted with a mixture of methylene chloride, ethyl acetate and ether. The organic vacuo and the allylated product is purified by flash column chromatography over silica gel and ethyl acetate/hexane to yield 11 (17 g).

Methyl 4-Allyloxy-$d_5$-benzoate 11-$d_5$

Deuterium containing analog of 11 (where $R_{11}$, $R_{12}$, $R_{13}$, $R_{14}$ and $R_{15}$=D, deuterium) is prepared by alkylation of 9 with deuterated allyl bromide-$d_5$ 10 under reflux conditions using $K_2CO_3$/acetone as described above. A mixture of 4-Hydroxybenzoic acid 9 (2 g), allyl bromide-$d_5$ 10 (1 g) and $K_2CO_3$ (2.25 g) is refluxed overnight in acetone. The reaction work up and the purification and isolation of the product 11-$d_5$ (1.4 g) is carried out as described in the above procedure.

Methyl 3-allyl-4-hydroxybenzoate 12-$d_5$

A solution of methyl 4-allyloxybenzoate-$d_5$-11 (1.3 g) in dichlorobenzene is heated at 185° C. for 20 hours. The resulting mixture is concentrated in vacuo and purified by flash column chromatography over silica gel using a gradient mixture of ethyl acetate in hexane to give 12 (1.04 g).

Methyl 3-allyl-4-hydroxybenzoate 12

Undeuterated 12 is prepared from the corresponding undeuterated 11 via claisen rearrangement as described above for the preparation of 12-$d_5$. Deuterated 12 is also prepared from the appropriate deuterated 11.

Methyl 3-propyl-4-hydroxybenzoate 13-$d_5$

To a solution of methyl 3-allyl-4-hydroxybenzoate-$d_5$ 12 (0.5 g) in methanol is added 10% palladium on carbon (Pd/C) as catalyst for hydrogenation and it is shaken under atmosphere of $H_2$ gas for 6 hours. After completion of the reaction, the mixture is filtered through celite and the filtrate is concentrated in vacuo to give pentadueterated 13 (0.45 g).

Methyl 3-propyl-4-hydroxybenzoate 13-$d_7$

To a solution of deuterated 13 ($d_5$) (0.3 g) in methanol is added a catalytic amount of 10% palladium on carbon and the mixture stirred under an atmosphere of $D_2$ for 12 hours. The mixture is filtered through celite and the filtrate concentrated in vacuo to yield 13 ($d_7$) (0.25 g).

Alternatively, undeuterated (R=H) or partially deuterated (R=H and D) 13 is stirred with with 10% Pd/C (10 weight % of the 13) in deuterated water ($D_2O$) at 160° C. in a sealed tube under $H_2$ atmosphere for 24 hours. After cooling the reaction mixture is diluted with ether and the mixture is filtered using a membrane filter (Millipore LCR 13-LG). The filtered catalyst is washed with ether twice. The combined ethereal layer is washed with water and brine, dried over $Na_2SO_4$ and concentrated in vacuo to give the deuterated product 13 (R=D). to produce deuterated propyl ($d_7$) derivative 13 (R=D). [Ref. Sajiki, H, et al. Efficient C—H/C-D exchange reaction on the alkyl side chain of aromatic compounds using heterogeneous Pd/C in $D_2O$·, Organic Letters (Org. Lett), 2004, 6 (9), 1485-1487).

Ethyl 2-(4-carbomethoxy-2-n-propylphenoxy)-3,4-methylenedioxyphenylacetate 15

A mixture of 13-$d_5$ (0.5 g), α-bromoester 14 (1.1 equiv) and $K_2CO_3$ (2.5 equiv) in acetone is refluxed overnight (approximately 24 hours). The reaction mixture is concentrated in vacuo and diluted with a solvent mixture of methylene chloride, EtOAc, ether and then washed with saturated aqueous solution of NaCl (brine). The organic phase is dried over anhydrous $MgSO_4$, then filtered and the filtrate concentrated in vacuo. The resulting oily residue is purified by flash column chromatography using silica gel and a gradient mixture of EtOAc in hexane as eluent to yield 15 (0.55 g).

2-(4-carbomethoxy-2-n-propylphenoxy)-3,4-methylenedioxyphenylacetic Acid 16

A solution of 15 (0.5 g) in methanol is treated with 4N aqueous NaOH solution and the reaction monitored quickly by TLC for progress and completion of mono-saponification of the ethyl ester. The reaction mixture is treated with 9N HCl after completion of hydrolysis of ethyl ester only. A saturated aqueous solution of $NaHCO_3$ is added to the reaction mixture and methanol is removed in vacuo. The mixture is partitioned between ether and water and the organic phase containing impurities is discarded and the aqueous phase which contains the product is acidified with 9N HCl and the product extracted into EtOAc. The EtOAc solution is dried over anhydrous $MgSO_4$, filtered and the solvent removed in vacuo to give deuterated 16 (0.38 g).

Deuterated N-(4-isopropylbenzenesulfonyl)-α-(4-carbomethoxy-2-n-propylphenoxy)-3,4-methylenedioxyphenylacetamide 18

To a solution of deuterated 16 (0.2 g) in anhydrous THF (3 mL) is added carbonyldiimidazole (CDI) (3 equiv) and the mixture heated at 55° C. for 3 hours. To this reaction mixture is added a mixture of 4-isopropylbenzenesulfonamide 17 (4 equiv) and diazabicycloundecene (DBU) (4 equiv) and the resulting reaction mixture is heated at 55° C. for 3 hours. After completion of the reaction, the contents are concentrated in vacuo and then diluted with 2:1 mixture of ethyl acetate and diethyl ether. The organic phase is washed with 5% citric acid, water and saturated aq NaCl solution, then dried over $MgSO_4$, filtered and concentrated in vacuo. The residue is purified by flash column chromatography over silica gel using a solvent mixture of $CH_2Cl_2$:MeOH: $NH_4OH$ (90:9:1) to yield deuterated 18 (0.195 g).

Preparation of Deuterated α-(4-carboxy-2-n-propylphenoxy)-3,4-methylene($d_2$)dioxyphenylacetic Acid 19

To a solution of 16 (0.5 g) (Scheme 4) in methanol is added 5N NaOH aqueous solution (1 mL) of sodium hydroxide (NaOH/$CH_3OH$) and stirred overnight. Methanol is removed under vacuo and the mixture is then acidified by addition of 6N HCl. The product 19 is crystallized from a mixture of ethyl acetate and hexane to yield the deuterated diacid 19 (0.3 g).

Preparation of α-(4-carbomethoxy-2-n-propylphenoxy)-3,4-methylene-$d_2$-dioxyphenylacetic Acid Potassium 20-$d_2$ A saturated aqueous solution (2 mL) of potassium bicarbonate ($KHCO_3$) is added to a slurry of compound 16 (0.2 g) in a mixture of 1:1 ethyl acetate and ether and stirred overnight. The product is filtered and washed successively with water followed by diethyl ether (ether) to yield the potassium salt of the monoester mono-acid, 20-$d_2$ (0.15 g).

Preparation of α-(4-carboxy-2-n-propylphenoxy)-3,4-methylene-$d_2$-dioxyphenylacetic Acid Dipotassium 21-$d_2$ A solution of potassium hydroxide (KOH) in water (3 mL) and methanol (2 mL) is a added to the diacid 19-$d_2$ (0.2 g) and stirred for an hour followed by heating at 50° C. for 2 hours to ensure complete formation of potassium salt (Scheme 4). The mixture is cooled to room temperature and then methanol ($CH_3OH$) removed in vacuo to give dipotassium salt 21 which is recrystallized from absolute ethanol ($CH_3CH_2OH$) and water to yield 21-$d_2$ (0.12 g).

N-(4-isopropylbenzenesulfonyl)-α-(4-carbomethoxy-2-n-propylphenoxy)-3,4-methylene-$d_2$-dioxyphenylacetamide Potassium 22

A saturated aqueous solution (2 mL) of potassium bicarbonate ($KHCO_3$) is added to a slurry of 18($d_2$) (0.15 g) in a mixture of 1:1 ethyl acetate and ether and stirred overnight. The product is filtered and washed with water followed by ether to yield the potassium salt of the monoester sulfonamide, 22-$d_2$ (0.1 g).

N-(4-isopropylbenzenesulfonyl)-α-(4-carboxy-2-n-propylphenoxy)-3,4-methylene-$d_2$-dioxyphenylacetamide 23

To a solution of 18 (0.23 g) (Scheme 5) in methanol is added 5N aqueous solution of sodium hydroxide (NaOH) (1 mL) and the resulting solution stirred overnight. Methanol is removed under vacuo and the mixture is then acidified with the addition of 6N hydrochloric acid (HCl). The product 23 is recrystallized from ethyl acetate and hexane mixture to yield the 23-$d_2$ (0.15 g).

N-(4-isopropylbenzenesulfonyl)-α-(4-carboxy-2-n-propylphenoxy)-3,4-methylene-$d_2$-dioxyphenylacetamide Dipotassium 24

A solution of 1N KOH in methanol (2 mL) and water (3 mL) is a added to 23-$d_2$ (0.15 g) and stirred for an hour followed by heating at 50° C. for 2 hours to ensure complete formation of potassium salt (Scheme 5). The mixture is cooled to room temperature and methanol removed in vacuo to give dipotassium salt 24 which is recrystallized from absolute ethanol and water to yield 24-$d_2$ (0.1 g).

Alternatively, 24 ($d_2$) is prepared from the corresponding methyl ester by saponification with aqueous solution of potassium hydroxide (KOH). A mixture of ester 22 (0.22 g) and 1N solution of potassium hydroxide (KOH) (2 mL) in methyl alcohol (methanol, $CH_3OH$ or MeOH) is heated at 50° C. for 2 hours. The reaction contents are allowed to attain room temperature and the solvent removed in vacuo. The dipotassium obtained as such is recrystallized from absolute ethanol and water to give 24-$d_2$ (0.13 g).

Treatment of the methylesters 18, with sodium triacetoxy-borohydride-$d_1$ [$NaBD(OAc)_3$] in deuterated or non-deuterated methanol produces the corresponding alcohol derivatives 34 in good to excellent yield, after purification as shown in Scheme 7 below. Alternatively, the alcohol compounds represented by 34 are also prepared by the treatment (reduction) of the methylesters represented by 18 with lithium aluminum deuteride ($LiAlD_4$) in diethyl ether (aka ethyl ether or $Et_2O$) in good to excellent yields. Similarly methylesters represented by compounds 18 in Scheme 7 are also reduced to their corresponding alcohol derivatives shown by compound structures 35 by treating 18 with triacetoxy sodium borohydride [$NaBH(OAc)_3$ in dichloroethane (DCE) or alternatively treatment with lithium aluminum hydride (LiAlH4) in diethyl ether (Ether) or tetrahydrofuran (THF). These alcohol compounds (34 and 35) are converted into their corresponding bromides by their treatment with triphenyl phosphine ($Ph_3P$) and carbon tetrabromide ($CBr_4$) in dichloromethane ($CH_2Cl_2$) as solvent at 0° C. for a few hours, as shown in Scheme 7.

Scheme 7

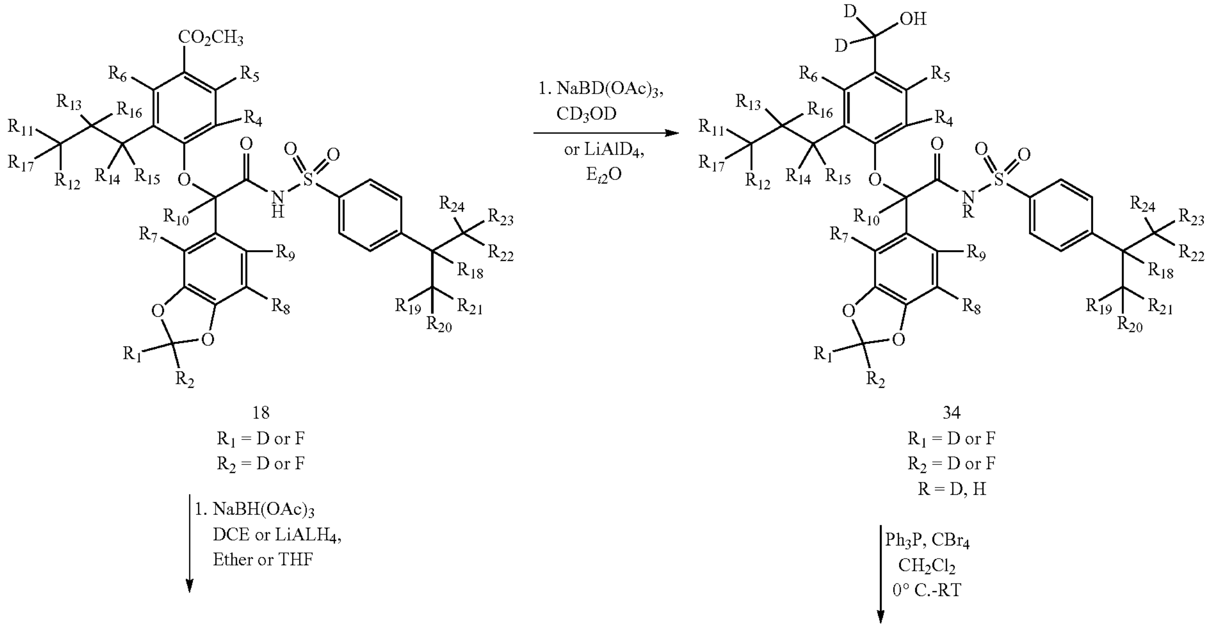

18
$R_1$ = D or F
$R_2$ = D or F

34
$R_1$ = D or F
$R_2$ = D or F
R = D, H

-continued

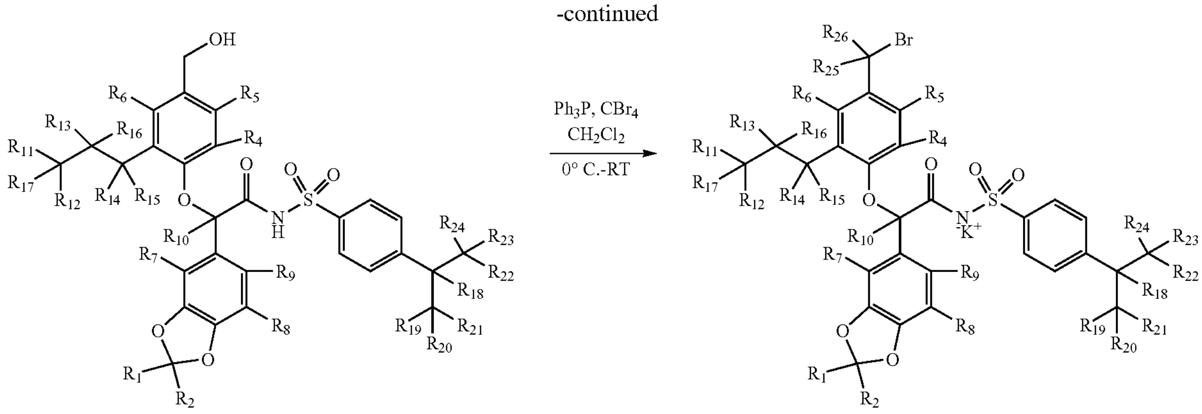

35
$R_1$ = D or F
$R_2$ = D or F

36
$R_1$ = D or F;
$R_2$ = D or F
$R_{25}$ and $R_{26}$ = D, H

Preparation of α-Bromo-phenylacetates 40

Appropriate aldehyde 37 is treated with trimethylsilyl cyanide [$(CH_3)_3SiCN$] in the presence of catalytic amount of potassium cyanide (KCN) and 18-crown-6 in methylene chloride ($CH_2Cl_2$) for overnight. Water is added cautiously and slowly to the reaction mixture and stirred. The reaction contents are diluted with a solvent mixture of methylene chloride, ethyl acetate and diethyl ether (1:1:1) and stirred. The organic phase is separated from aqueous phase (water layer). Aqueous layer is further extracted twice with the same solvent mixture and the combined extracts are washed successively with saturated aqueous solutions of sodium bicarbonate and sodium chloride. The resulting organic phase is dried over anhydrous sodium sulfate, filtered and then concentrated in vacuo using rotatory evaporator to yield the corresponding trimethylsilyl cyanohydrin 38 which is used in the next step without any further purification. Hydrolysis of 38 by treatment with hydrochloric gas (HCl) in ethanol ($CH_3CH_2OH$ or EtOH) at 0° C. for one hour and then the reaction mixture allowed to stir over night and then concentrated before using in the next step. Hydroxy ester 39 is converted to the corresponding bromide 40 either by its treatment with Phosphorus tribromide ($PBr_3$) in diethyl ether at 0° C. or alternatively using carbon tetrabromide and triphenyl phosphine ($CBr_4$, $Ph_3P$) in methylene chloride at 0° C. After complete conversion of the hydroxyl ester to the corresponding bromoester (monitored by TLC), the reaction mixture is concentrated in vacuo to yield crude bromoester 40, which is then purified by flash column chromatography over silica gel column using a mixture ethyl acetate in hexane as eluent to obtain the desired purified bromoester compound 40 in excellent yield.

The α-bromophenyl acetate 40 is also prepared by an alternative shorter synthetic route by starting with ethyl 3,4-methylenedioxyphenylacetate 41 that is readily available by refluxing 3,4-methylenedioxyphenylacetic acid in ethyl alcohol (or methyl alcohol as desired) in the presence of a catalytic amount of concentrated sulfuric acid (Conc. $H_2SO_4$). Ester 41 is refluxed with N-Bromosuccinimide (NBS, 1.075 equivalent) and Azobisisobutyronitrile (AIBN, 1.08 equivalent) in carbon tetrachloride ($CCl_4$). Upon completion of the reaction, the crude product is purified by flash column chromatography using silica gel and ethyl acetate in hexane as eluent to obtain the desired deuterated or protio-ethyl α-bromo-3,4-methylenedioxyphenylacetate 40 (α-bromo ester building block) 40, as illustrated in Scheme 8 given below.

Scheme 8

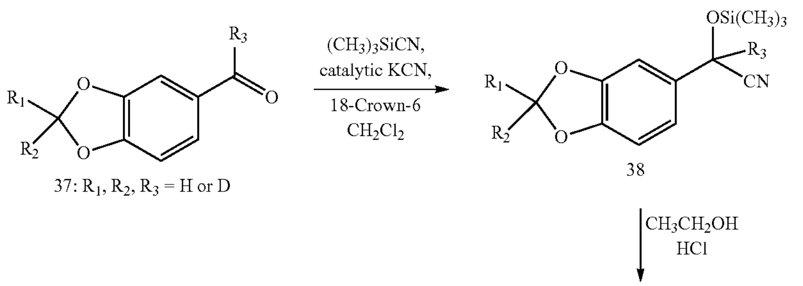

37: $R_1$, $R_2$, $R_3$ = H or D

38

-continued

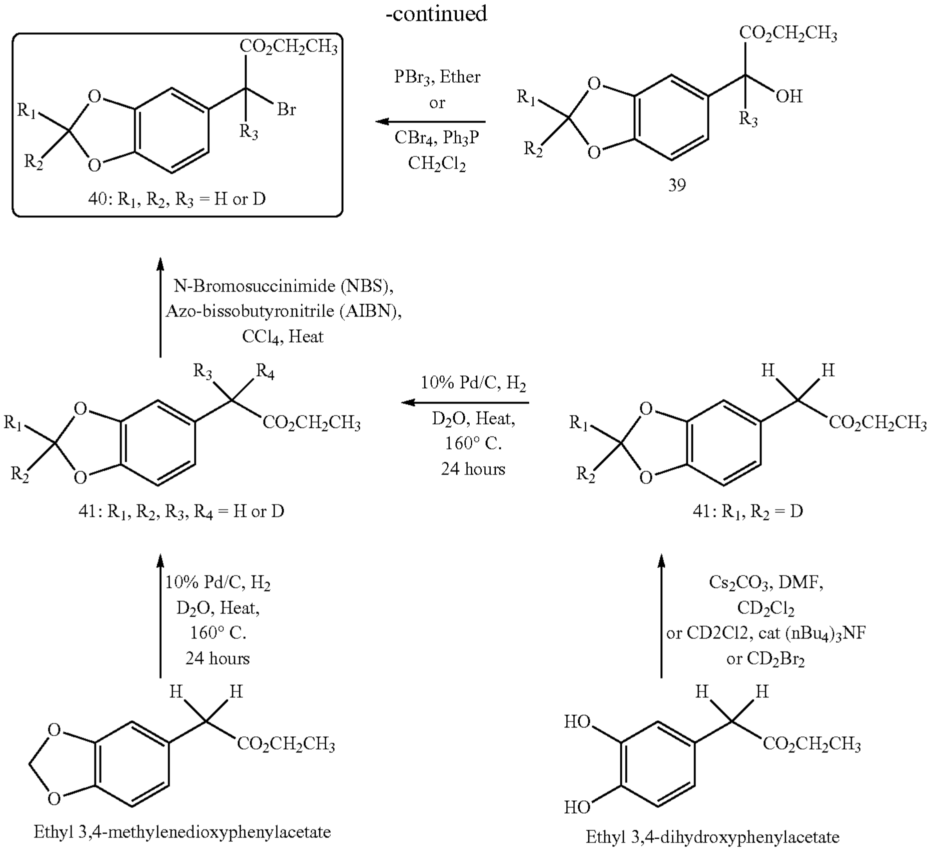

40: $R_1$, $R_2$, $R_3$ = H or D

39

41: $R_1$, $R_2$, $R_3$, $R_4$ = H or D

41: $R_1$, $R_2$ = D

Ethyl 3,4-methylenedioxyphenylacetate

Ethyl 3,4-dihydroxyphenylacetate

Preparation of Deuterated 4-Isopropylbenzenesulfonamide 56

Commercially available deuterated ($d_6$) acetone 42 is converted to deuterated isopropyl alcohols 43 and 44 by reduction of the acetone 42 by treatment with sodium borodeuteride ($NaBD_4$) in methanol or methanol (MeOH) and tetrahydrofuran (MeOH/THF) and sodium borohydride ($NaBH_4$) in methanol or methanol (MeOH) and tetrahydrofuran (MeOH/THF) respectively in excellent yield. Alternatively, treatment of ketone 42 with lithium aluminum deuteride ($LiAlD_4$) in diethyl ether (or ether or $Et_2O$) or THF yields 43 after reaction work-up and purification. Similarly, reduction of deuterated acetone 42 with lithium aluminum hydride ($LiAlH_4$) in ether or THF produces the corresponding alcohol 44. Deuterated alcohols 43 and 44 are converted to the corresponding halides (chloride and bromides) 45 (R=D, X=Cl, Br) and 46 (R=H, X=Cl, Br) by treatment of alcohols with phosphorus chloride (for conversion to the corresponding chloride) and phosphorus tribromide (for conversion of alcohol to the corresponding bromide) in diethyl ether (ether, $Et_2O$) in high yield as shown in scheme 9.

Aniline 47 is converted to N-Boc protected aniline 48 by treatment of the aminobenzene (aniline) 47 with tertiary butyloxycarbonyl anhydride in dioxane (or $THF/CH_2Cl_2$) in the presence of catalytic amount of N,N-dimethylaminopyridine (DMAP) to yield the N-Boc-protected aniline 48. Alternatively, 47 is converted to carboxybenzyloxy protected aniline derivative (CBz-aniline, 49) by treatment of 47 with benzyloxycarbonyl chloride in dioxane or THF/ $CH_2Cl_2$ in the presence of catalytic amount of DMAP in excellent yield.

N-Boc and N-Cbz protected aniline 48 and 49 are transformed to the deuterated ($d_7$) or ($d_6$) 4-isopropylaminobenzene 50 and 51 respectively using Friedel-Crafts alkylation reaction as shown in scheme 9. Treatment of anilines 48 or 49 with deuterated isopropyl chloride, 45 (or deuterated isopropyl bromide 46) in the presence of anhydrous aluminum chloride ($AlCl_3$) or stannic chloride ($SnCl_4$) in dichloromethane at 0° C. produces the corresponding alkylated compounds 50 and 51 in high yields. The N-Boc-4-isopropylaniline derivatives 50 is deprotected by its treatment with trifluoroacetic acid (TFA) or HCl in methylene chloride to produce the desired product, deuterated 4-isopropylaminobenzene 52 in over 95% yield. The Cbz-aniline compound 51 is converted to the desired deprotected 4-isopropylaniline 52 by hydrogenation of 51 over 10% palladium catalyst in ethyl alcohol (ethanol or EtOH) as shown in scheme 9.

Diazotization of deuterated 4-isopropylaminobenzene 52 by its treatment with sodium nitrite in hydrochloric acid ($NaNO_2$/aq. HCl) at 0° C. yield diazonium salt which without its isolation is further treated with cuprous sulfite ($Cu_2SO_3$) or sodium sulfite ($Na_2SO_3$) to produce deuterated 4-isopropylbenzenesulfonic acids 53 in very good yield. Treatment of 53 with thionyl chloride ($SOCl_2$) in toluene yielded the corresponding deuterated 4-isopropylbenzensulfonyl chlorides 55 in excellent yield. In an alternative synthetic route, deuterated 4-isopropylaminobenzenes 52 is converted to the corresponding deuterated 4-isopropyl-benzenethiols 54 via the corresponding diazonium salt in situ prepared by treatment of 54 with sodium nitrite in aqueous HCl ($NaNO_2$/HCl) at 0° C. followed by addition of cuprous sulfide to the diazonium salt to afford 54. Treatment of solution of 54 in acetic acid with chlorine gas produces deuterated 4-isopropylbenzenesulfonyl chloride compounds 55.

The deuterated 4-isopropylbenzenesulfonyl chlorides prepared as described above are treated with an aqueous solution of ammonium hydroxide ($NH_4OH$) to produce the desired key intermediate, deuterated 4-isopropylbenzenesulfonamides 56 as shown in scheme 9.

Methyl 4-hydroxybenzoate 57 (or deuterated alkyl 4-hydroxybenzoate, which is prepared as illustrated for the preparation of 5 and 8 in scheme 1 and 2) is alkylated with partial or fully deuterated or undeuterated allyl bromide 58 (or allyl bromide, allyl chloride, or allyl iodide, or allyl tosylate or allyl mesylate) by refluxing the reaction mixture with potassium carbonate ($K_2CO_3$) in acetone for 6 to 18 h as shown in scheme 10 (also see Dhanoa, D. S. et al., *J. Med. Chem.* 1993, 36, 3788-3742). After completion of the reaction, it is quenched with cold water and then diluted with methylene chloride (or dichloromethane, $CH_2Cl_2$) and washed with brine (saturated aqueous solution of sodium chloride, $NaCl/H_2O$). The organic liquid phase is dried over anhydrous magnesium sulfate, filtered and concentrated under vacuum. The residue obtained as such is purified by flash chromatography (silica gel, ethyl acetate hexanes) to isolate purified alkylated phenoxy methyl ester 59 as illustrated in scheme 10.

Heating a solution mixture of 59 in dichlorobenzene at 185° C. for 8 hours produces the rearranged deuterated (D-derivative), partially deuterated (D-derivative) or undeuterated (H-derivative) methyl 4-hydroxy-3-allylbenzoate 60 via the claisen rearrangement (see Dhanoa, D. S. et al., *J. Med. Chem.* 1993, 36, 3788-3742). Deuterated Methyl 4-hydroxy-3-n-allylbenzoate 60 is purified by flash column chromatography over silica gel using gradient mixture of ethyl acetate and hexanes as the eluent. Catalytic hydrogenation of 60 using 10% palladium on carbon (Pd/C) in methanol produces the corresponding deuterated or undeuterated methyl 4-hydroxy-3-n-propylbenzoate 61 in excellent yield. The catalyst is removed by filtering the diluted reaction mixture through celite plug.

Alkylation of 61 with ethyl α-bromo-3,4-methylenedioxyphenylacetate ester 62 (and/or deuterated derivative 62) by treatment of 61 with cesium carbonate ($Cs_2CO_3$) and 62 in anhydrous N,N-Dimethylformamide (DMF) for 4 hours at room temperature produces the desired alkylated disaster 63, which is purified by flash column chromatography.

Scheme 9

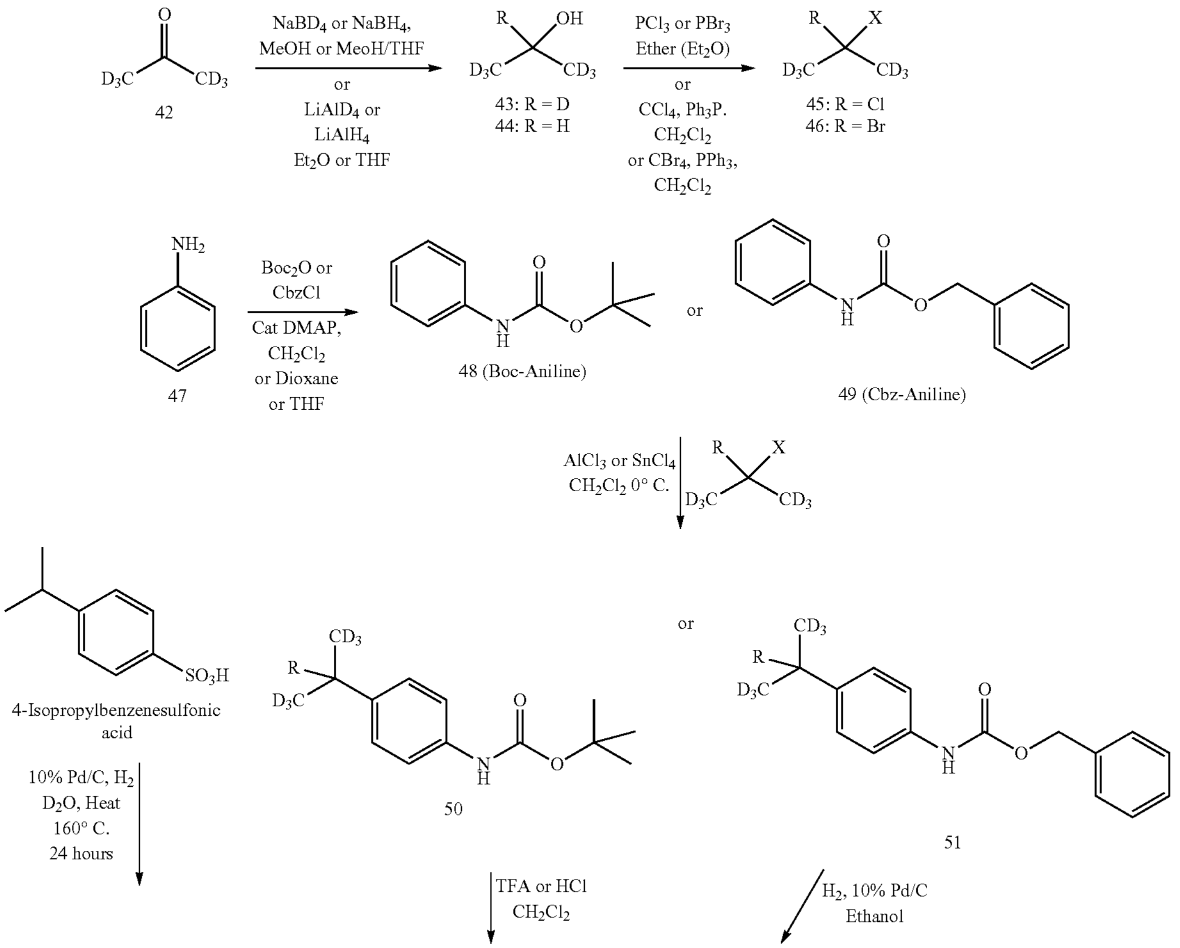

-continued

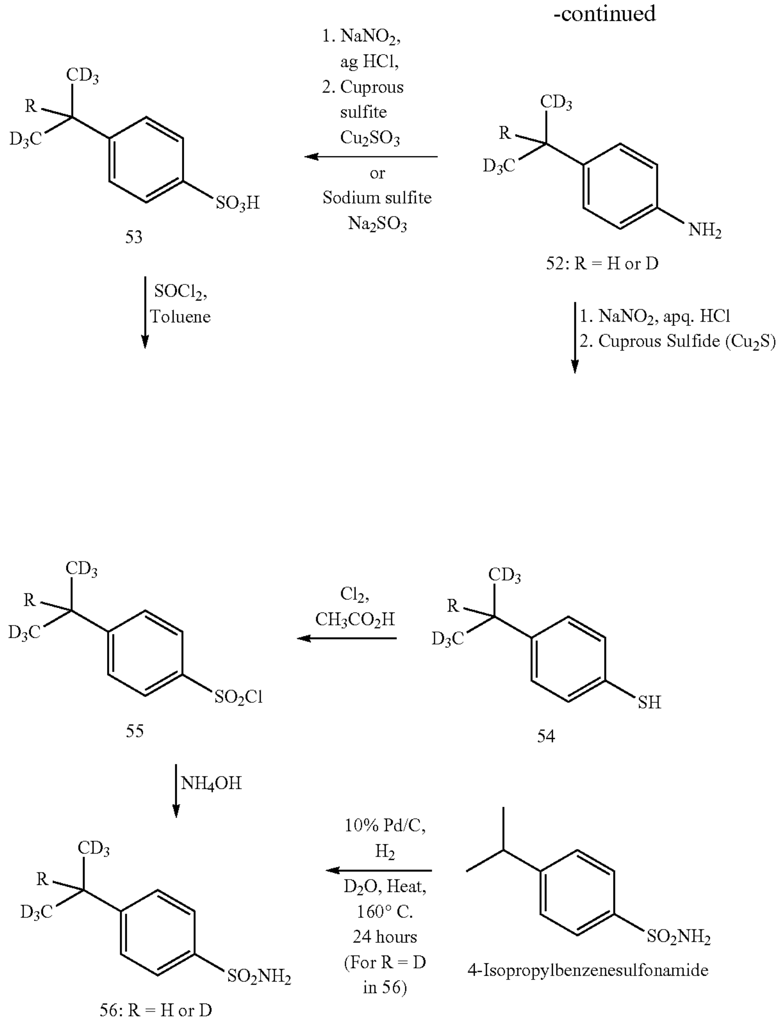

53

52: R = H or D

55

54

56: R = H or D

4-Isopropylbenzenesulfonamide

In an alternative synthetic method, treatment of deuterated methyl 4-hydroxy-3-n-propylbenzoate 61 with ethyl α-bromo-3,4-methylenedioxyphenylacetate ester 62 in the presence of potassium carbonate in acetone under reflux conditions for overnight produces the alkylated diester product 63, which after its purification by flash column chromatography using silica gel and mixture of solvents, ethyl acetate and hexanes affords the pure compound 63. The diester 63 is converted to the corresponding mono ester carboxylic acid by its saponification (hydrolysis of ethyl ester) using 5 N aqueous solution of sodium hydroxide in methanol ($NaOH/CH_3OH$) for a short period of time, 0.5 h-1 hour, to produce the methyl carboxylic acid ester 64. Phenoxyphenylacetic acid 64 is converted into its corresponding acylsulfonamide 65 by refluxing (or heating at 50-55° C.) of compound 64 (1 equivalent) with carbonyldiimidazole (CDI, 1.5 equivalent) in tetrahydrofuran (THF) for 4 hours. At room temperature, a mixture of 1.5 equivalent of appropriately deuterated 4-isopropylbenzenesulfonamide 56 and 1.5 equivalent of the base diazabicycloundecene (DBU) in THF is added to the reaction mixture and then stirred for overnight. The resulting reaction mixture is then diluted with ethyl acetate and washed with 5% aqueous solution of citric acid. The solvent is removed and the resulting crude product is purified by flash column chromatography to give the desired acylsulfonamide 65 as shown in scheme 10. Various deuterated compounds, Isopropylbenzenesulfonamides 17 and 56, are prepared from 4-isopropylbenzenesulfonyl chloride by treating with ammonium hydroxide ($NH_4OH$) as illustrated in scheme 6 and scheme 9.

Treatment of the mono methyl ester acid 64 with 5N aqueous solution of sodium hydroxide in methanol (aq $NaOH/CH_3OH$) for a longer period of time yields the corresponding dicarboxylic acids such as 19 as shown in scheme 4. The reaction is followed by thin layer chromatography (TLC) to ensure complete conversion of monoesters to the corresponding dicarboxylic acids.

The acylsulfonamide 65 is treated with potassium hydroxide in methanol ($KOH/CH_3OH$) to prepare its potassium salt 66 as shown in scheme 10. Treatment of 65 with aqueous solution of sodium hydroxide in methanol (aq. $NaOH/CH_3OH$) produces the corresponding sulfonamide carboxylic acid. Treatment of 66 with solution of potassium hydroxide in methanol ($KOH/CH_3OH$) yields the dipotassium salt 67. The dipotassium salt product compound 67 is also prepared directly from the compound 65 by its saponification with aqueous solution of Scheme 10
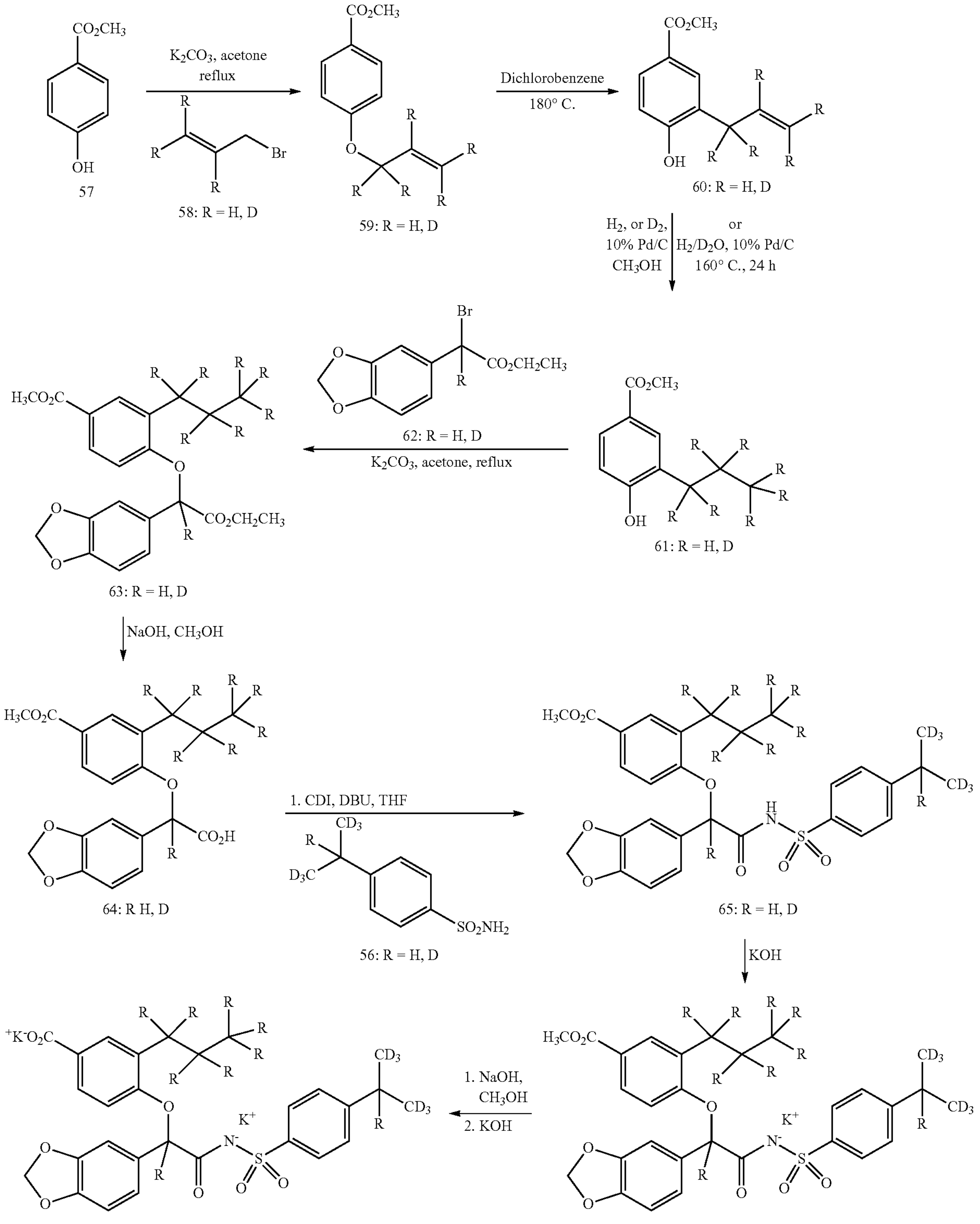
57
58: R = H, D
59: R = H, D
60: R = H, D
61: R = H, D
62: R = H, D
63: R = H, D
64: R H, D
56: R = H, D
65: R = H, D
66: R = H, D
67: R = H, D sodium hydroxide (NaOH) in methanol ($CH_3OH$) followed by a treatment of the isolated acid with potassium hydroxide (KOH) in methanol ($CH_3OH$) as shown in Scheme 10.

EXAMPLES

Methyl 3-Allyl-4-hydroxybenzoate

Step A: Preparation methyl 4-allyloxybenzoate

To a nitrogen flushed 5 L three neck round bottom flask fitted with a condenser, mechanical stirrer, and a nitrogen ($N_2$) gas inlet is added 600 g of methyl 4-hydroxybenzoate, 500 ml of deuterated ($d_5$, $d_3$) allyl bromide, 660 g of anhydrous potassium carbonate ($K_2CO_3$), and 2.25 L of acetone. The equipped reaction flask with contents is heated at reflux with efficient mechanical stirring for 2 hours. An additional batch of 50 g of potassium carbonate is added cautiously to the reaction flask and stirred further for one hour. Furthermore, another batch of 20 g of potassium carbonate is added to the reaction flask cautiously and the contents of the reaction flask are stirred for additional 30 minutes at reflux. The contents of the reaction flask are then allowed to attain room temperature with continuous stirring and further stirred overnight. The reaction mixture is filtered and the solid is washed with acetone (3.5 L). The filtered solution is concentrated to produce 775 g of nearly colorless oil. The product obtained as such is characterized by nuclear magnetic resonance (NMR) spectrum analysis and thin layer chromatography (TLC) using silica gel plates and 1:1 ethyl acetate:hexane at solvent. The product obtained is the expected compound methyl 4-allyloxybenzoate.

Step B: Preparation of methyl 3-allyl-$d_5$-4-hydroxybenzoate

A three neck three 3 L round bottom flask is fitted with a mechanical stirrer, water condenser and a nitrogen ($N_2$) gas inlet. The flask was flushed with $N_2$. Methyl 4-allyloxy($d_5$) benzoate (770 g) is added to the reaction flask followed by addition of 425 mL of 1,2-dichlorobenzene and 12 g of BHT. The resulting mixture solution is heated and distillate collected until the head temperature reaches 180° C. The contents of the reaction flask are heated at reflux temperature for 7 hours and then cooled to 140° C. and allowed to stirred overnight. The hot solution is then poured into 2.5 L of hexanes. The resulting material is filtered, and the solid washed with n-hexanes. The solid white material is allowed to stand to air dry to give the product, 3-allyl-4-hydroxybenzoate in high yield (97%). Expected $^1H$ NMR (300 MHz, $CDCl_3$, ppm): δ 3.42 (dt, J=6.4, 1.4 Hz, 2H), 3.87 (s, 3H), 5.11-5.87 (bs, 1H), 5.93-6.06 (m, 1H), 6.83 (d, J=7.9 Hz, 1H), 7.79-7.85 (m, 2H).

Methyl 4-hydroxy-3-n-propylbenzoate

A solution of methyl 3-allyl 4-hydroxybenzoate (360 g) in methanol (1500 mL) is hydrogenated in a Parr type shaker at 40 psi and room temperature (ambient temperature) using 1.5 g of 10% palladium on carbon (Pd/C) as the catalyst. The reaction mixture is filtered and cake washed with methanol (1000 mL). The combined filtrate is concentrated and the resulting oil material as reduced product flushed with diethyl ether. Hexanes (1500 mL) is added and the resulting suspension is cooled to 0° C. The reduced product is obtained by filtration, washed with hexanes and then dried to give methyl 4-hydroxy-3-n-propylbenzoate (175 g). The remaining filtrate is concentrated and diluted with hexanes and then filtered to obtain the second crop of the hydrogenated product (165 g) yielding the product (340 g) in high yield. Expected $^1H$ NMR (300 MHz, $CDCl_3$, ppm): δ 0.94 (t, J=7.4 Hz, 3H), 1.63 (m, 2H), 2.59 (t, J=7.7 Hz, 2H), 3.86 (s, 3H), 5.87 (s, 1H), 6.84 (d, J=8.4 Hz, 1H), 7.76 (dd, J=8.4, 2.2 Hz, 1H), 7.81 (d, J=2.2 Hz, 1H).

Preparation of Ethyl α-hydroxy-3,4-methylenedioxyphenylacetate

Step A: α-Trimethylsilyloxy-3,4-methylenedioxyphenylacetonitrile

A single neck 3 L round bottom flask fitted with a nitrogen gas inlet and a mechanical stirrer is flushed with nitrogen. Piperonal (3,4-methylenedioxybenzaldehyde) (250 g) is added to the flask followed by addition of 180 g of trimethylsilylcyanide ($Me_3SiCN$), 0.2 g of potassium cyanide, 0.2 g of 18-crown-6 and 500 mL of methylene chloride. The mixture is stirred for 3 hours at room temperature. The reaction mixture is diluted with diethyl ether. Saturated aqueous solution of sodium bicarbonate (275 mL) is added to the ethereal solution and stirred for a half hour. The organic layer is separated using a separatory funnel. The organic layer is washed with another 250 ml of saturated aqueous sodium bicarbonate solution, twice with 300 ml of brine. The organic phase is dried over anhydrous magnesium sulfate, filtered and concentrated to give the product in excellent yield (420 g) as a pale yellow oil and it was used in the next step without any further purification.

Step B: Ethyl α-hydroxy-3,4-methylenedioxyphenylacetate

To a nitrogen flushed magnetically stirred 3 L single neck round bottom flask fitted with a gas inlet is added the trimethylsilyl cyanohydrin obtained as product from the above reaction step and 1 Liter (1 L) of absolute ethanol. The solution is cooled to 0° C., and HCL gas gently bubbled through the solution for 1 hour. After a few minutes the reaction solidifies to a white mass which is allowed to stand at room temperature overnight. Methylene chloride (1 L) and water (1 L) are added. The mixture is shaken for 5 minutes dissolving part of the white solid material. The mixture is decanted and the procedure repeated several more times until all of the solid is dissolved. The layers are separated and the aqueous layer is back extracted with methylene chloride. The combined organic layer is washed with brine, dried over magnesium sulfate and filtered through a pad of silica gel. The solution is concentrated, flushed with ether and diluted with hexanes. The white slurry is cooled to 0° C. the filtered. The cake is washed with 1:2 ether/hexanes followed by hexanes. The product is dried affording 298 g of the product, Ethyl α-hydroxy-3,4-methylenedioxyphenylacetate, as a white solid. A second crop of 20 g is obtained by concentrating the mother liquor giving the title compound in 85% yield. Expected $^1H$ NMR (300 MHz, $CDCl_3$, ppm): δ 1.22 (t, J=7.2 Hz, 3H), 3.41 (d, J=5.6 Hz, 1H), 4.10-4.31 (m, 2H), 5.03 (d, J=5.6 Hz, 1H), 5.94 (s, 2H), 6.77 (d, J=8.5 Hz, 1H), 6.85-6.90 (m, 2H).

Preparation of Ethyl α-bromo-3,4-methylenedioxyphenylacetate

To a nitrogen flushed 5 L three neck round bottom flask fitted with a mechanical stirrer, ad dropping funnel and a nitrogen inlet is added 318 g of ethyl α-hydroxy 3,4-methylenedioxyphenylacetate and 2.6 L of diethyl ether (ether, $Et_2O$). The suspension is cooled to 0-5° C. and a solution of 132 g of phosphoryl tribromide ($PBr_3$) in 370 mL ether is added over a period of a half hour. The reaction is allowed to stand for 2.5 hour at 0-5° C. during which time, an additional 18 g of $PBr_3$ is added. The solid initially present slowly dissolved leaving a clear yellow solution. The reaction is quenched by careful addition of 600 mL of saturated sodium bicarbonate ($NaHCO_3$) aqueous solution and 150 mL of water. The layers are separated and the aqueous layer extracted once with ether. The combined organic phase is washed once with saturated sodium bicarbonate aqueous solution, 10% sodium bisulfite (10% aq, $Na_2SO_3$) solution, brine (aq NaCl), dried over anhydrous magnesium sulfate ($MgSO_4$), and filtered through a pad of silica. The solution is concentrated to 372 g of a pale yellow oil in 91% yield. TLC analysis showed the product as a single spot (silica-1:1 $Et_2O$/Hexanes), and $^1H$ NMR spectrum of the product is in accord with the structure of the title compound and this was used as is in the next step without any further purification. Expected $^1H$ NMR (300 MHz, $CDCl_3$, ppm): δ 1.27 (t, J=7.2 Hz, 3H), 4.10-4.35 (m, 2H), 5.26 (s, 1H), 5.96 (s, 2H), 6.72 (d, J=8 Hz, 1H), 6.94 (dd, J=8 Hz, 1.8 Hz, 1H), 7.11 (d, J=1.8 Hz, 1H).

Preparation of α-(4-Carbomethoxy-2-n-propylphenoxy)-3,4-methylenedioxyphenyl)acetic Acid Sodium Salt

Step A: Ethyl α-(4-carbomethoxy-2-n-propylphenoxy)-3,4-methylenedioxyphenylacetate To a 2 L three necked 24/40 round bottom flask equipped with a mechanical stirrer, a nitrogen inlet and a dropping is first added a solution of 36 g of methyl 4-hydroxy-3-n-propylbenzoate dissolved in 700 mL of anhydrous DMF followed by 67 g of cesium carbonate. The flask is purged with nitrogen gas and the reaction mixture is stirred at room temperature for 2.5 hours. A solution 59 g of ethyl α-bromo-3,4-methylenedioxyphenylacetate dissolved in 100 mL of DMF is then added via an addition funnel over a period of 20 minutes. The reaction mixture is stirred for an additional 1 hour at room temperature and then quenched by addition of 5 L of a 5% aqueous citric acid solution. The organic product is extracted with into diethyl ether (2×4 L), the organic layers are separated, washed with saturated aqueous solution of sodium chloride (NaCl), dried over anhydrous magnesium sulfate ($MgSO_4$), filtered and evaporated. The residue is applied to a silica gel (2 kilogram; 70-230 mesh) column equilibrated in 10% $CH_2Cl_2$-hexane solvent mixture. The column is then eluted successively with 12 L of 10% $CH_2Cl_2$-hexane, 12 L of 5% ethyl acetate-hexane, 4 L of 7.5% ethyl acetate-hexane, 12 L of 10% ethyl acetate-hexane, and finally 8 L of 20% ethyl acetate-hexane. Combination of the purified fractions and evaporation in vacuo gives 76 g of the title compound as a pale yellow oil which is used without further purification in the next step.

Step B: Preparation of α-(4-carbomethoxy-2-n-propylphenoxy)-3,4-methylenedioxyphenylacetate Acid A 1 L-3 necked 24/40 round bottom flask equipped with a mechanical stirrer, a dropping funnel, and a nitrogen inlet is charged with a solution of 76 g of the product of step A dissolved in 500 mL of methanol. The flask is purged with nitrogen, the stirrer is started, and 40 mL of a 5 N aqueous solution of sodium hydroxide (NaOH) is added over a room temperature for an additional 30 minutes at which point TLC analysis ($CH_2Cl_2$:$CH_3OH$:$NH_4OH$=0:10:1) indicates that the starting material is consumed. The reaction mixture is adjusted to pH=4 with 6N HCl, and the bulk of the organic solvent is removed in vacuo. The precipitated organic product and the aqueous layer is next partitioned between 1 L of $CH_2Cl_2$ and 1 L of water. The reaction mixture is then allowed to stand overnight in a refrigerator, which resulted in crystallization of the organic product. The crystalline solid is separated from the two phase mixture by filtration and washed with methylene chloride (dichloromethane, $CH_2Cl_2$). The solid is slurried again in diethyl ether, filtered, washed with hexane, and then dried in a vacuum to give 65 g of the title compound as a white crystalline solid. Expected $^1H$ NMR (400 MHz, $CD_3OD$, ppm): 60.93 (t, J=7.2 Hz, 3H), 1.62-1.75 (m, 2H), 2.63-2.70 (m, 1H), 2.77-2.81 (m, 1H), 3.84 (s, 3H), 5.54 (s, 1H), 5.94 (s, 2H), 6.81 (d, J=7.6 Hz, 1H), 6.89 (d, J=9.2 Hz, 1H), 7.08 (d, J=1.6 Hz, 1H), 7.11 (br s, 1H), 7.78-7.81 (m, 2H).

Preparation of N-(4-iso-propyl($d_7$)benzenesulfonyl)-α-(4-carbomethoxy-2-n-propylphenoxy)-3,4-methylenedioxyphenylacetamide An oven dried three-necked 24/40 1 L round-bottom flask is equipped with a mechanical stirrer, a nitrogen inlet, and a septum. The flask is flushed with nitrogen, then charged with 20 g of the product, α-(4-carbomethoxy-2-n-propylphenoxy)-3,4-methylenedioxyphenylacetate acid, 400 mL of anhydrous tetrahydrofuran (THF), and 10 mL of triethylamine. The reaction flask and its contents are cooled to −78° C. by placing the flask in external dry ice-acetone mixture bath and then 7.3 mL of trimethylacetyl chloride is added slowly via a syringe. After the addition is complete, the dry ice-acetone bath is replaced with an ice-water bath and the reaction is stirred at 0° C. for 1 hour. A separate oven dried 3 necked 24/40 2 L round-bottom flask is equipped with a mechanical stirrer, a septum and a nitrogen inlet. The flask is flushed with nitrogen then charged with 16 g of deuterated 4-iso-propyl($d_7$)benzenesulfonamide, (56)/Scheme 9, and 300 mL of anhydrous dimethyl sulfoxide. The stirrer is started and a 162 mL of a 1.0 M solution of lithium bis(trimethylsilylamide) in THF is slowly added (to control mildly exothermic reaction) via a syringe through the septum. After addition is complete, the reaction mixture is stirred at room temperature for 30 minutes more. The contents of the first reaction mixture including a white precipitate in it are then slowly transferred to the stirred solution of the deprotonated deaerated isopropyl($d_7$)benzenesulfonamide in the second reaction flask via a wide diameter cannula. The combined reaction mixture is then stirred for additional 12 hours under a nitrogen atmosphere. The reaction is then quenched with 1.0 N HCl and the larger portion of the volatile solvents are removed in vacuo. The residue is partitioned between ethyl acetate and 1.0 N HCl, then the organic layer is separated, washed with saturated aqueous sodium chloride (NaCl), dried with magnesium sulfate ($MgSO_4$), filtered and evaporated in vacuo. The residue is purified on a silica gel (3 kg; 70-230 mesh) chromatography column (15 cm×150 cm) eluted with (90:10:1 solvent mixture of $CH_2Cl_2$, $CH_3OH$, $NH_4OH$). Combination of the purified fractions and evaporation of the solvent in vacuo produces 18.3 g of the title compound. Expected $^1H$ NMR (400 MHz, $CD_3OD$, ppm): δ 0.88 (t, J=7.60 Hz, 3H), 1.24 (d, J=7.0 Hz, 3H), 1.25 (t, J=7.0 Hz, 3H), 1.25 (t, J=7.0 Hz, 3H), 1.55-1.60 (m, 2H), 2.59-2.66 (m, 2H), 2.97 (br m, 1H), 3.83 (s, 3H), 5.52 (s, 1H), 5.97 (s, 2H), 6.50 (d, J=8.80 Hz, 1H), 6.80 (d, J=8.0 Hz, 1H), 6.89 (d, J=1.60 Hz, 1H), 6.94 (dd, J=2.00, 8.00 Hz, 1H), 7.14 (d, J=8.80 Hz, 2H), 7.59 (dd, J=2.20, 8.80 Hz, 1H), 7.75 (d, J=2.20 Hz, 1H), 7.79 (d, J=8.80 Hz, 2H).

Preparation of N-(4-isopropyl($d_7$)benzenesulfonyl)-α-(4-carboxy-2-n-propylphenoxy)-3,4-methylenedioxyphenylacetamide Dipotassium Salt To a solution of 18.3 g of the product, N-(4-iso-propylbenzenesulfonyl)-α-(4-carbomethoxy-2-n-propylphenoxy)-3,4-methylenedioxyphenylacetamide, dissolved in 100 mL of methanol is added a solution of 6.6 g of potassium hydroxide (KOH) in 25 mL of water and the reaction mixture is stirred at 60° C. under a nitrogen atmosphere. TLC analysis (80:15:1=$CHCl_3$, $CH_3OH$, $NH_4OH$) indicated that ester hydrolysis is complete within 6 hours. The reaction mixture is cooled to room temperature, diluted with 100 mL of water, filtered through a 0.45 micron filter and then divided into two equal volume portions. The fractions are individually desalted and purified on a Water Millipore Delta Prep 3000 liquid chromatograph equipped with an M1000 Prep-Pak module containing a 47×300 mm Delta-Pak C18 15 μm 100 A column cartridge. Two solvent reservoirs are employed: solvent system A (95:5=water:acetonitrile), and solvent system B (5:95=water:acetonitrile), and the column effluent is monitored simultaneously at 210 and 280 nm with a Waters model 490 UV-visible detector. Each fraction is pump-injected onto the column and desalted by elution (50 mL/minute) with several column volumes of solvent system A. A gradient elution is then started with 100% solvent system A-0% solvent system B and reached after 30 minutes 50% solvent system A-50% solvent system B, and the fractions are collected with an ISCO Foxy 200 fraction collector. The purified fractions are combined in round-bottom flasks, frozen in a −78° C. dry ice-acetone bath, and lyophilized. Combination of the purified product yields 18.7 g of the tile compound as a white lyophilized powder. Expected $^1H$ NMR (400 MHz, $CD_3OD$, ppm): δ 0.88 (t, J=7.20 Hz, 3H), 1.21 (d, J=7.00 Hz, 3H), 1.22 (d, J=7.00 Hz, 3H), 1.56-1.63 (m, 2H), 2.52-2.59 (m, 1H), 2.67-2.74 (m, 1H), 2.91 (br m, 1H), 5.33 (s, 1H), 5.92 (d, J=1.20 Hz, 1H), 5.93 (d, J=1.20 Hz, 1H), 6.72 (d, J=8.50 Hz, 1H), 6.76 (d, J=8.50, 1H), 7.04 (d, J=7.50 Hz, 1H), 7.05 (s, 1H), 7.21 (d, J=8.50 Hz, 2H), 7.64 (dd, J=2.00, 8.50 Hz, 1H), 7.67 (d, J=8.50 Hz, 2H), 7.73 (d, J=2.00 Hz, 1H).

Preparation of N-(4-iso-propyl($d_6$)benzenesulfonyl)-α-(4-carbomethoxy-2-n-propylphenoxy)-3,4-methylenedioxyphenylacetamide The title compound (deuterated $d_6$-isopropyl analog) is prepared by using the synthetic method (procedure) described above for the preparation of the corresponding deuterated $d_7$ analog), N-(4-iso-propyl($d_7$)benzenesulfonyl)-α-(4-carbomethoxy-2-n-propylphenoxy)-3,4-methylenedioxyphenylacetamide.

Preparation of N-(4-isopropyl($d_6$)benzenesulfonyl)-α-(4-carboxy-2-n-propylphenoxy)-3,4-methylenedioxyphenylacetamide Dipotassium Salt The title compound (deuterated $d_6$-isopropyl analog) is prepared by using the synthetic method (procedure) described above for the preparation of the corresponding deuterated $d_7$ analog), N-(4-isopropyl($d_7$)benzenesulfonyl)-α-(4-carboxy-2-n-propylphenoxy)-3,4-methylenedioxyphenylacetamide dipotassium salt.

Preparation of N-(4-iso-propyl($d_7$)benzenesulfonyl)-α-(4-carbomethoxy-2-n-propyl($d_5$)phenoxy)-3,4-methylenedioxyphenylacetamide The title compound is prepared by using the synthetic methods described above for the preparation of the deuterated compounds above, N-(4-iso-propyl($d_7$)benzenesulfonyl)-α-(4-carbomethoxy-2-n-propylphenoxy)-3,4-methylenedioxyphenylacetamide.

Preparation of N-(4-isopropyl($d_7$)benzenesulfonyl)-α-(4-carboxy-2-n-propyl ($d_5$) phenoxy)-3,4-methylenedioxyphenylacetamide Dipotassium Salt The title compound is prepared by using the synthetic methods described above for the preparation of the deuterated compound, N-(4-isopropyl($d_7$)benzenesulfonyl)-α-(4-carboxy-2-n-propylphenoxy)-3,4-methylenedioxyphenylacetamide dipotassium salt.

Preparation of N-(4-iso-propyl($d_6$)benzenesulfonyl)-α-(4-carbomethoxy-2-n-propyl($d_5$)phenoxy)-3,4-methylenedioxyphenylacetamide The title compound is prepared by using the synthetic methods described above for the preparation of the deuterated compounds above, N-(4-iso-propyl($d_7$)benzenesulfonyl)-α-(4-carbomethoxy-2-n-propylphenoxy)-3,4-methylenedioxyphenylacetamide.

Preparation of N-(4-isopropyl($d_6$)benzenesulfonyl)-α-(4-carboxy-2-n-propyl ($d_5$) phenoxy)-3,4-methylenedioxyphenylacetamide Dipotassium Salt The title compound is prepared by using the synthetic methods described above for the preparation of the deuterated compound, N-(4-isopropyl($d_7$)benzenesulfonyl)-α-(4-carboxy-2-n-propylphenoxy)-3,4-methylenedioxyphenylacetamide dipotassium salt.

Preparation of N-(4-iso-propylbenzenesulfonyl)-α-(4-carbomethoxy-2-n-propylphenoxy)-3,4-methylenedioxyphenylacetamide Step A: Preparation of ethyl α-(4-carbomethoxy-2-n-propylphenoxy)-3,4-methylenedioxyphenylacetate To a nitrogen flushed 5 L three neck round bottom flask fitted with a mechanical stirrer, condenser, and a nitrogen inlet is charged 239 g of methyl 4-hydroxy-3-n-propylbenzoate (partially deuterated n-propyl or undeuterated), 372 g of ethyl α-bromo-3,4-methylenedioxyphenylacetate from above, 172.5 g of anhydrous potassium carbonate ($K_2CO_3$), and 1.25 L of acetone. The mixture is refluxed with vigorous stirring for 9 hours, The suspension is allowed to cool to ambient temperature and stirred overnight. The mixture diluted with 1.5 L of diethyl ether, cooled to 0° C., and filtered through diatomaceous earth (Super-Cel/$SiO_2$ available from Sigma-Aldrich). The filter cake is washed with diethyl ether (ether) and the combined filtrate concentrated. The residue is redissolved in ether and the organic layer is washed once with 1N HCl, saturated aqueous solution of sodium bicarbonate ($NaHCO_3$), 10% sodium bisulfite aqueous solution, saturated aqueous solution of sodium chloride (brine, aq. NaCl), dried over anhydrous magnesium sulfate, treated with charcoal and filtered through silica gel. The pale yellow solution is obtained, which is then concentrated to 511 g of a thick yellow oil which is used without purification in the next step. NMR spectrum is consistent with the title compound. Expected $^1$H NMR (300 MHz, $CDCl_3$, ppm): δ 0.95 (t, J=7.3 Hz, 3H), 1.17 (t, J=7.1 Hz, 3H), 1.61-1.81 (m, 2H), 2.63-2.80 (m, 2H), 3.85 (s, 3H), 4.07-4.23 (m, 2H), 5.58 (s, 1H), 5.96 (s, 2H), 6.71 (d, J=8.5, 1H), 6.76 (d, J=8.0 Hz, 1H), 7.02 (d, d, J=8.0 Hz, 1.7 Hz), 7.05 (d, =1.7 Hz, 1H), 7.79 (d, d, J=8.5, 2.2 Hz, 1H), 7.84 (d, J=2.2 Hz, 1H).

Step B: Preparation of α-(4-carbomethoxy-2-n-propylphenoxy)-3,4-methylenedioxyphenylacetic Acid To a nitrogen flushed 5 L 3 neck round bottom flask equipped with a mechanical stirrer, a dropping funnel, and a nitrogen inlet is added 511 gram (g) of the crude product obtained in the step A above, and 1.5 L of methanol. 370 mL of 5N aqueous solution of sodium hydroxide (NaOH) is added over a 15-20 minute period via an additional funnel. The reaction mixture is stirred at room temperature for one hour until the starting material is completely consumed as indicated by TLC analysis ($CH_2Cl_2$:$CH_3OH$, $NH_4OH$=90:10:1). The reaction mixture is neutralized with 310 mL of 6N HCl, with gentle shaking, and the organic solvent is removed in vacuo. The residue is dissolved in diethyl ether and extracted with a combination of aqueous sodium hydroxide (aq. NaOH), and sodium bicarbonate (aqueous $NaHCO_3$). The aqueous layer is extracted with ether and the combined organic layer is washed with aqueous $NaHCO_3$. The aqueous layer is acidified with hydrochloric acid (HCl) and extracted with ether. The ethereal solution is dried with magnesium sulfate, filtered and concentrated to give 520 g of the title compound as a viscous orange oil. NMR spectral analysis reveals the crude product contains 15% of ether, so the actual yield of the pure title compound is 442 g (96.5%). Expected $^1$H NMR (300 MHz, $CD_3OD$, ppm): δ0.93 (t, J=7.4 Hz, 3H), 1.56-1.77 (m, 2H), 2.68 (t, 2H), 3.84 (s, 3H), 5.57 (s, 1H), 5.95 (s, 2H), 6.42 (bs, 1H), 6.71 (d, J=8.5 Hz, 1H), 6.79 (d, J=7.9 Hz, 1H), 6.99-7.05 (m, 2H), 7.78 (d, d, J=8.5, 2.2 Hz, 1H), 7.82 (d, J=2.2, 1H).

Step C: Preparation of N-(4-iso-propyl($d_7$)benzenesulfonyl)-α-(4-carbomethoxy-2-n-propylphenoxy)-3,4-methylenedioxyphenylacetamide Potassium Salt To a nitrogen flushed 100 mL three neck round bottom flask equipped with a condenser, dropping funnel and a nitrogen inlet is added 10 mL of tetrahydrofuran (THF) and 3.6 g of carbonyl diimidazole (CDI), The mixture is heated to reflux and a solution of 6.84 g of carboxylic acid from step B and 10 mL of THF is added dropwise over a period of 5 minutes. The reaction is monitored for conversation of the phenoxyacetic acid to the acyl imidazole by NMR. A THF solution (3 mL) of additional 0.9 g of CDI is added cautiously. The solution is cooled to 0° C.-5° C. and 3 g of 4-isopropyl($d_7$)benzenesulfonamide [compound 56 (R=D) in scheme 9)] is added as a solid in one portion and the solution allowed to stand 15 minutes. DBU (2.4 mL, 2.44 g) is added dropwise over 5 minutes resulting in an exothermic reaction to 45° C. The reaction is allowed to stand at room temperature for 2 hours without any form of stirring and then concentrated in vacuo. The residue is partitioned between 30 mL 2.5 N HCl and 30 mL of ether. The aqueous layer is extracted twice with 15 mL of ether, and the combined organic extracts (organic layer or organic phase) are washed with 2N HCl and saturated aqueous solution of potassium bicarbonate ($KHCO_3$). Additional 10 mL of saturated aqueous solution of $KHCO_3$ is added and the resulting mixture is stirred for a few to several hours. The resulting thick suspension is filtered and the cake washed with 5 mL of water followed by 10 mL of ether. The product is then slurried in the funnel with additional ether and sucked dry producing 7.6 g of a tan solid. This tan solid is treated with 10 mL of ethyl acetate and 5 mL of saturated $KHCO_3$ aqueous solution. The slurry is stirred for 15 minutes at room temperature, diluted with 30 mL of ether and stirred for 1 hour. The product is filtered, washed with 5 mL of water and 10 mL of ether and dried in vacuo to yield 6 g of the title compound as a white crystalline solid. A second crop of 0.5 g is obtained from mother liquors to result in combined yield of 6.5 g of the title compound. Expected $^1$H NMR (300 MHz, $CD_3OD$, ppm): δ 0.88 (t, J=7.4 Hz, 3H), 1.21 (br m, 6H), 1.52-1.66 (m, 2H), 2.50-2.76 (m, 2H), 2.90 (br m, 1H), 3.84 (s, 3H), 5.35 (s, 1H), 5.94 (s, 2H), 6.69 (d, J=8.6 Hz, 1H), 6.76 (d, J=8.5 Hz, 1H), 7.04 (m, 2H), 7.20 (d, J=8.4 Hz, 2H), 7.61 (dd, J=8.5 Hz, 2.20 Hz, 1H), 7.67 (d, J=8.4, 2H), 7.71 (d, J=2.1 Hz, 1H).

N-(4-iso-propyl($d_7$)benzenesulfonyl)-α-(4-carboxy-2-n-propylphenoxy)-3,4-methylenedioxyphenylacetamide Dipotassium Salt Method A:

Step A: Preparation of N-(4-iso-propyl($d_7$)benzenesulfonyl)-α-(4-carboxy-2-n-propylphenoxy)-3,4-methylenedioxyphenylacetamide Dipotassium Salt A mixture of 4 g of N-(4-iso-propyl($d_7$)benzenesulfonyl)-α-(4-carboxy-2-n-propylphenoxy)-3,4-methylenedioxyphenylacetamide (product of step C of the procedure described above), 10 mL of 1.0 N potassium hydroxide (KOH) in methanol ($CH_3OH$) and 10 mL of water is stirred at 60° C. under a nitrogen atmosphere for 2 hours. The reaction is monitored by TLC analysis (solvent for development of TLC is $CH_2Cl_2$:$CH_3OH$:$NH_4OH$=90:10:1). The reaction mixture is concentrated in vacuo using rotary evaporator. 50 mL of isopropanol is added and the solution is concentrated again using rotary evaporator. The resulting residue is flushed with 50 mL of isopropanol to begin crystallization. The slurry is concentrated to 25-30 mL of volume and allowed to cool down to 30° C., then filtered and washed with 5 mL of isopropanol and 15 mL of ether. The product is dried to produce 3.5 g of the title compound, dipotassium salt, as a white crystalline solid. A second crop of 0.5 g is obtained by cooling the mother liquor (filtrate). The white solid material is recrystallized as described below:

The solid material (4 g) obtained above is dissolved in 70 mL of absolute ethanol at reflux, and then filtered while hot. Water (1.5 mL) is added and the resulting solution is cooled to 0° C. and then allowed to stand overnight at 0° C. for recrystallization of the product. The product is filtered, washed with ethanol and then air-dried. The title compound, dipotassium salt, is obtained as a white crystalline solid (3.85 g) in excellent yield. Expected $^1$H NMR (400 MHz, $CD_3OD$, ppm): δ 0.88 (t, J=7.2 Hz, 3H), 1.21 (d, J=7.0 Hz, 3H), 1.22 (d, J=7.0 Hz, 3H), 1.56-1.63 (m, 2H), 2.52-2.59 (m, 1H), 2.67-2.74 (m, 1H), 2.91 (br m, 1H), 5.33 (s, 1H), 5.92 (d, J=1.2 Hz, 1H), 5.93 (d, J=1.2 Hz, 1H), 6.72 (d, J=8.5 Hz, 1H), 6.76 (d, J=8.5 Hz, 1H), 7.04 (d, J=7.5 Hz, 1H), 7.05

(s, 1H), 7.21 (d, J=8.5 Hz, 2H), 7.64 (dd, J=2.0, 8.5 Hz, 1H), 7.67 (d, J=8.5 Hz, 2H), 7.73 (d, J=2.0 Hz, 1H).

Method B:

Step A: Preparation of N-(4-isopropyl($d_7$)benzenesulfonyl)-α-(4-carboxy-2-n-propylphenoxy)-3,4-methylenedioxyphenylacetamide A mixture of 4 g of N-(4-iso-propylbenzenesulfonyl)-α-(4-carboxy-2-n-propylphenoxy)-3,4-methylenedioxyphenylacetamide, 10 mL of 1.0 N KOH in methanol and 10 mL of water is stirred at 60° C. for 2 hours under a nitrogen atmosphere. The reaction mixture is allowed to attain room temperature and then concentrated using rotary evaporator. The concentrate is acidified with 10 mL of 2N HCl and extracted with 125 mL of a mixture of solvent comprised of ether:ethyl acetate:methylene chloride (5:1:1), then with 60 mL of ethyl acetate/methylene chloride (1;2) solvent mixture. The organic layer (organic extract) is washed sequentially with 5 mL of 2N HCl, three times with 10 mL of water and dried with anhydrous magnesium sulfate ($MgSO_4$), filtered, and concentrated, to produce a white slurry which is diluted with 20 mL of hexanes and then cooled to 0° C. and allowed to stand to ensue crystallization of the product. After a few hours, the product is filtered and air dried to yield 3.3 g of the title compound as a white crystalline solid. Expected $^1$H NMR (400 MHz, $CD_3OD$, ppm): δ 0.88 (t, J=7.2 Hz, 3H), 1.21 (d, J=7 Hz, 3H), 1.22 (d, J=7 Hz, 3H), 1.56-1.63 (m, 2H), 2.52-2.59 (m, 1H), 2.67-2.74 (m, 1H), 2.91 (bm, 1H), 5.33 (s, 1H), 5.92 (d, J=1.2 Hz, 1H), 5.93 (d, J=1.2 Hz, 1H), 6.72 (d, J=8.5 Hz, 1H), 6.76 (d, J=8.5 Hz, 1H), 7.04 (d, J=7.5 Hz, 1H), 7.05 (s, 1H), 7.21 (d, J=8.5 Hz, 2H), 7.64 (dd, J=2.0 Hz, 8.5 Hz, 1H), 7.67 (d, J=8.5 Hz, 2H), 7.73 (d, J=2.0 Hz, 1H).

Step B: Preparation of N-(4-iso-propyl($d_7$)benzenesulfonyl)-α-(4-carboxy-2-n-propylphenoxy)-3,4-methylenedioxyphenylacetamide Dipotassium Salt To 3 g of phenylacetic acid from step A is added 55 mL of absolute ethanol and stirred. A solution of 1.0 N KOH in methanol (15 mL) is added to ethanolic solution of the acid and the mixture gently warmed to 50° C. to result in a clear solution. The solution is then cooled to 0° C. and 10 mL of ether is added and the resulting suspension is filtered to give solid material that is dried to produce 3.25 g of the title compound as a white crystalline solid. A second crop 0.42 g of the title compound is obtained by concentrating the mother liquor and then diluting it with 20 mL of ether, then filtering, and recrystallizing the solid from 98% ethanol to a total yield of 3.67 g of the dipotassium salt.

N-(4-isopropylbenzenesulfonyl)-α-(4-carboxy-2-n-propylphenoxy)-3,4-methylenedioxyphenylacetamide Dipotassium Salt

Step A: Preparation of N-(4-isopropylbenzenesulfonyl)-α-(4-carboxy-2-n-propylphenoxy)-3,4-methylenedioxyphenylacetamide di-S-(−)-α-methylbenzylamine Salt 30 g of α-(4-carbomethoxy-2-n-propylphenoxy)-3,4-methylenedioxyphenylacetate acid is dissolved in 500 mL of isopropanol, and 14.5 g of S-(−)-α-methylbenzyl amine is added and the resulting solution is allowed to stand at room temperature overnight. The mixture is filtered and the filter cake washed with isopropanol to obtain a solid material. The solid is recrystallized 5 more times from isopropanol yielding 4.1 g of the title compound.

Step B: Preparation of N-(4-isopropyl($d_7$)benzenesulfonyl)-α-4-carboxy-2-n-propylphenoxy)-3,4-methylenedioxyphenylacetamide Dipotassium Salt The α-methylbenzylamine salt from step A is partitioned between ethyl acetate and sodium bisulfite ($NaHSO_3$), dried with $MgSO_4$, filtered and then concentrated. The residue is dissolved in methanol-water at room temperature, and basified with 12 mL of 1 N NaOH in methanol, diluted with water and filtered. The solution is desalted and purified on a Waters Millipore Delta Prep 3000 liquid chromatograph equipped with a M 1000 Prep-Pak module containing a 47×300 mm Delta-Pak C18 15 mm 100 A column cartridge. Two solvent reservoirs are employed: solvent system A (95:5=water:acetonitrile), and the column effluent is monitored simultaneously at 210 and 280 nm with a Waters model 490 UV-visible detector. Each fraction is pump-injected onto the column and desalted by elution (50 mL/min) with several column volumes of solvent system A. A gradient elution is then started with 100% solvent system A-0% solvent system B and reached after 30 minutes 50% solvent system A-50% solvent system B, and the fractions are collected with an ISCO Foxy 200 fraction collector. The purified fractions are combined in round bottom flasks, frozen in a −78° C. dry ice-acetone bath, and lyophilized. Combination of the purified product yields the title compound as a white lyophilized powder. Expected 1H NMR (400 MHz, $CD_3OD$, ppm): δ 0.88 (t, J=7.2 Hz, 3H), 1.21 (d, J=7.0 Hz, 3H), 1.22 (d, J=7 Hz, 3H), 1.56-1.63 (m, 2H), 2.52-2.59 (m, 1H), 2.67-2.74 (m, 1H), 2.91 (br m, 1H), 5.33 (s, 1H), 5.92 (d, J=1.2 Hz, 1H), 5.93 (d, J=1.2 Hz, 1H), 6.72 (d, J=8.5 Hz, 1H), 6.76 (d, J=8.5 Hz, 1H), 7.04 (d, J=7.5 Hz, 1H), 7.05 (s, 1H), 7.21 (d, J=8.5 Hz, 2H), 7.64 (dd, J=2 Hz, 8.5 Hz, 1H), 7.67 (d, J=8.5 Hz, 2H), 7.73 (d, J=2.0 Hz, 1H).

N-(4-iso-propyl-$d_7$-benzenesulfonyl)-α-(4-carbomethoxy-2-n-propyl-$d_7$-phenoxy)-3,4-methylenedioxyphenylacetamide The titled deuterated compound is also prepared directly from an undeuterated precursor using an efficient and extensive deuterium incorporation using a deuterium gas ($D_2$)-free, totally catalytic deuterium incorporation by heating a reaction mixture of the substrate with a catalytic (10% by weight of substrate) amount of 10% palladium on carbon in $D_2O$ under hydrogen atmosphere (in a sealed tube) at 160° C. for 24 hours [Ref. Sajiki, H, et al. Efficient C—H/C-D exchange reaction on the alkyl side chain of aromatic compounds using heterogeneous Pd/C in $D_2O$·, Organic Letters (Org. Lett), 2004, 6 (9), 1485-1487).

The product shown below is then hydrolyzed with aqueous $KOH/CH_3OH$ solution as described above.

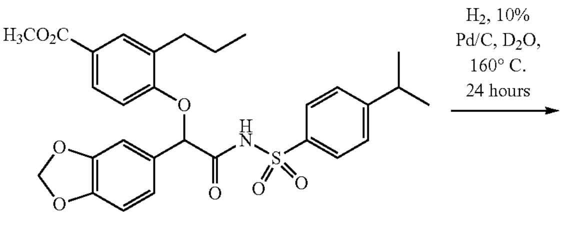

-continued

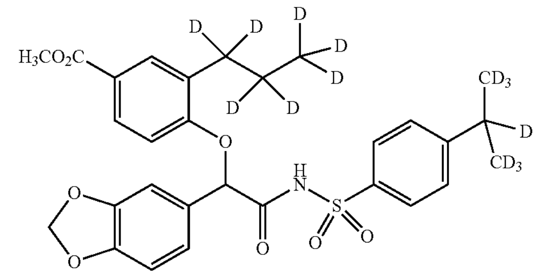

Similarly other deuterium containing products shown below are prepared directly using the catalytic hydrogenation in $D_2O$ (shown below) from the appropriate precursors whose syntheses are described above.

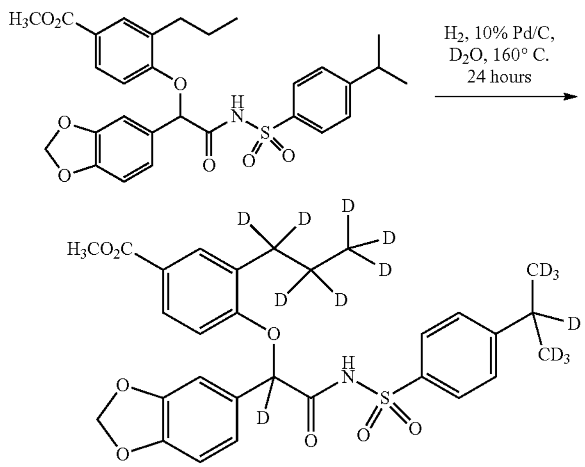

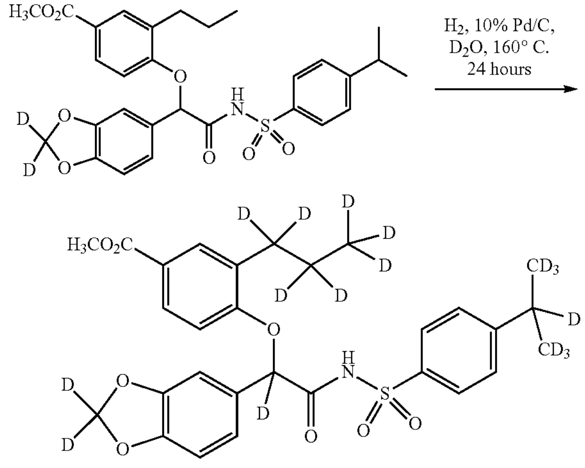

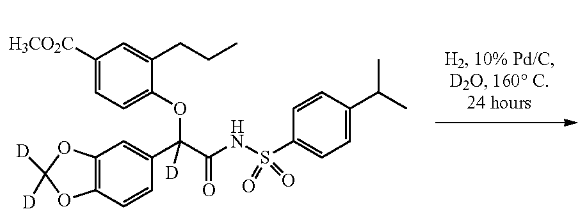

-continued

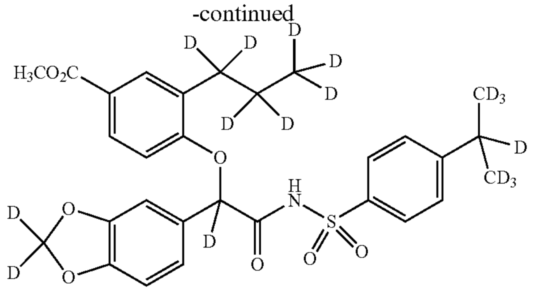

The deuterated products shown above are then hydrolyzed with aqueous $KOH/CH_3OH$ or $NaOH/CH_3OH$ solution to the corresponding carboxylic acids and as described above.

The hydrolyzed acid-sulfonamides are then converted into their desired pharmaceutical salts as described above.

Those skilled in the art will recognize or be able to ascertain using no more than routine experimentation, numerous equivalents to the specific reagents can be utilized to produce compounds of the invention. Numerous modifications and variations of the present invention are possible and therefore it is understood that within the scope of the appended claims, the invention may be practiced otherwise that as specifically described herein. Other aspects, advantages and modifications are within the scope of the invention.

Endothelin Receptor Binding Assays:

The binding of the novel compounds of this invention to the endothelin receptor is determined in accordance with the assay described in Ambar et al. Biochem. Biophys. Res. Commun., 1989, 158, 195-201; and Khoog et al. FEBS Letters, 1989, 253, 199-202.

The endothelins (ETs) have a number of potent effects on various cells, and exert their actions by interacting with specific receptors present on cell membranes. The compounds described in the present invention act as antagonists of ET at the receptors. In order to identify ET antagonists and determine their efficacy in vitro, the following three ligand receptor assays are established.

Receptor Binding Assay Using Cow Aorta Membrane Preparations:

Thoracic aortae is obtained from freshly slaughtered calves and brought to the lab on wet ice. The adventitia is removed and the aorta is opened up lengthwise. The lumenal surface of the tissue is scrubbed with cheesecloth to remove the endothelial layer. The tissue is ground in a meat grinder, and suspended in ice-cold 0.25 M sucrose, 5 mM tris-HCL, pH 7.4, containing 0.5 mg/mL. leupeptin and 7 mg/mL pepstatin A. Tissue is homogenized twice and then centrifuged for 10 minutes at 750×g at 4° C. The supernatant is filtered through cheesecloth and centrifuged again for 30 minutes at 48,000×g at 4° C. The pellet thus obtained is resuspended in the buffer solution described above (including the protease inhibitors), and aliquots are quick-frozen and stored at −70° C. until use. Membranes are diluted into 50 mM potassium phosphate (KPi), 5 mM EDTA pH 7.5 containing 0.01% human serum albumin. Assays are done in triplicate. Test compounds and 100 pM [$^{125}$I]-endothelin-1 (2000-2200 Ci/mmole, obtained from New England Nuclear or Amersham) are placed in a tube containing this buffer, and the membranes prepared above are added last. The samples are incubated for 60 minutes at 37° C. At the end of this incubation, samples are filtered onto prewetted (with 2% BSA in water) glass fiber filter pads and washed with 150 mM NaCl, 0.1% BSA. The filters are assayed for [$^{125}$I]- endotheline-1 radioactivity in a gamma counter. Nondisplaceable binding [$^{125}$I]-endotheline-1 is measured in the presence of 100 mM unlabelled endothelin-1 [Endothelin-1 (ET-1)] is purchased from Peptides International (Louisville, KY). $^{125}$I-ET-1 (2000 Ci/mMol) is purchased from Amersham (Arlington Heights, IL, GE Health). Specific binding is total binding minus nondisplaceable binding. The inhibitory concentration ($IC_{50}$) which gives 50% displacement of the total specifically bound [125I]-Endothelin-1 is presented as a measure of the efficacy of such compounds as endothelin (ET) antagonists.

Receptor Binding Assay Using Rat Hippocampal Membrane Preparation:

Rat hippocampi is obtained from freshly sacrificed male Sprague-Dawley rats and placed in ice cold 0.25 M sucrose, 5 mM tris-HCL, pH 7.4 containing 0.5 mg/mL leupeptin, 7 mg/mL pepstatin A. Hippocampi is weighed and placed in a Dounce homogenizer with 2.5 volumes (wet weight to volume) ice-cold sucrose buffer in the presence of protease inhibitors. Hippocampi is homogenized using a Denounce (glass-glass) homogenizer with type A pestle, with homogenizer in ice. Tissue homogenate is centrifuged at 750×g for 10 min at 4° C. Supernatant is filtered through dampened cheesecloth, and centrifuged again at 48000×g for 30 minute at 4° C. Pellets are resuspended in sucrose buffer with protease inhibitors. Aliquots of this preparation is quick frozen and stored at −70° C. until use. Membranes are diluted into 50 mM KPi, 5 mM EDTA pH 7.5 containing 0.01% human serum albumin. Assays are done in triplicate. Test compounds and 25 pM [$^{125}$I]-endothelin-1 (2000-2200 Ci/mmole, obtained from New England Nuclear or other suppliers e.g. Amersham, now GE Health) are placed in a tube containing this buffer, and the membranes prepared above are added last. The samples are incubated for 60 minute at 37° C. At the end of this incubation, samples are filtered onto prewetted (with 2% BSA in water) glass fiber filter pads and washed with 150 mM NaCl, 0.1% BSA. The filters are assayed for $^{125}$I radioactivity in a gamma counter. Nondisplaceable binding of [$^{125}$I]-endothelin-1 is measured in the presence of 100 nM unlabelled endothelin-1 [ET-1] is purchased from Peptide International (Luisville, KY). $^{125}$I-ET-1 (2000 Ci/mMol) is purchased from Amersham (or now GE Healthcare/GE Corporation) or any other supplier. Specific binding is total binding minus nondisplaceable binding. The inhibitory concentration ($IC_{50}$) which gives 50% displacement of the total specificity bound [$^{125}$I]-endothelin-1 is presented as a measure of the efficacy of such compounds as endothelin antagonists.

Receptor Binding Assay Using Cloned Human ET Receptors Expressed in Chinese Hamster Ovary Cells:

Both endothelin (ET) receptor subtypes are cloned from a human cDNA library and are individually expressed in Chinese Hamster Ovary (CHO) cells. CHO cells are harvested by addition of 126 mM NaCl, 5 mM KCl, 2 mM EDTA, 1 mM $NaH_2PO4$, 15 mM glucose, 10 mM tris/HEPES pH 7.4. CHO cells are centrifuged at 250×g for 5 minutes. The supernatant is aspirated off, and the cells are resuspended in the 50 mM KPi, 5 mM EDTA pH 7.5 containing 0.01% human serum albumin. Assays are done in triplicate. Test compounds and 25-100 pM [$^{125}$I]-endothelin-1 (2000-2200 Ci/mmole, obtained from New England Nuclear, GE Healthcare of GE Corporation, or any other supplier) are placed in a tube containing 50 mM KPi, 5 mM EDTA pH 7.5 containing 0.01% human serum albumin, and the cells prepared above are added last. The samples are incubated for 60 minutes at 37° C. At the end of this incubation, samples are filtered onto prewetted (with 2% BSA in water) glass fiber filter pads and washed with 150 mM NaCl, 1% BSA.

The filters are assayed for $^{125}$I radioactivity in a gamma counter. Nondisplaceable binding of [$^{125}$I]-endothelin-1 is measured in the presence of 100 nM unlabelled endothelin-1 [Endothelin-1 (ET-1) is purchased from Peptides International (Louisville, KY). $^{125}$I-ET-1 (2000 Ci/mMol) is purchased from GE Healthcare/GE Corporation)]. Specific binding is total binding minus nondisplaceable binding. The inhibitory concentration ($IC_{50}$) which gives 50% displacement of the total specifically bound [$^{125}$I]-endothelin is prepared as a measure of the efficacy of such compounds as endothelin antagonists.

The binding assays described above are used to evaluate the potency of interaction of representative compounds of the invention with endothelin receptors. To determine whether these compounds are endothelin antagonists, assays which measure the ability of the compounds to inhibit endothelin-stimulated phosphatidylinositol hydrolysis are established. Rat uterus contains predominantly one of the known endothelin receptor subtypes ($ET_A$).

Phosphatidylinositol Hydrolysis Assays Using Rat Uterine Slices:

Diethylstilbestrol primed female Sprague-Dawley rats are sacrificed and their uteri are collected, dissected of fat and connective tissue and minced. Minced tissue is added to oxygenated (85% $O_2$, 5% $CO_2$) 127 mM NaCl, 25 mM $NaHCO_3$, 10 mM Glucose, 2.5 mM KCl, 1.2 mM $KH_2PO_4$, 1.2 mM $MgSO_4$, 1.8 mM $CaCl_2$. To the tissue mince, 1.2 mM myo-[$^3$H]-inositol is added. The mince is incubated 90 minutes at 37° C., with constant oxygenation. After incubation, the loaded tissue mince is washed 5× times with the same oxygenated buffer to remove excess radiolabelled inositol. The tissue mince is resuspended in the above buffer, containing 10 mM LiCl, aliquoted into tubes, and 3 nM endothelin-1 with and without test compounds is added to start the assay. Assays are done in quadruplicate. Samples are incubated at 37° C. under blowing $O_2$ in a hooded water bat for 30 minutes. Reaction is stopped by addition of trichloroacetic acid to 6% concentration. Samples are sonicated for 10 minutes, centrifuged 20 minutes, then trichloroacetic acid is extracted with water-saturated ethyl ether. An aliquot of each sample is neutralized and diluted by addition of 50 mM tris-HCL pH 7.4. A 100 mL aliquot of this solution is assayed for radioactivity in a beta counter. The diluted neutralized sample is applied to Dowex 1×8-formate columns, washed with water, then washed with 60 mM ammonium formate, 5 mM sodium tetraborate. Samples are eluted with 200 mM ammonium formate, 5 mM sodium tetraborate. The radioactivity of each eluted sample is measured in a beta counter. Radioactivity is normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Sarafotoxin S6c is a member of the endothelin family which binds preferentially to one of the known endothelin receptor subtypes ($ET_B$).

Phosphatidylinositol Hydrolysis Assays Using Rat Lung Slices:

Male Sprague-Dawley rats are sacrificed and their lings are collected, dissected of fat and connective tissue and minced. Minced tissue is added to oxygenated (95% $O_2$, 5% $CO_2$) 127 mM NaCl, 25 mM $NaHCO_3$, 10 mM glucose, 2.5 mM KCl, 1.2 mM $KH_2PO_4$, 1.2 mM $MgSO_4$, 1.8 mM $CaCl_2$. To the tissue mince 1.2 μM myo-[$^3$H]-inositol is added. The mince is incubated 60 minutes at 37° C., with constant oxygenation. After incubation, loaded tissue mince is washed five times (5× times) with the same oxygenated buffer to remove excess radiolabelled inositol. Tissue mince is resuspended in the above buffer, containing 10 mM LiCl, aliquoted into tubes, and 3 nM sarafotoxin S6c with and without test compounds is added to start the assay. Assays are done in quadruplicate. Samples are incubated at 37° C. under blowing $O_2$ in a hooded water bath for 30 minutes. Reaction is stopped by addition of 0.5 mL of 18% trichloroacetic acid to 6% concentration. Samples are sonicated for 10 minutes, centrifuged 20 minutes, then trichloroacetic acid is extracted with water-saturated ethyl ether. An aliquot of each sample is neutralized and diluted by addition of 50 mM tris-HCL pH 7.4. A 100 mL aliquot of this solution is assayed for radioactivity in a beta counter. The diluted neutralized sample is applied to Dowex 1×8-formate columns, washed with water, then washed with 60 mM ammonium formate, 5 nM sodium tetraborate. Samples are eluted with 200 mM ammonium formate, 5 mM sodium tetraborate. Samples are eluted with 200 mM ammonium formate, 5 mM sodium tetraborate. The radioactivity of each eluted sample is measured in a beta counter. Radioactivity is normalized by dividing radioactivity in postcolumn sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Phosphatidylinositol Hydrolysis Assays Using Cloned Human Endothelin Receptors Expressed in Chinese Hamster Ovary Cells:

Both endothelin receptors ($ET_A$ and $ET_B$ receptors) are cloned from a human cDNA library and are individually expressed in Chinese Hamster Ovary (CHO) cells. CHO cells are loaded overnight by the addition of 1.2 μM myo-[$^3$H]-inositol to their growth medium. Cells are harvested by addition of 126 mM NaCl, 5 mM KCl, 2 mM EDTA, 1 mM $NaH_2PO4$, 15 mM glucose, 10 mM tris/HEPES pH 7.4. Cells are washed five times by centrifugation at 250×g for 5 minutes to remove excess radiolabelled inositol. The supernatant is aspirated off, and the cells are resuspended in the same oxygenated (95% $O_2$, 5% $CO_2$) buffer containing 10 mM LiCl, aliquoted into tubes, and 0.3 nM endotheline-1 with and without test compounds is added to start the assay. Assays are done in quadruplicate. Samples are incubated at 37° C. under blowing $O_2$ in a hooded water bath for 30 minutes. Reaction is stopped by addition of 0.5 mL 18% trichloroacetic acid to 6% concentration. Samples are sonicated for 10 minutes, centrifuged 20 minutes, the trichloroacetic acid is extracted with water-saturated ethyl ether. An aliquot of each sample is neutralized and diluted by addition of 50 mM tris-HCL pH 7.4. A 100 mL aliquot of this solution is assayed for radioactivity in beta counter. The diluted neutralized sample is applied to Dowex 1×8-formate columns, washed with water, then washed with water, then washed with 60 mM ammonium formate, and 5 mM sodium tetraborate. Samples are eluted with 200 mM ammonium formate, 5 mM sodium tetraborate. The radioactivity of each eluted sample is measured in a beta counter. Radioactivity is normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Using the methodology described above, representative compounds of this invention are evaluated and found to exhibit $IC_{50}$ values of at less than 50 μM (<50 μM) thereby demonstrating and confirming the utility of the compounds of this invention as effective endothelin antagonists.

Intravenous Effect of Endothelin-1 Receptor Antagonist, N-(4-isopropyl-$d_7$-benzenesulfonyl)-α-(4-carboxy-2-n-propylphenoxy)-3,4-methylenedioxyphenylacetamide Dipotassium Salt on Endothelin-1-Induced Changes in Diastolic and Uretheral Pressures in the Anesthetized Male Dog Methodology for Determining Whether an ET-1 Receptor Selective Antagonist could Inhibit the ET-1 Mediated Prostatic Urethral Contractions in a Mongrel Dog Model:

On separate days, two fasted male mongrel dogs (from commercial suppliers) weighing 11.0 and 12.4 kilograms (kg), are anesthetized with sodium pentobarbital at 35 mg/kg (i.v.) to effect, followed by 4 mg/kg/hr (i.v.) infusion. A cuffed endotracheal tube is inserted and each animal is ventilated with room air using a positive displacement large animal ventilator at a rate of 18 breaths/minute and an average tidal volume of 18 mL/kg body weight. Body temperature is maintained with a heating pad and heat lamp using a temperature controller and esophageal probe. Two catheters are placed in the aorta via the femoral arteries (one in each artery) for administration of endothelin or phenylephrine and for continuous direct monitoring of blood pressure and heart rate using a Statham blood pressure transducer (Spectramed) and a computer system (Modukar Instruments, Inc.). Two other catheters are placed in the vena cava via the femoral veins (one catheters in each vein) for administration of pentobarbital and N-(4-isopropyl ($d_7$)-benzenesulfonyl)-α-(4-carboxy-2-n-propylphenoxy)-3,4-methylenedioxyphenylacetamide dipotassium salt.

A supra-pubic incision approximately one-half inch lateral to the penis is made to expose the ureters, urinary bladder, prostate, and urethra. The dome of the bladder is retracted to facilitate dissection of the ureters. The ureters are cannulated with PE 90 and tied off to the bladder. Umbilical tape is passed beneath the urethra at the bladder neck and another piece of tape is placed approximately 1-2 cm distal to the prostate. The bladder is incised and a Micro-tip catheter transducer is advanced into the urethra. The neck of the bladder is ligated with the umbilical tape to hold the transducer. The bladder incision is sutured with 3-0 silk (purse string suture). The transducer is withdrawn until it is positioned in the prostatic urethra. The position of the Micro-tip catheter is verified by gently squeezing the prostate and noting the large change in urethral pressure prior to ligating the distal urethra.

Experimental Protocol:

Phenylephrine (10 μg/kg, intra-arterial) is administered and pressor effects on diastolic blood pressure (DBP) and intra-urethral pressure (IUP) is noted. When blood pressure returned to baseline, endothelin-1 (1 nmole/kg, intra-arterial) is administered. Changes in DBP and IUP are monitored for one hour and an ET-1 selective endothelin antagonist, such as the deuterated compound, N-(4-isopropyl($d_7$)

benzenesulfonyl)-α-(4-carboxy-2-n-propylphenoxy)-3,4-methylenedioxyphenyl-acetamide dipotassium salt (30 mg/kg, intra-venous), is administered. After 15 minutes, when blood pressure had stabilized, ET-1 is administered again, and inhibition of ET-1 induced effects are observed, noted and recorded. Phenylephrine is administered at the end of experiment to verify specificity for ET-1 blockade. The dogs are euthanized with an overdose of pentobarbital followed by saturated KCl.

The drugs utilized in the experiment described above are:

(1) Phenylephrine, HCl (PE) (Sigma Chemical Co.) is given at a volume of 0.05 mL/kg;

(2) Endothelin-1 (ET-1) (Human, Porcine, Canine, rat, Mouse, Bovine) is given at a volume of 0.05 mL/kg;

(3) ET-1 selective antagonist, such as the deuterated compound N-(4-isopropyl($d_7$)benzenesulfonyl)-α-(4-carboxy-2-n-propyl-$d_7$-phenoxy)-3,4-methylenedioxyphenyl-acetamide dipotassium salt, is given at a volume of 0.3 mL/kg.

All drugs are dissolved in isotonic saline solution.

Results

ET-1 elicited an initial depressor effect followed by a longer pressor effect. In one dog, the pressor effect is biphasic. The decrease in DBP in both dogs averaged 15 mmHg, while the peak pressor effect averaged 25 mmHg. The average ET-1 induced increase in IUP is 15 mmHg. Ten to 15 minutes after administration of N-(4-isopropyl-$d_7$-benzenesulfonyl)-α-(4-carboxy-2-n-propylphenoxy)-3,4-methylenedioxyphenyl-acetamide dipotassium salt, the dog is challenged with ET-1 again and the depressor and pressor effects on DBP are inhibited 70% and 75%, respectively. The pressor effect on IUP is inhibited 94%.

Intra-arterial Phenylephrine (PE)-induced increases in DBP and IUP did not change significantly after administration of N-(4-isopropyl-$d_7$-benzenesulfonyl)-α-(4-carboxy-2-n-propylphenoxy)-3,4-methylenedioxyphenyl-acetamide dipotassium salt in one dog studied. Increases in DBP and IUP are inhibited 33 and 11%, respectively.

ET-1 causes constriction of the prostatic urethra, as well as a complex hemodynamic response comprised of an initial depressor and subsequent pressor response in anesthetized dogs. The hemodynamic and prostatic urethral responses to ET-1 are specifically inhibited by N-(4-isopropyl-$d_7$-benzenesulfonyl)-α-(4-carboxy-2-n-propylphenoxy)-3,4-methylenedioxyphenyl-acetamide dipotassium salt. The efficacy of the N-(4-isopropyl-$d_7$-benzenesulfonyl)-α-(4-carboxy-2-n-propylphenoxy)-3,4-methylenedioxyphenyl-acetamide dipotassium salt in inhibiting the prostatic urethral effect of ET-1 suggests that selective antagonists of ET-1 will be useful in the treatment of urinary obstruction in benign prostatic hyperplasia.

In Situ Rat Prostate:

Male Sprague-Dawley rats weighing 300-400 grams are anesthetized with urethane (1.75 g/kg, ip), a tracheal cannula is inserted, and the femoral artery is cannulated. Core body temperature is maintained at 37° C. A 4-5 cm midline abdominal incision is made to expose the bladder and prostate. The prostate is separated from the bladder and surrounding capsule by blunt dissection with a forcep. A length of surgical silk is gently secured around the anterior tips of the prostate lobes. A second length of surgical silk attached to an atraumatic needle is passed through and tied to the base of the prostate approximately 10-12 mm posterior to the first tie. The posterior ligature is secured to an anchor post whereas the anterior ligature is connected to a Grass FT03 transducer and maintained at a tension of 1 g. Signals from the transducer are amplified and recorded on a polygraph (Hewlett-Packard 8805B amplifiers and 7758 recorder, Palo Alto, CA). After equilibrating for over 15 min, the rats are administered pretreatment drugs (atropine 1 mg/kg, (+) propranolol 1 mg/kg) 10 min apart through the intra-arterial (IA) cannula. Thirty minutes later, ET-1 (0.3 nmoles/kg) is injected intra-arterial every thirty minutes for three times. Five minutes prior to the third injection of ET-1, vehicle with or without an endothelin antagonist is injected IA. The response of the prostate to ET-1 is quantified by measuring the change from baseline tension to the peak of the response during the five-minute period after the third ET-1 injection.

The in situ rat prostate protocol is utilized to determine the antagonist activity and potency of compounds of this invention to block the direct contractile effects of ET-1 on the rat prostate in vivo. In this protocol, N-(4-isopropyl-$d_7$-benzenesulfonyl)-α-(4-carboxy-2-n-propylphenoxy)-3,4-methylenedioxyphenyl-acetamide dipotassium salt is demonstrated to cause a specific inhibition of ET-1 to contract the prostate and will be useful in the treatment of urinary obstruction in benign prostate hyperplasia.

Accordingly, the novel compounds of the present invention are useful in human therapy for treating pulmonary arterial hypertension, pulmonary hypertension associated with chronic obstructive pulmonary disease (COPD), right ventricular hypertrophy, pulmonary vascular remodeling, lung fibrosis, hypertension, left ventricular hypertrophy, congestive heart failure, arrhythmia, arterial fibrillation, digital ulcers, idiopathic pulmonary fibrosis, idiopathic pulmonary hypertension, acute kidney disease, chronic kidney disease, renal failure, cyclosporin-induced renal failure, IgA nephropathy (IgAN), focal segmental glomerulosclerosis (FSGS), diabetic nephropathy, scleroderma, digital ulcers, prostate cancer, breast cancer, lung cancer, ovarian cancer, colon cancer, kidney cancer, arteriosclerosis, myocardial infarction, angina pictoris, cerebral and cardiac ischemia, post-ischemic renal failure, stroke, vasospasm, Raynaud's disease, asthma, diabetes, obesity, erectile dysfunction, benign prostatic hyperplasia, endotoxic shock, endotoxin-induced, multiple organ failure, sepsis, inflammatory bowel diseases, Crohn's disease and ulcerative colitis, caused by or associated with endothelin, by administration to a patient in need of such treatment of a therapeutically effective amount thereof.

In the management or treatment of pulmonary arterial hypertension, idiopathic pulmonary fibrosis, idiopathic pulmonary hypertension, acute kidney failure, cyclosporin-induced renal failure, IgA nephropathy (IgAN), focal segmental glomerulosclerosis (FSGS), chronic kidney failure, end-stage kidney disease, diabetic nephropathy, scleroderma, digital ulcers, prostate cancer, breast cancer, lung cancer, ovarian cancer, colon cancer, kidney cancer, and all other clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (humans and animals) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 0.5 mg to 1.0 gram per patient per day which can be administered in single or multiple doses. Preferably, the dosage range will be about 0.5 mg to 500 mg per patient per day; more preferably about 0.5 mg to 250 mg per patient per day.

The compounds of this invention can also be administered in combination with angiotensin II receptor antagonists (e.g. losartan, valsartan, irbesartan, candesartan, olmesartan, telmisartan and eprosartan), angiotensin converting enzymes (e.g. captopril, enalapril, lisinopril, benazepril, delapril, fosinopril, ramipril, pentopril, perindopril, quinapril, zofenopril, and their salts), beta(β)-adrenergic antagonists, renin inhibitors, atriopeptidase inhibitors (alone or with ANP), calcium channel blockers, diuretics, potassium channel agonists, serotonin antagonists, sympatholytic agents, as well as other antihypertensive agents. For example, the compounds of this invention can be given in combination with such compounds as prostacyclins, serotonin antagonists, amiloride, atenolol, atriopeptin, bendroflumethiazide, chlorothalidone, chlorothiazide, clonidine, cromakalin, cryptenamine acetates, cryptenamine tannates, deserpidine diazoxide, doxazosin, guanabenz, guanethidine, guanethidine sulfate, hydralazine hydrochloride, isradipine, ketanserin, metolazone, metoprolol, metoprolol tartrate, methylclothiazide, methyldopa, methyldopate hydrochloride, minoxidil, nadolol, pargyline hydrochloride, pinacidil, polythiazide, prazosin, propranolol, rauwolfia serpentine, rescinnamine, reserpine, sodium nitroprusside, spironolactone, terazosin, timolol, maleate, trichloromethiazide, trimethaphan camsylate, verapamil, benzthiazide, quinethazone, ticrynafen, triamterene, acetazolamide, aminophylline procaine, sodium ethacrynate, diltiazem, felodipine, nicardipine, nifedipine, niludipine, nimodipine, nisoldipine, nitrendipine and the like, as well as admixtures and combinations thereof. Combinations useful in the management and treatment of congestive heart failure include, in addition, compounds of this invention with cardiac stimulants such as dobutamine and xamoterol and phosphodiesterase inhibitors including amrinone and milrinone.

The compounds of this invention can also be administered and used for treating diseases in combination with Serotonin receptor antagonists such as 5-$HT_{2B}$ receptor antagonists. The 5-$HT_{2B}$ (5-Hydroxytryptamine-2B) receptor antagonists are known to be potential therapeutic agents for the treatment of pulmonary arterial hypertension, right ventricular hypertrophy, pulmonary vascular remodeling, idiopathic pulmonary hypertension, idiopathic pulmonary fibrosis, pulmonary hypertension associated with chronic obstructive pulmonary diseases (COPD), asthma, hypertension, heart failure, chronic kidney disease, focal segmental glomerulosclerosis (FSGS), proteinuria and other fibrotic diseases. The 5-$HT_{2B}$ receptor antagonists are selected from the group consisting of the following compounds shown below.

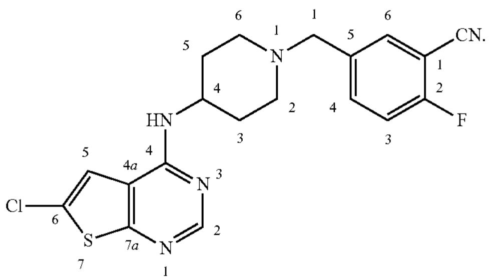

5-((4-((6-chlorothieno[2,3-d]pyrimidin-4-yl)amino)piperidin-1-yl)methyl)-2-fluorobenzonitrile

[Dhanoa et al. US Patent Number: US 7,030,240 B2]

-continued

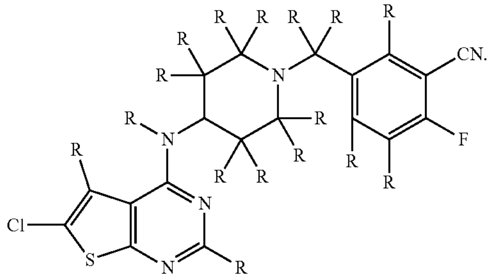

R = D or H

[Dhanoa, D. S., US Patent Number: US 8,618,116 B2; Dhanoa, D. S., US Patent Number: US 9,271,979 B2; Dhanoa, D. S., US Patent Number: US 9,271,980 B2]

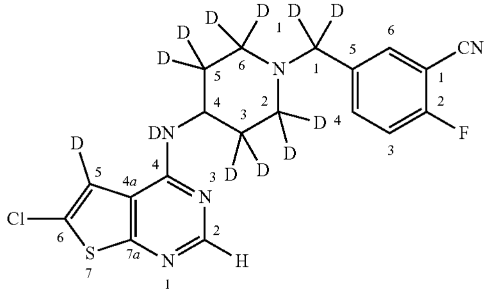

5-((4-((6-chlorothieno[2,3-d]pyrimidin-4-yl-5-d)amino-d) piperidin-1-yl-2,2,3,3,5,5,6,6-$d_8$)methyl-$d_2$)-2-fluorobenzonitrile

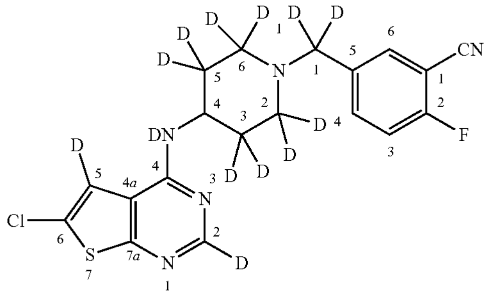

5-((4-((6-chlorothieno[2,3-d]pyrimidin-4-yl-2,5-$d_2$)amino-d) piperidin-1-yl-2,2,3,3,5,5,6,6-$d_8$)methyl-$d_2$)-2-fluorobenzonitrile

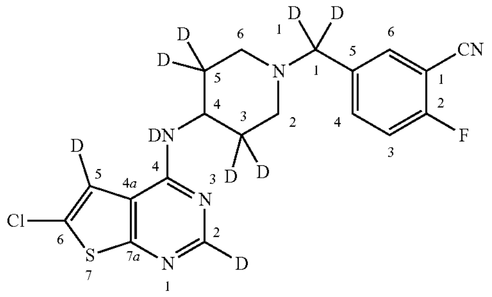

5-((4-((6-chlorothieno[2,3-d]pyrimidin-4-yl-2,5-$d_2$)amino-d) piperidin-1-yl-3,3,5,5-$d_4$)methyl-$d_2$)-2-fluorobenzonitrile -continued

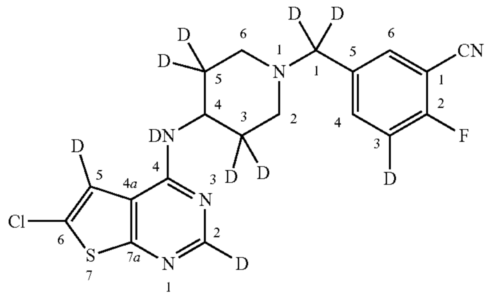

5-((4-((6-chlorothieno[2,3-d]pyrimidin-4-yl-2,5-$d_2$)amino-d)piperidin-1-yl-3,3,5,5-$d_4$)methyl-$d_2$)-2-fluorobenzonitrile-3-d

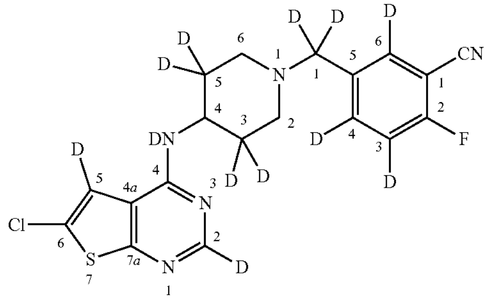

5-((4-((6-chlorothieno[2,3-d]pyrimidin-4-yl-2,5-$d_2$)amino-d)piperidin-1-yl-3,3,5,5-$d_4$)methyl-$d_2$)-2-fluorobenzonitrile-3,4,6-$d_3$

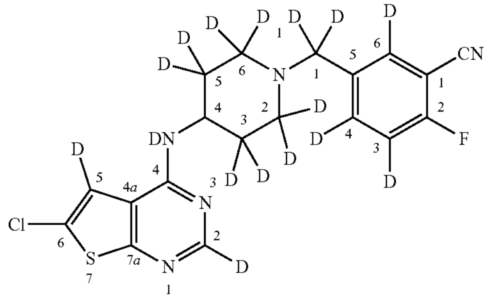

5-((4-((6-chlorothieno[2,3-d]pyrimidin-4-yl-2,5-$d_2$)amino-d)piperidin-1-yl-2,2,3,3,5,5,6,6-$d_8$)methyl-$d_2$)-2-fluorobenzonitrile-3,4,6-$d_3$

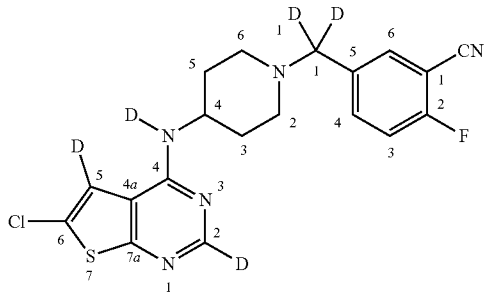

5-((4-((6-chlorothieno[2,3-d]pyrimidin-4-yl-2,5-$d_2$)amino-d)piperidin-1-yl)methyl-$d_2$)-2-fluorobenzonitrile -continued

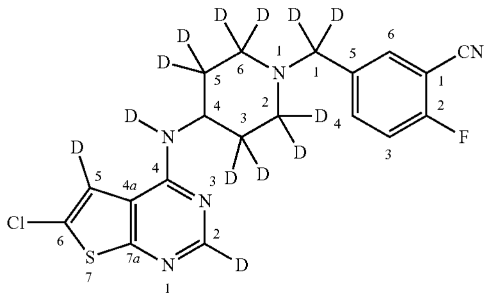

5-((4-((6-chlorothieno[2,3-d]pyrimidin-4-yl-2,5-$d_2$)amino-d)piperidin-1-yl-2,2,3,3,5,5,6,6-$d_8$)methyl-$d_2$)-2-fluorobenzonitrile

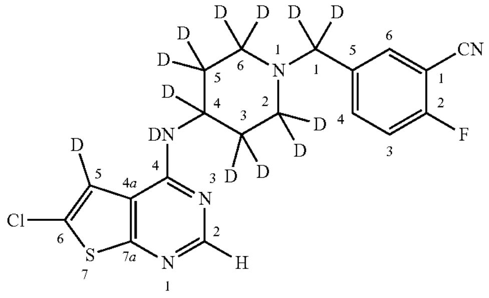

5-((4-((6-chlorothieno[2,3-d]pyrimidin-4-yl-5-d)amino-d)piperidin-1-yl-2,2,3,3,4,5,5,6,6-$d_9$)methyl-$d_2$)-2-fluorobenzonitrile

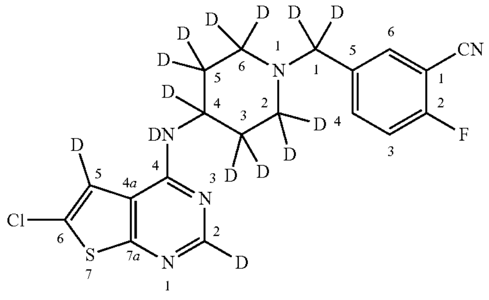

5-((4-((6-chlorothieno[2,3-d]pyrimidin-4-yl-2,5-$d_2$)amino-d)piperidin-1-yl-2,2,3,3,4,5,5,6,6-$d_9$)methyl-$d_2$)-2-fluorobenzonitrile

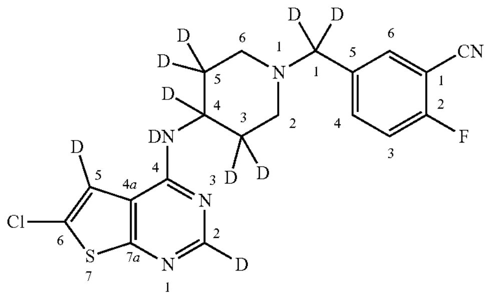

5-((4-((6-chlorothieno[2,3-d]pyrimidin-4-yl-2,5-$d_2$)amino-d)piperidin-1-yl-3,3,4,5,5-$d_5$)methyl-$d_2$)-2-fluorobenzonitrile -continued

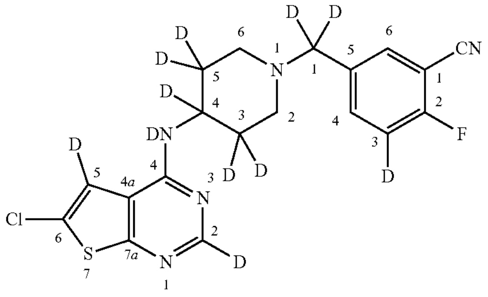

5-((4-((6-chlorothieno[2,3-d]pyrimidin-4-yl-2,5-$d_2$)amino-d)piperidin-1-yl-3,3,4,5,5-$d_5$)methyl-$d_2$)-2-fluorobenzonitrile-3-d

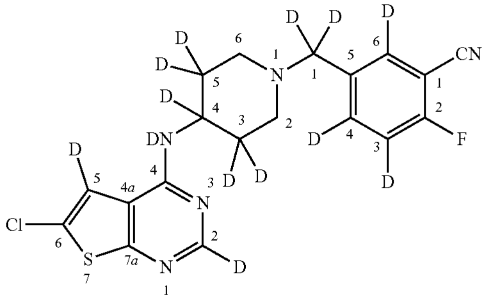

5-((4-((6-chlorothieno[2,3-d]pyrimidin-4-yl-2,5-$d_2$)amino-d)piperidin-1-yl-3,3,4,5,5-$d_5$)methyl-$d_2$)-2-fluorobenzonitrile-3,4,6-$d_3$

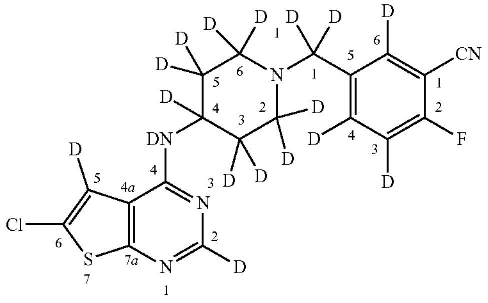

5-((4-((6-chlorothieno[2,3-d]pyrimidin-4-yl-2,5-$d_2$)amino-d)piperidin-1-yl-2,2,3,3,4,5,5,6,6-$d_9$)methyl-$d_2$)-2-fluorobenzonitrile-3,4,6-$d_3$

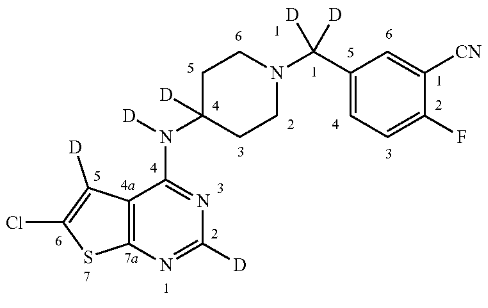

5-((4-((6-chlorothieno[2,3-d]pyrimidin-4-yl-2,5-$d_2$)amino-d)piperidin-1-yl-4-d)methyl-$d_2$)-2-fluorobenzonitrile -continued

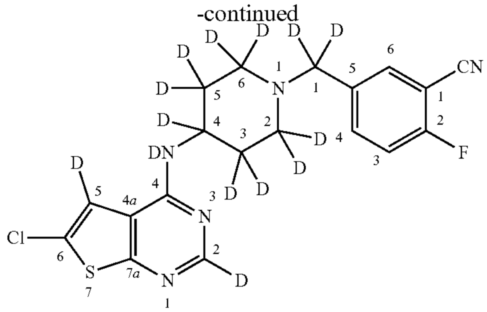

5-((4-((6-chlorothieno[2,3-d]pyrimidin-4-yl-2,5-$d_2$)amino-d)piperidin-1-yl-2,2,3,3,4,5,5,6,6-$d_9$)methyl-$d_2$)-2-fluorobenzonitrile and their pharmaceutically acceptable salts, solvates and enantiomers.

Typically, the individual daily dosages for these combinations can range from about one-fifth of the minimum recommended clinical dosages to the maximum recommended levels for those entities given singly. To illustrate these combinations, one of the endothelin antagonists of this invention effective clinically at a given daily dose range, with the following compounds at the indicated per day dose range: hydrochlorothiazide (6-100 mg), chlorothiazide (125-500 mg), furosemide (5-80 mg), ethacrynic acid (5-200 mg), amiloride (5-20 mg), diltiazem (30-540 mg), felodipine (1-20 mg), propranolol (10-480 mg), and methyldopa (125-2000 mg). In addition triple drug combinations of hydrochlorothiazide (6-100 mg) plus amiloride (5-20 mg) plus endothelin antagonists of this invention, or hydrochlorothiazide (6-100 mg) plus timolol maleate (1-20 mg) plus endothelin antagonists of this invention, or hydrochlorothiazide (6-100 mg) plus nifedipine (5-60 mg) plus endothelin antagonists of this invention are effective combinations to control blood pressure in hypertensive patients. Naturally, these dose ranges can be adjusted on a unit basis as necessary to permit divided daily dosage and the dosage will vary depending on the nature and severity of the disease, weight of the patient, special diets and others factors.

The present invention also relates to pharmaceutical compositions for treating pulmonary arterial hypertension, pulmonary hypertension associated with chronic obstructive pulmonary disease (COPD), right ventricular hypertrophy, pulmonary vascular remodeling, lung fibrosis, hypertension, left ventricular hypertrophy, congestive heart failure, arrhythmia, arterial fibrillation, digital ulcers, idiopathic pulmonary fibrosis, idiopathic pulmonary hypertension, acute kidney disease, chronic kidney disease, renal failure, cyclosporin-induced renal failure, IgA nephropathy (IgAN), focal segmental glomerulosclerosis (FSGS), diabetic nephropathy, scleroderma, digital ulcers, prostate cancer, breast cancer, lung cancer, ovarian cancer, colon cancer, kidney cancer, arteriosclerosis, myocardial infarction, angina pictoris, cerebral and cardiac ischemia, post-ischemic renal failure, stroke, vasospasm, Raynaud's disease, asthma, diabetes, obesity, erectile dysfunction, benign prostatic hyperplasia, endotoxic shock, endotoxin-induced, multiple organ failure, sepsis, inflammatory bowel diseases, Crohn's disease and ulcerative colitis, caused by or associated with endothelin, comprising a therapeutically effective amount of the novel compound of this invention together with a pharmaceutically acceptable carrier therefor.

About 0.01-1.0 gram of compound or mixture of compounds of Formula I or a physiologically acceptable salt is compounded with a physiologically acceptable vehicle, carrier, excipient, binder, preservative, stabilizer, flavor etc., in a unit dosage from as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is capsule, it may contain, in addition to materials of the above type, a liquid carrier such as fatty oil. Various other materials may be present as coatings or to otherwise modify the physical form of the dosage limit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. A deuterium-containing compound selected from the group consisting of:

(a) N-(4-isopropyl-$d_7$-benzenesulfonyl)-α-(4-carboxy-2-n-propyl-$d_7$)phenoxy)-3,4-methylenedioxyphenylacetamide;

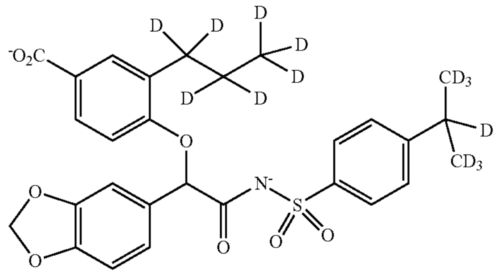

(b) N-(4-isopropyl-$d_7$-benzenesulfonyl)-α-$d_1$-(4-carboxy-2-n-propyl-$d_7$)phenoxy)-3,4-methylenedioxyphenylacetamide;

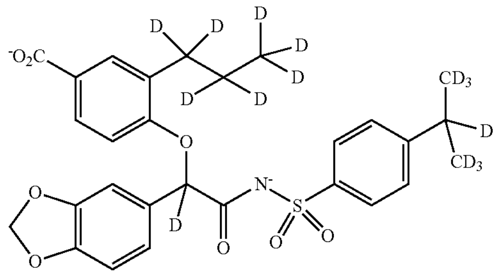

(c) N-(4-isopropyl-$d_7$-benzenesulfonyl)-α-$d_1$-(4-carboxy-2-n-propyl-$d_7$)phenoxy)-3,4-methylenedioxy-$d_2$-phenylacetamide;

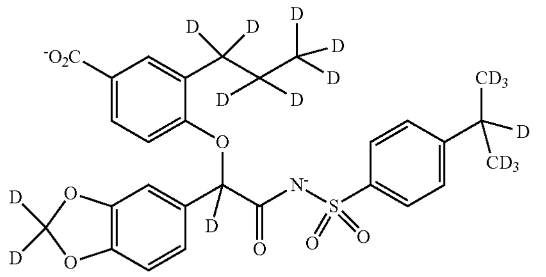

(d) N-(4-isopropyl-$d_7$-benzenesulfonyl)-α-(4-carboxy-2-n-propyl-$d_7$)phenoxy)-3,4-methylenedioxy-phenylacetamide;

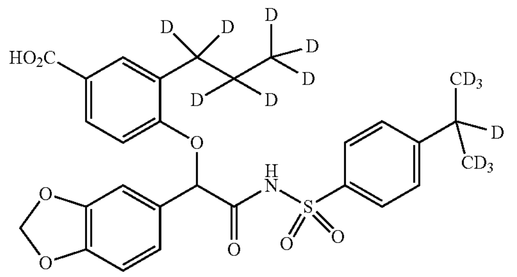 [SMILES: [2H]C([2H])([2H])C([2H])([2H])C([2H])([2H])c1cc(C(=O)O)ccc1OC(C(=O)NS(=O)(=O)c1ccc(C([2H])(C([2H])([2H])[2H])C([2H])([2H])[2H])cc1)c1ccc2c(c1)OCO2]

(e) N-(4-isopropyl-$d_7$-benzenesulfonyl)-α-$d_1$-(4-carboxy-2-n-propyl-$d_7$)phenoxy)-3,4-methylenedioxyphenylacetamide;

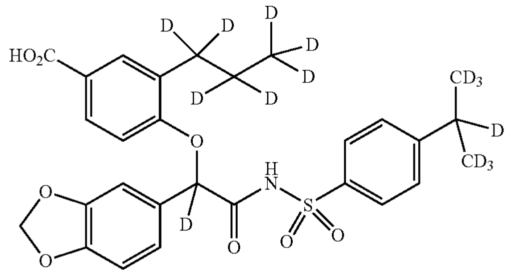

(f) N-(4-isopropyl-$d_7$-benzenesulfonyl)-α-$d_1$-(4-carboxy-2-n-propyl-$d_7$)phenoxy)-3,4-methylenedioxy-$d_2$-phenylacetamide;

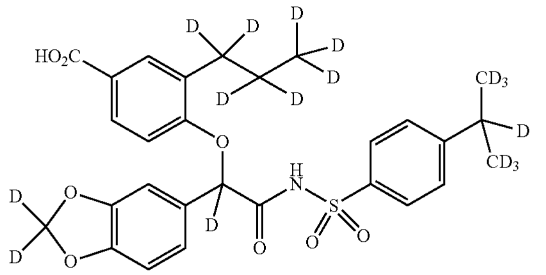 [SMILES: [2H]C1([2H])Oc2ccc(C([2H])(Oc3ccc(C(=O)O)cc3C([2H])([2H])C([2H])([2H])C([2H])([2H])[2H])C(=O)NS(=O)(=O)c3ccc(C([2H])(C([2H])([2H])[2H])C([2H])([2H])[2H])cc3)cc2O1]

(g) N-(4-isopropyl-$d_7$-benzenesulfonyl)-α-(4-carboxy-2-n-propyl-$d_5$)phenoxy)-3,4-methylenedioxyphenylacetamide:

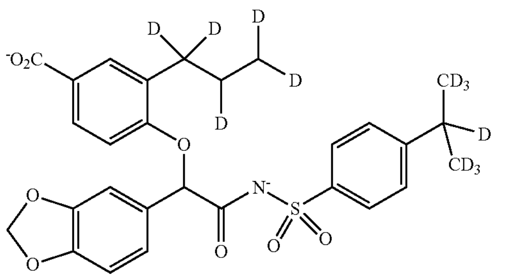

(h) N-(4-isopropyl-$d_7$-benzenesulfonyl)-α-$d_1$-(4-carboxy-2-n-propyl-$d_5$)phenoxy)-3,4-methylenedioxyphenylacetamide;

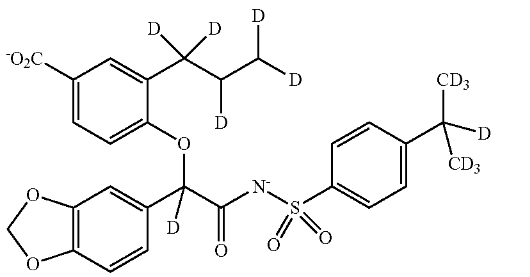

(i) N-(4-isopropyl-$d_7$-benzenesulfonyl)-α-$d_1$-(4-carboxy-2-n-propyl-$d_5$)phenoxy)-3,4-methylenedioxy-$d_2$-phenylacetamide;

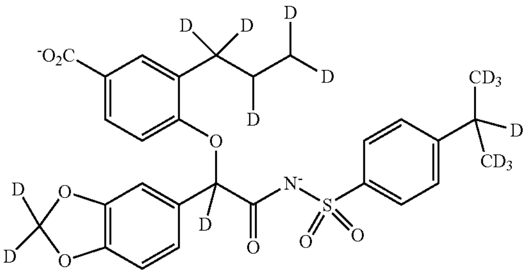

(j) N-(4-isopropyl-$d_7$-benzenesulfonyl)-α-(4-carboxy-2-n-propyl-$d_5$)phenoxy)-3,4-methylenedioxyphenylacetamide;

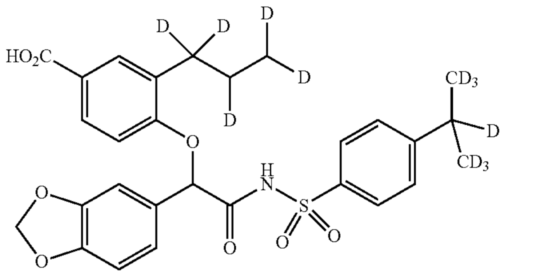 [SMILES: [2H]C([2H])C([2H])C([2H])([2H])c1cc(C(=O)O)ccc1OC(C(=O)NS(=O)(=O)c1ccc(C([2H])(C([2H])([2H])[2H])C([2H])([2H])[2H])cc1)c1ccc2c(c1)OCO2]

(k) N-(4-isopropyl-$d_7$-benzenesulfonyl)-α-$d_1$-(4-carboxy-2-n-propyl-$d_5$)phenoxy)-3,4-methylenedioxyphenylacetamide;

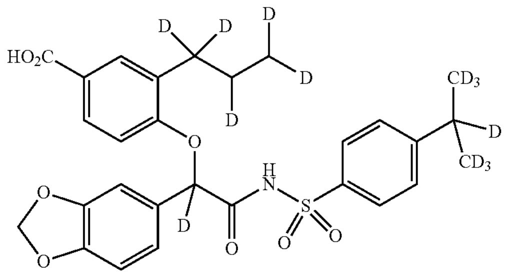 [SMILES: [2H]C([2H])C([2H])C([2H])([2H])c1cc(C(=O)O)ccc1OC([2H])(C(=O)NS(=O)(=O)c1ccc(C([2H])(C([2H])([2H])[2H])C([2H])([2H])[2H])cc1)c1ccc2c(c1)OCO2]

(l) N-(4-isopropyl-$d_7$-benzenesulfonyl)-α-$d_1$-(4-carboxy-2-n-propyl-$d_5$)phenoxy)-3,4-methylenedioxy-$d_2$-phenylacetamide;

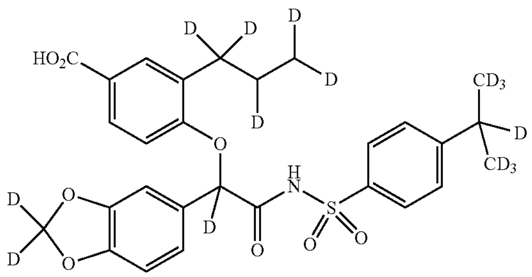

(m) N-(4-isopropyl-$d_7$-benzenesulfonyl)-α-(4-carboxy-2-n-propyl)phenoxy)-3,4-methylenedioxyphenylacetamide;

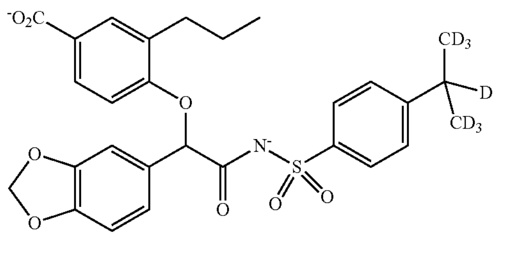

(n) N-(4-isopropyl-$d_7$-benzenesulfonyl)-α-$d_1$-(4-carboxy-2-n-propyl)phenoxy)-3,4-methylenedioxyphenylacetamide;

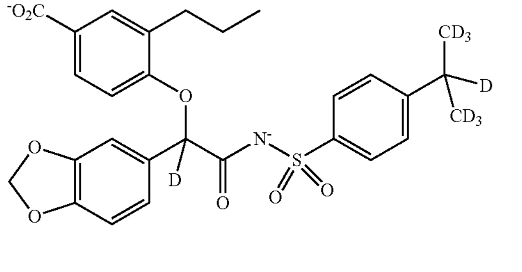

(o) N-(4-isopropyl-$d_7$-benzenesulfonyl)-α-$d_1$-(4-carboxy-2-n-propyl)phenoxy)-3,4-methylenedioxy-$d_2$-phenylacetamide;

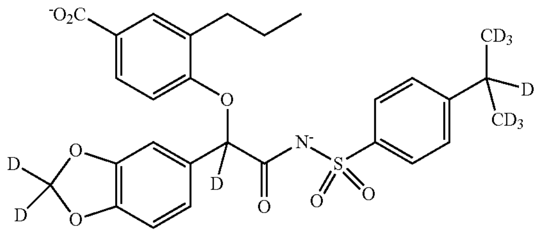

(p) N-(4-isopropylbenzenesulfonyl)-α-(4-carboxy-2-n-propyl-$d_7$)phenoxy)-3,4-methylenedioxyphenylacetamide;

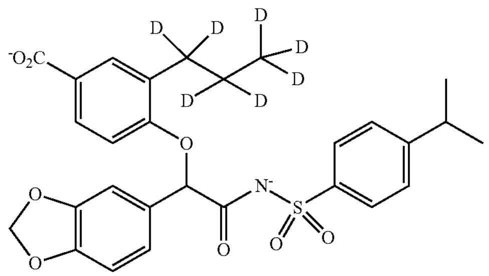

(q) N-(4-isopropylbenzenesulfonyl)-α-$d_1$-(4-carboxy-2-n-propyl-$d_7$)phenoxy)-3,4-methylenedioxyphenylacetamide;

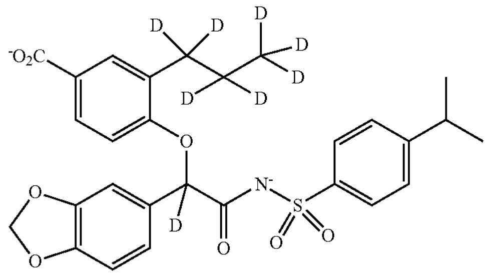

(r) N-(4-isopropylbenzenesulfonyl)-α-$d_1$-(4-carboxy-2-n-propyl-$d_7$)phenoxy)-3,4-methylenedioxy-$d_2$-phenylacetamide;

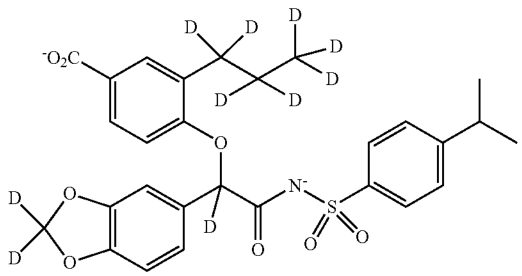

(s) N-(4-isopropyl-$d_7$-benzenesulfonyl)-α-(4-carboxy-$d_1$-2-n-propyl-$d_7$)phenoxy)-3,4-methylenedioxyphenylacetamide-$d_1$;

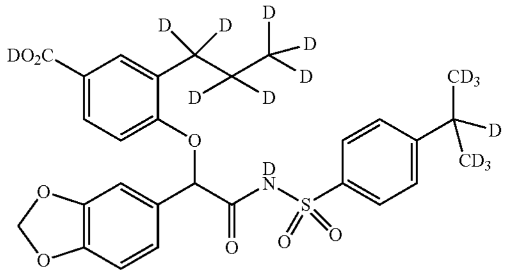

(t) N-(4-isopropyl-$d_7$-benzenesulfonyl)-α-$d_1$-(4-carboxy-$d_1$-2-n-propyl-$d_7$)phenoxy)-3,4-methylenedioxyphenylacetamide-$d_1$;

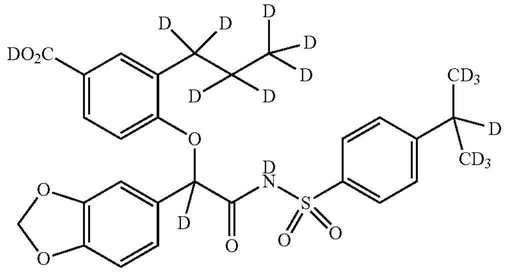

(u) N-(4-isopropyl-$d_7$-benzenesulfonyl)-α-$d_1$-(4-carboxy-$d_1$-2-n-propyl-$d_7$)phenoxy)-3,4-methylenedioxy-$d_2$-phenylacetamide-$d_1$;

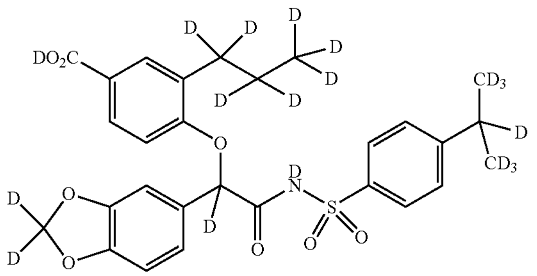

(v) N-(4-isopropyl-$d_7$-benzenesulfonyl)-α-(4-carboxy-$d_1$-2-n-propyl-$d_5$)phenoxy)-3,4-methylenedioxyphenylacetamide-$d_1$;

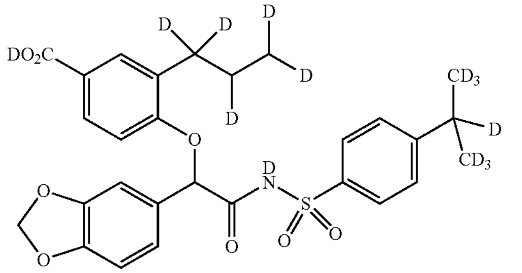

(w) N-(4-isopropyl-$d_7$-benzenesulfonyl)-α-$d_1$-(4-carboxy-$d_1$-2-n-propyl-$d_5$)phenoxy)-3,4-methylenedioxyphenylacetamide-$d_1$;

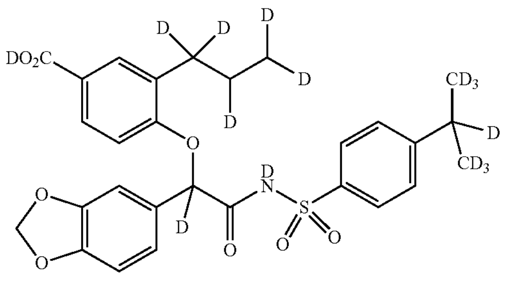

(x) N-(4-isopropyl-$d_7$-benzenesulfonyl)-α-$d_1$-(4-carboxy-$d_1$-2-n-propyl-$d_5$)phenoxy)-3,4-methylenedioxy-$d_2$-phenylacetamide-$d_1$;

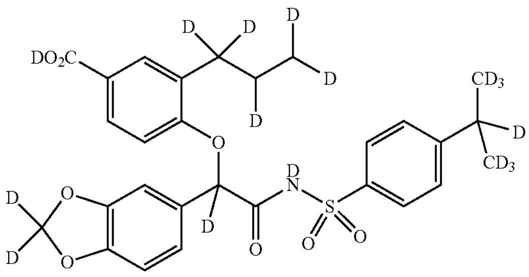

(y) N-(4-isopropyl-$d_7$-benzenesulfonyl)-α-(4-carboxy-$d_1$-2-n-propyl-$d_5$)phenoxy)-3,4-methylenedioxyphenylacetamide-$d_1$;

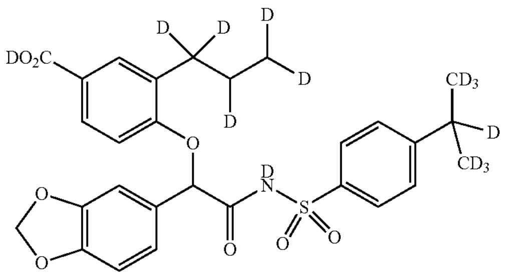

(z) N-(4-isopropyl-$d_7$-benzenesulfonyl)-α-$d_1$-(4-carboxy-$d_1$-2-n-propyl-$d_5$)phenoxy)-3,4-methylenedioxyphenylacetamide-$d_1$;

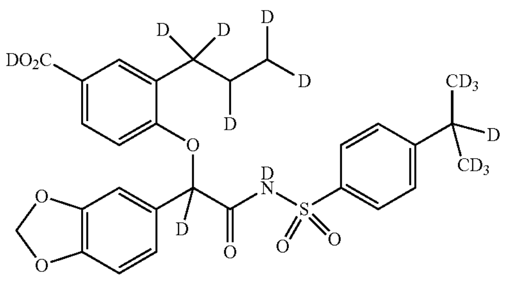

(za) N-(4-isopropyl-$d_7$-benzenesulfonyl)-α-$d_1$-(4-carboxy-$d_1$-2-n-propyl-$d_5$)phenoxy)-3,4-methylenedioxy-$d_2$-phenylacetamide-$d_1$;

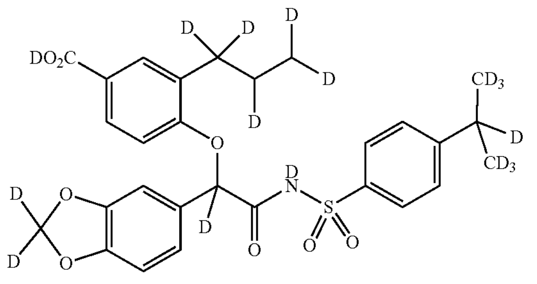

(zb) N-(4-isopropyl-$d_7$-benzenesulfonyl)-α-(4-carboxy-$d_1$-2-n-propyl)phenoxy)-3,4-methylenedioxyphenylacetamide-$d_1$;

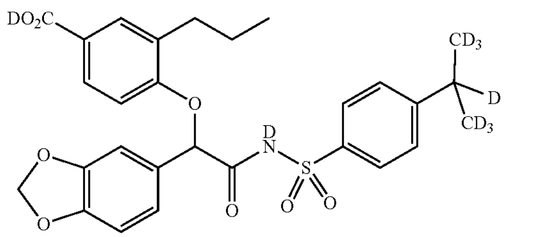

(zc) N-(4-isopropyl-$d_7$-benzenesulfonyl)-α-$d_1$-(4-carboxy-$d_1$-2-n-propyl)phenoxy)-3,4-methylenedioxyphenylacetamide-$d_1$;

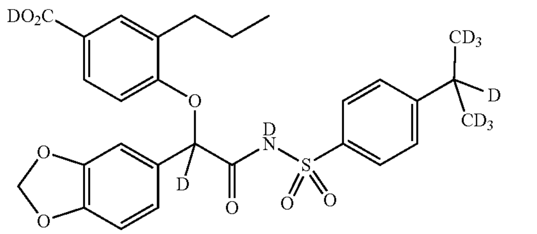

(zd) N-(4-isopropyl-$d_7$-benzenesulfonyl)-α-$d_1$-(4-carboxy-$d_1$-2-n-propyl)phenoxy)-3,4-methylenedioxy-$d_2$-phenylacetamide-$d_1$;

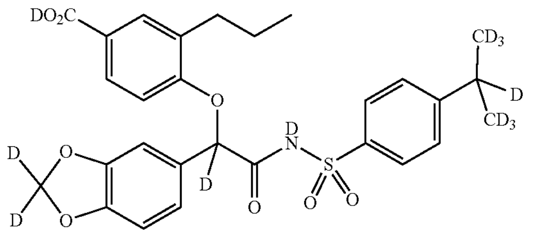

(ze) N-(4-isopropylbenzenesulfonyl)-α-(4-carboxy-$d_1$-2-n-propyl-$d_7$)phenoxy)-3,4-methylenedioxyphenylacetamide-$d_1$;

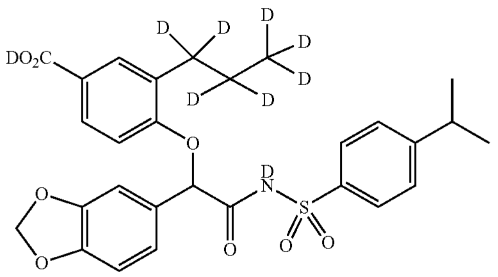

(zf) N-(4-isopropylbenzenesulfonyl)-$\alpha$-$d_1$-(4-carboxy-$d_1$-2-n-propyl-$d_7$)phenoxy)-3,4-methylenedioxyphenylacetamide-$d_1$;

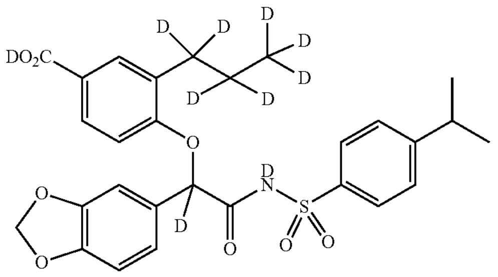

(zg) N-(4-isopropylbenzenesulfonyl)-$\alpha$-$d_1$-(4-carboxy-2-n-propyl-$d_7$)phenoxy)-3,4-methylenedioxy-$d_2$-phenylacetamide;

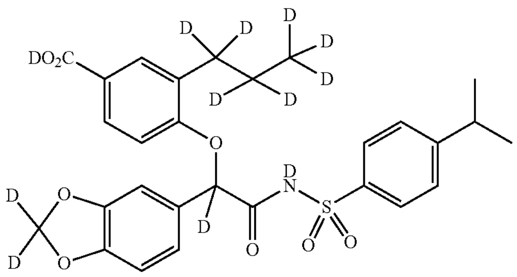

(zh) N-(4-isopropyl-$d_7$-benzenesulfonyl)-$\alpha$-(4-carboxy-2-n-propyl)phenoxy)-3,4-methylenedioxyphenylacetamide;

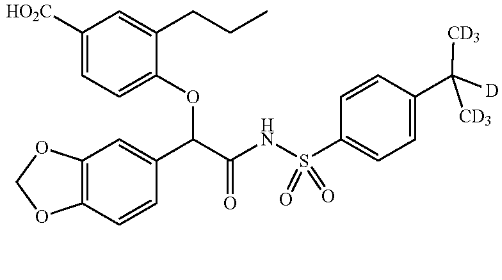 [SMILES: [2H]C([2H])([2H])C([2H])(c1ccc(S(=O)(=O)NC(=O)C(Oc2ccc(C(=O)O)cc2CCC)c2ccc3c(c2)OCO3)cc1)C([2H])([2H])[2H]]

(zi) N-(4-isopropyl-$d_7$-benzenesulfonyl)-$\alpha$-$d_1$-(4-carboxy-2-n-propyl)phenoxy)-3,4-methylenedioxyphenylacetamide;

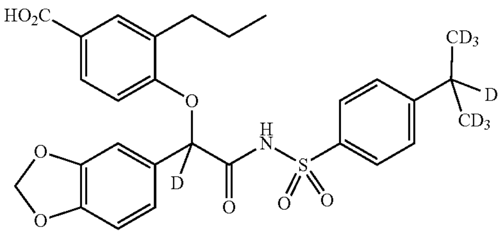

(zj) N-(4-isopropyl-$d_7$-benzenesulfonyl)-$\alpha$-$d_1$-(4-carboxy-2-n-propyl)phenoxy)-3,4-methylenedioxy-$d_2$-phenylacetamide;

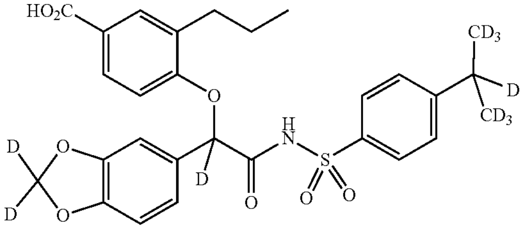

(zk) N-(4-isopropylbenzenesulfonyl)-$\alpha$-(4-carboxy-2-n-propyl-$d_7$)phenoxy)-3,4-methylenedioxyphenylacetamide;

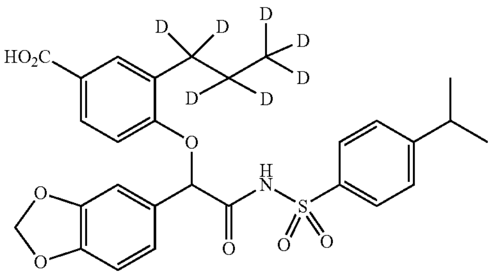

(zl) N-(4-isopropylbenzenesulfonyl)-$\alpha$-$d_1$-(4-carboxy-2-n-propyl-$d_7$)phenoxy)-3,4-methylenedioxyphenylacetamide;

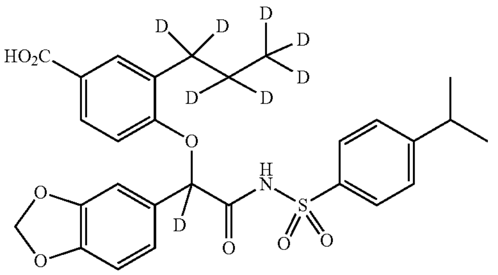 [SMILES: [2H]C(Oc1ccc(C(=O)O)cc1C([2H])([2H])C([2H])([2H])C([2H])([2H])[2H])(C(=O)NS(=O)(=O)c1ccc(C(C)C)cc1)c1ccc2c(c1)OCO2]

(zm) N-(4-isopropylbenzenesulfonyl)-$\alpha$-$d_1$-(4-carboxy-2-n-propyl-$d_7$)phenoxy)-3,4-methylenedioxy-$d_2$-phenylacetamide;

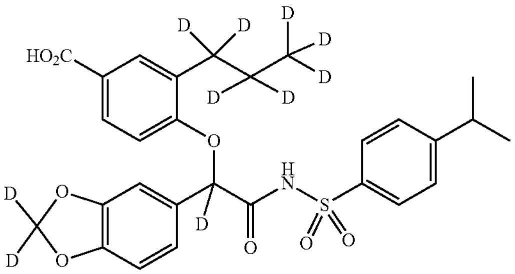 [SMILES: [2H]C1([2H])Oc2ccc(C([2H])(Oc3ccc(C(=O)O)cc3C([2H])([2H])C([2H])([2H])C([2H])([2H])[2H])C(=O)NS(=O)(=O)c3ccc(C(C)C)cc3)cc2O1]
or a pharmaceutically acceptable salt, solvate or enantiomers thereof.
* * * * *